US010472635B2

United States Patent
Snutch et al.

(10) Patent No.: US 10,472,635 B2
(45) Date of Patent: Nov. 12, 2019

(54) METHODS OF TREATING BRAIN EDEMA

(71) Applicants: Terrance P. Snutch, Vancouver (CA); Ravi Rungta, Vancouver (CA); Choi Hyun, Vancouver (CA); John Tyson, North Vancouver (CA); Brian Macvicar, Vancouver (CA)

(72) Inventors: Terrance P. Snutch, Vancouver (CA); Ravi Rungta, Vancouver (CA); Choi Hyun, Vancouver (CA); John Tyson, North Vancouver (CA); Brian Macvicar, Vancouver (CA)

(*) Notice: Subject to any disclaimer, the term of this patent is extended or adjusted under 35 U.S.C. 154(b) by 0 days.

(21) Appl. No.: 15/549,620

(22) PCT Filed: Feb. 17, 2016

(86) PCT No.: PCT/US2016/018292
§ 371 (c)(1),
(2) Date: Aug. 8, 2017

(87) PCT Pub. No.: WO2016/134032
PCT Pub. Date: Aug. 25, 2016

(65) Prior Publication Data
US 2018/0195075 A1 Jul. 12, 2018

Related U.S. Application Data

(60) Provisional application No. 62/131,182, filed on Mar. 10, 2015, provisional application No. 62/117,287, filed on Feb. 17, 2015.

(51) Int. Cl.
*C12N 15/113* (2010.01)
*A61K 45/06* (2006.01)
*A61P 25/00* (2006.01)
*A61K 31/00* (2006.01)
*C07K 16/28* (2006.01)

(52) U.S. Cl.
CPC .......... *C12N 15/1138* (2013.01); *A61K 31/00* (2013.01); *A61K 45/06* (2013.01); *A61P 25/00* (2018.01); *C07K 16/28* (2013.01); *C12N 2310/14* (2013.01); *C12N 2320/32* (2013.01)

(58) Field of Classification Search
CPC ............ C12N 15/1138; C12N 2320/32; C12N 2310/14; C07K 16/28; A61P 25/00
See application file for complete search history.

(56) References Cited

FOREIGN PATENT DOCUMENTS

EP    1 818 063 A1    8/2007

OTHER PUBLICATIONS

Müller M. Effects of chloride transport inhibition and chloride substitution on neuron function and on hypoxic spreading-depression-like depolarization in rat hippocampal slices. Neuroscience, 2000, 97:33-45. (Year: 2000).*
Takahashi N et al. Different characteristics of cell volume and intracellular calcium ion concentration dynamics between the hippocampal CA1 and lateral cerebral cortex of male mouse brain slices during exposure to hypotonic stress. J. Neuro. Res. 2018, 96:117-127. (Year: 2018).*
Xu J et al. Slc26a11, a chloride transporter, localizes with the vacuolar H+-ATPase of A-intercalated cells of the kidney. Kidney International, 2011, 80:926-937. (Year: 2011).*
Dijkstra K et al. A biophysical model for cytotoxic cell swelling. J. Neurosci. 36(47):11881-11890. (Year: 2016).*
Rungta RL et al. Lipid nanoparticle delivery of siRNA to silence neuronal gene expression in the brain. Mol. Ther. Nucleic Acids, 2, e136. (Year: 2013).*
Kumar et al., "Effects of chloride flux modulators in an in vitro model of brain edema formation," Brain Research 1122: 222-229, 2006.
Rahmati et al., "Slc26a11 is prominently expressed in the brain and functions as a chloride channel: expression in Purkinje cells and stimulation of V H+-ATPase," Pflugers Arch—Eur. J. Physiol. 465: 1583-1597, 2013.
Rungta, Ravi Logan, "Cellular Mechanisms of Neuronal Swelling Underlying Cytotoxic Edema," A Thesis Submitted in Partial Fulfillment of the Requirements for the degree of Doctor of Philosophy in the Faculty of Graduate and Postdoctoral Studies (Neuroscience), The University of British Columbia (Vancouver) Jul. 2014, retrieved from open.library.ubc.ca/clRcle/collections/. pp. 40-42, 126-155.

* cited by examiner

*Primary Examiner* — Kimberly Ballard
(74) *Attorney, Agent, or Firm* — Cooley LLP

(57) ABSTRACT

Provided are methods for treating or preventing brain edema in a subject by administering an inhibitor of SLC26A11 to the subject. Also included are methods for preventing cell death, cell swelling, or elevated internal concentration of chloride ions in a cell by contacting the cell with an inhibitor of SLC26A11.

14 Claims, 21 Drawing Sheets
Specification includes a Sequence Listing.

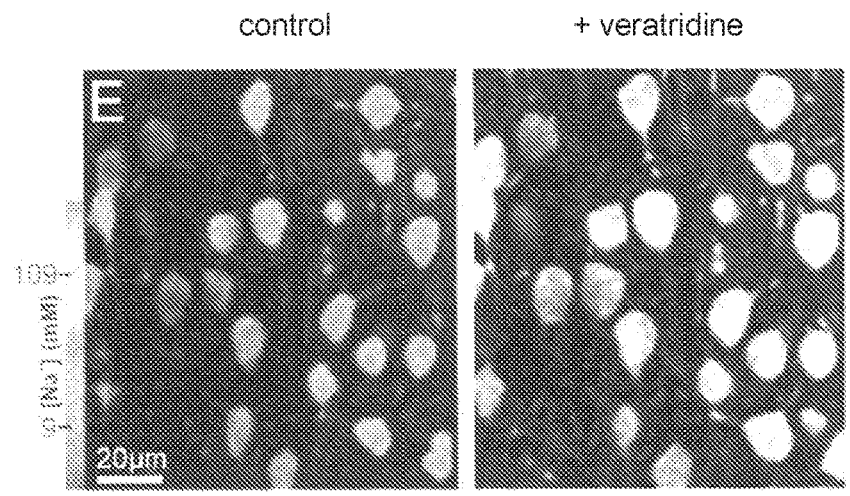
FIG. 1E
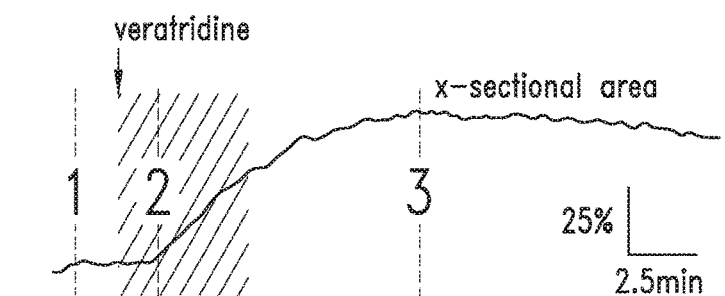
FIG. 1C
FIG. 1D
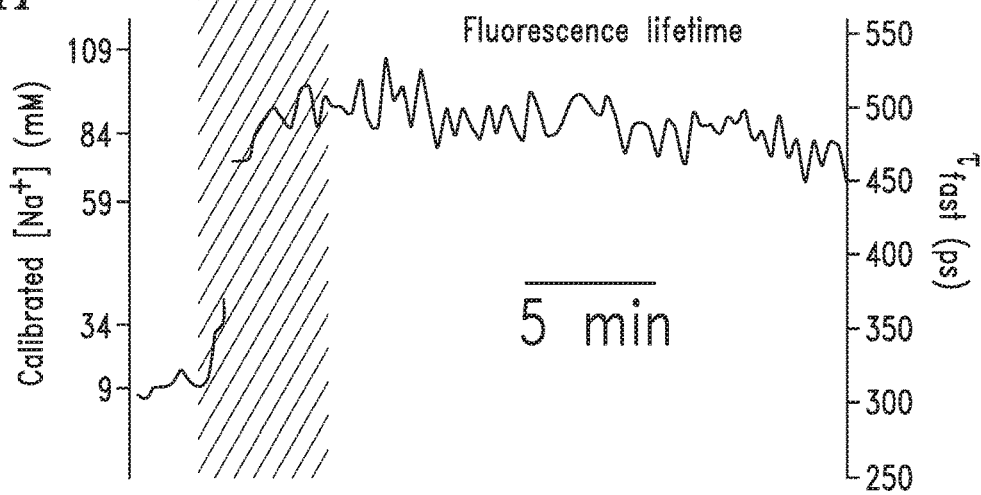
FIG. 1F

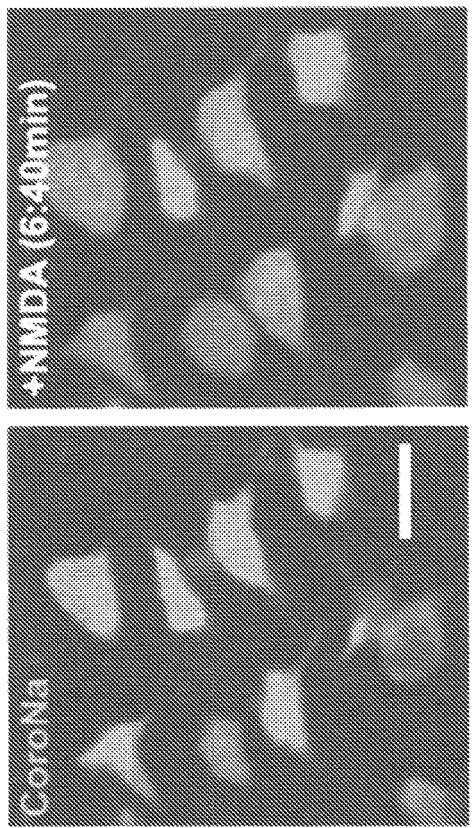
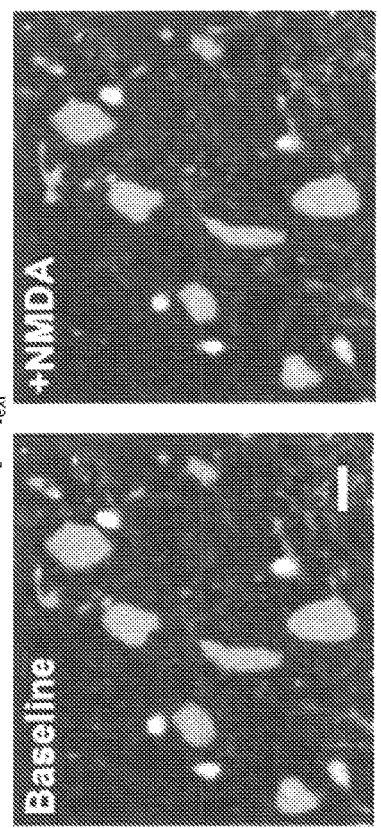
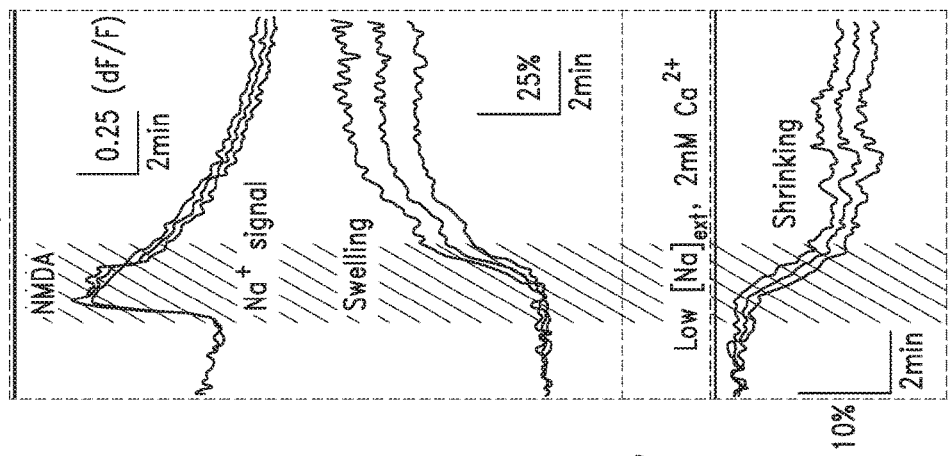
FIG. 2A  FIG. 2B  FIG. 2C  FIG. 2D

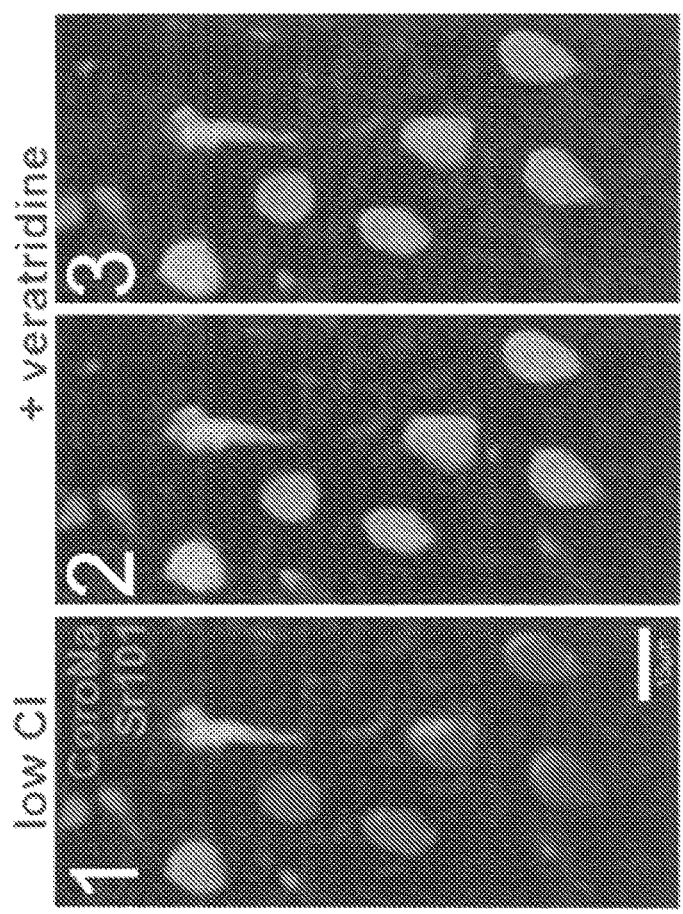
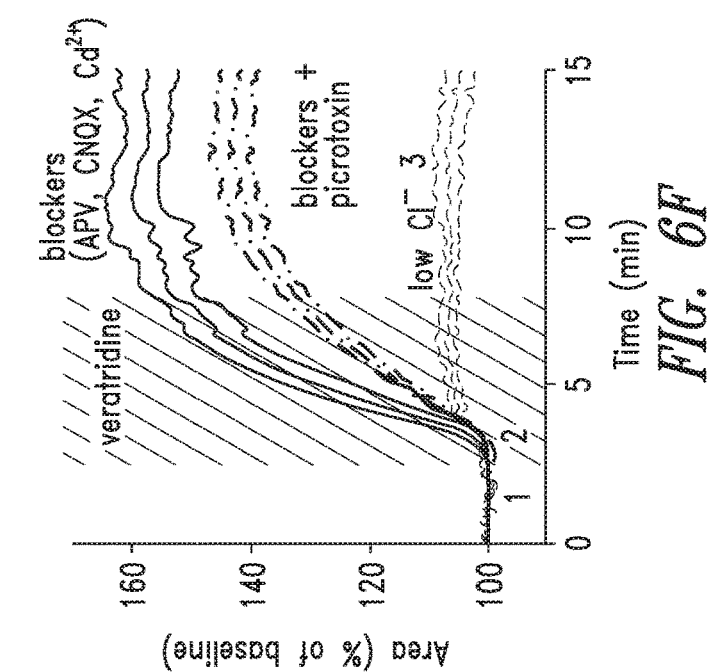
FIG. 6E
FIG. 6F

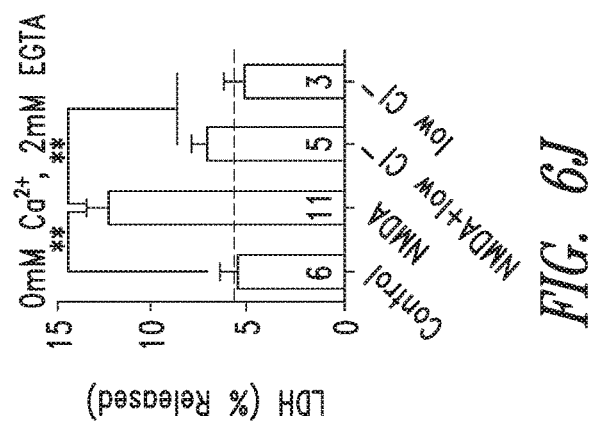
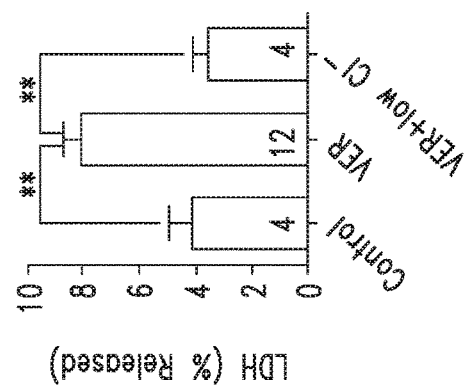
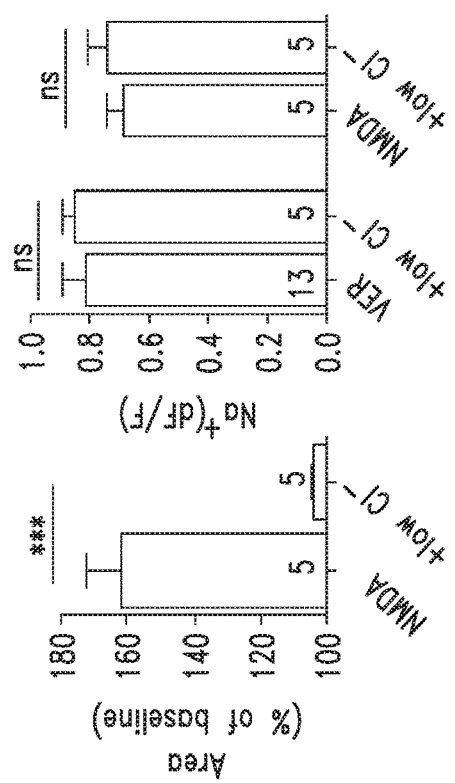
FIG. 6G  FIG. 6H  FIG. 6I  FIG. 6J

METHODS OF TREATING BRAIN EDEMA

STATEMENT OF RELATED APPLICATIONS

This application is a U S national phase of International Application No. PCT/US2016/018292, filed Feb. 17, 2016, which claims priority to U.S. Provisional Patent Application No. 62/117,287, filed on Feb. 17, 2015, and U.S. Provisional Patent Application No. 62/131,182, filed on Mar. 10, 2015; both of which are incorporated by reference in their entirety.

DESCRIPTION OF THE TEXT FILE SUBMITTED ELECTRONICALLY

The contents of the text file submitted electronically herewith are incorporated herein by reference in their entirety: a computer readable format copy of the Sequence Listing (filename: TSPD_001_01WO_ST25.txt, date recorded: Feb. 17, 2016, file size: 33 kilobytes.

BACKGROUND

Brain edema (also known as cerebral edema, brain oedema, cerebral oedema, brain swelling, or wet brain) is excess accumulation of fluid in the intracellular or extracellular spaces of the brain. Brain edema is broadly classified as vasogenic (movement of water and solutes across the blood brain barrier), or cytotoxic (osmotic swelling of cells in the affected area). In most instances, cytotoxic and vasogenic edema occur together. It is generally accepted that cytotoxic edema is dominant immediately following an injury or infarct, but gives way to a vasogenic edema that can persist for several days or longer.

Cytotoxic Edema in the brain is typically accompanied by brain swelling. Edema can result from almost any insult to the brain, including trauma, infarction, neoplasm, abscess, or conditions such as hypoxia or exposure to toxic compounds. Cytotoxic edema (also known as cellular edema, oncotic cell swelling, or oncosis) is a cellular process whereby extracellular $Na^+$ and other cations are thought to enter into brain cells and accumulate intracellularly. The cation influx, in turn, drives influx of anions such as $Cl^-$, which maintains electrical neutrality but generates an influx of water, resulting in cytotoxic edema through osmotic expansion of the cell. While the cytotoxic edema alone does not completely account for brain swelling, the formation of cytotoxic edema depletes the extracellular space of $Na^+$, Cl–, and water, thereby creating a new gradient for these molecules across the capillary of the blood-brain barrier, thereby contributing to vasogenic edema. Cytotoxic edema evolves over minutes to hours and may be reversible, while the vasogenic phase occurs over hours to days, and is considered an irreversibly damaging process. Therefore, treatments to address cytotoxic edema in its early stages are desired. However, clinically acceptable strategies for management of brain edema have remained elusive, and available treatments are often of limited value for patients with brain edema. What is needed in the art are methods for the treatment of brain edema. The present invention provides methods of treating brain edema by inhibiting SLC26A11.

BRIEF SUMMARY OF THE INVENTION

Some embodiments are directed to a method for ameliorating death of a cell, comprising contacting the cell with an inhibitor of SLC26A11. In certain embodiments, the cell is a brain cell. In particular embodiments, the cell is a neuron. In certain embodiments, cell expresses an NMDA receptor. In particular embodiments, the cell expresses an ionotropic Glutamate receptor. In some embodiments, the cell expresses a voltage-gated sodium channel. In certain embodiments, the cell has experienced an increase in internal sodium ion ($Na^+$) concentration. In some embodiments, the cell has experienced an increase in internal chloride ion ($Cl^-$) concentration. In particular embodiments, the cell has experienced a depolarization. In some embodiments, the cell is swollen. In certain embodiments, the inhibitor of SLC26A11 reduces SLC26A11 activity. In particular embodiments, wherein the SLC26A11 activity is $Cl^-$ import. In some embodiments, the inhibitor of SLC26A11 reduces the level of SLC26A11 expression in the cell. In some embodiments, the cell death is apoptosis. In certain embodiments, the cell death is necrosis.

Particular embodiments are directed to a method for reducing swelling of a cell, comprising contacting the cell with an inhibitor of SLC26A11. In certain embodiments, the cell is a brain cell. In particular embodiments, the cell is a neuron. In certain embodiments, cell expresses an NMDA receptor. In particular embodiments, the cell expresses an ionotropic Glutamate receptor. In some embodiments, the cell expresses a voltage-gated sodium channel. In certain embodiments, the cell has experienced an increase in internal sodium ion (Na+) concentration. In some embodiments, the cell has experienced an increase in internal chloride ion (Cl–) concentration. In particular embodiments, the cell has experienced a depolarization. In some embodiments, the cell is swollen. In certain embodiments, the inhibitor of SLC26A11 reduces SLC26A11 activity. In particular embodiments, wherein the SLC26A11 activity is Cl– import. In some embodiments, the inhibitor of SLC26A11 reduces the level of SLC26A11 expression in the cell.

Certain embodiments are directed to a method for reducing internal $Cl^-$ concentration in a cell, comprising contacting the cell with an inhibitor of SLC26A11. In certain embodiments, the cell is a brain cell. In particular embodiments the cell is a neuron. In certain embodiments, the cell expresses an NMDA receptor. In some embodiments, the cell expresses an ionotropic Glutamate receptor. In certain embodiments the cell expresses a voltage-gated sodium channel. In particular embodiments, the cell has experienced an increase in internal $Na^+$ concentration. In some embodiments, the cell has experienced a depolarization. In certain the cell is swollen. In particular embodiments, the inhibitor of SLC26A11 reduces SLC26A11 activity. In certain embodiments, the SLC26A11 activity is $Cl^-$ import. In some embodiments, the inhibitor of SLC26A11 reduces the level of SLC26A11 expression in the cell.

Particular embodiments are directed to a method of treating brain edema in a subject comprising administering an inhibitor of SLC26A11 to the subject. In some embodiments, brain edema is cytotoxic brain edema. In certain embodiments, the brain edema is focal brain edema. In particular embodiments, the brain edema is global brain edema. In some embodiments, the subject has traumatic brain injury, brain surgery, ischemic stroke, brain hemorrhage, brain inflammation, meningitis, encephalitis, Reye's Syndrome, infection, migraine, a tumor, a brain tumor, poisoning, severe acute mountain sickness, high altitude cerebral edema, or brain hypoxia resulting in edema. In some embodiments, the inhibitor of SLC26A11 is administered orally, nasally, intravenously, intramuscularly, ocularly, transdermally, intracranially, intrathecally, or subcutaneously. In certain embodiments, the inhibitor of SLC26A11 is a natural or chemically modified polypeptide, an antibody, a natural or chemically modified small oligopeptide, a natural, unnatural, or chemically modified amino acid, a polynucleotide, a natural or chemically modified oligonucleotide, RNAi, shRNA, siRNA, a small nucleotide, a natural or chemically modified mononucleotide, a lipopeptide, an antimicrobial, a small molecule, or a pharmaceutical molecule.

Certain embodiments are directed to a method of reducing brain tissue swelling comprising administering an inhibitor of SLC26A11 to injured brain tissue. In some embodiments, the brain tissue swelling is cytotoxic brain edema. In certain embodiments, the brain edema is focal brain edema. In some embodiments, the brain edema is global brain edema. In certain embodiments, the subject has traumatic brain injury, brain surgery, ischemic stroke, brain hemorrhage, brain inflammation, meningitis, encephalitis, Reye's Syndrome, infection, migraine, a tumor, a brain tumor, poisoning, severe acute mountain sickness, high altitude cerebral edema, or brain hypoxia resulting in edema. In some embodiments, the inhibitor or SLC26A11 is administered orally, nasally, intravenously, intramuscularly, ocularly, transdermally, intracranially, intrathecally, or subcutaneously. In some embodiments, the inhibitor of SLC26A11 is a natural or chemically modified polypeptide, an antibody, a natural or chemically modified small oligopeptide, a natural, unnatural, or chemically modified amino acid, a polynucleotide, a natural or chemically modified oligonucleotide, RNAi, shRNA, siRNA, a small nucleotide, a natural or chemically modified mononucleotide, a lipopeptide, an antimicrobial, a small molecule, or a pharmaceutical molecule.

Particular embodiments are directed to a method of preventing brain edema in a subject at risk of developing brain edema from an injury or an illness, comprising administering an inhibitor of SLC26A11 to the subject. In some embodiments, the brain tissue swelling is cytotoxic brain edema. In certain embodiments, the brain edema is focal brain edema. In some embodiments, the brain edema is global brain edema. In certain embodiments, the subject has traumatic brain injury, brain surgery, ischemic stroke, brain hemorrhage, brain inflammation, meningitis, encephalitis, Reye's Syndrome, infection, migraine, a tumor, a brain tumor, poisoning, severe acute mountain sickness, high altitude cerebral edema, or brain hypoxia resulting in edema. In some embodiments, the inhibitor or SLC26A11 is administered orally, nasally, intravenously, intramuscularly, ocularly, transdermally, intracranially, intrathecally, or subcutaneously. In some embodiments, the inhibitor of SLC26A11 is a natural or chemically modified polypeptide, an antibody, a natural or chemically modified small oligopeptide, a natural, unnatural, or chemically modified amino acid, a polynucleotide, a natural or chemically modified oligonucleotide, RNAi, shRNA, siRNA, a small nucleotide, a natural or chemically modified mononucleotide, a lipopeptide, an antimicrobial, a small molecule, or a pharmaceutical molecule.

Certain embodiments are directed to a method of treating a disease or condition associated with abnormal chloride ion regulation of brain cells in a subject, comprising administering an inhibitor of SLC26A11 to the subject. In some embodiments, the subject has neonatal seizures, epilepsy, temporal lobe epilepsy, epilepsy resulting from hypoxic-ischemic insult, epilepsy resulting from head trauma, or mesial temporal sclerosis. In certain embodiments, the inhibitor or SLC26A11 is administered orally, nasally, intravenously, intramuscularly, ocularly, transdermally, intracranially, intrathecally, or subcutaneously. In some embodiments, the inhibitor of SLC26A11 is a natural or chemically modified polypeptide, an antibody, a natural or chemically modified small oligopeptide, a natural, unnatural, or chemically modified amino acid, a polynucleotide, a natural or chemically modified oligonucleotide, RNAi, shRNA, siRNA, a small nucleotide, a natural or chemically modified mononucleotide, a lipopeptide, an antimicrobial, a small molecule, or a pharmaceutical molecule.

Certain embodiments are directed to a method of determining if a candidate agent inhibits SLC26A11, comprising: stimulating intake of $Cl^-$ in at least one cell of a brain section; contacting the brain section with the candidate agent; taking a first measurement of a property of the brain section; and comparing the measurement to a first reference standard and a second reference standard; wherein the first reference standard comprises at least one measurement of the property in a brain section not stimulated for $Cl^-$ intake in a second at least one cell; wherein the second reference standard comprises at least one measurement of the property in a brain section stimulated for $Cl^-$ intake in a third at least one cell; wherein the brain sections of the first and second references are not contacted with the candidate agent; and wherein a difference between the first measurement and the second reference standard and a lack of a difference between the first measurement and the first reference standard indicates that the candidate agent is an SLC26A11 inhibitor.

In some embodiments, the brain section contains at least one brain region selected from the list consisting of cortex, hippocampus, striatum, cerebellum, brain stem, and spinal cord. In certain embodiments the brain section contains hippocampus. In some embodiments, the brain section comprises neurons and glia. In particular embodiments, the at least one cell is a neuron. In some embodiments, the at the least one cell expresses an NMDA receptor. In particular the at least one cell expresses an ionotropic Glutamate receptor. In certain embodiments, the at least one cell expresses a voltage-gated sodium channel. In some embodiments, stimulating intake of Cl– in at least one cell of a brain section comprises stimulating intake of $Na^+$ in the at least one cell of the brain section, thereby stimulating intake of $Cl^-$ in the at least one cell of the brain section.

In certain embodiments, a method of determining if a candidate agent inhibits SLC26A11 comprises stimulating the intake of $Na^+$ in the at least one cell of the brain section comprises contacting the brain section with an agent that simulates intake of $Na^+$. In some embodiments, the agent is a voltage-gated sodium channel agonist. In particular embodiments, the voltage-gated sodium channel agonist is veratridine. In some embodiments, the brain section is further contacted with an NMDA receptor inhibitor. In particular embodiments, the NMDA receptor inhibitor is AP5. In certain embodiments, the agent is an ionotropic glutamate receptor agonist. In certain embodiments, the agent is an AMPA/kainate receptor agonist. In some embodiments, the AMPA/kainate receptor agonist at least one of Glutamate, AMPA, 5-Fluorowillardiine, Domoic acid, Quisqualic acid, Aniracetam, Cyclothiazide, CX-516, CX-546, CX-614, derivative 11r, CX-691, CX-717, IDRA-21, Org 26576, LY-392,098. LY-404,187, LY-451,395, LY-451,646, LY-503,430, Oxiracetam, PEPA, Piracetam, Pramiracetam, Sunifiram, Unifiram, 5-lodowillardiine, ATPA, Domoic acid, Kainic acid, LY-339,434, or SYM-2081. In particular embodiments, the ionotropic glutamate receptor agonist is an NMDA receptor agonist. In some embodiments, the NMDA receptor agonist is NMDA. In certain embodiments, the brain section is further contacted with a voltage-gated sodium channel inhibitor. In some embodiments, the voltage-gated sodium channel inhibitor is TTX. In particular embodiments, the brain section is further contacted with at least one calcium channel blocker. In some embodiments, the calcium channel blocker is a cadmium ion ($Cd^{2+}$). In particular embodiments, the brain section is further contacted with at least one AMPA/kainate receptor antagonist. In some embodiments, the at least one AMPA/kainite receptor antagonist is CNQX. In some embodiments, the brain section is further contacted with at least one GABA receptor antagonist. In particular embodiments, the at least one GABA receptor antagonist is picrotoxin. In some embodiments, the brain section is further contacted with $Cd^{2+}$, CNQX, and picrotoxin.

In certain embodiments, a method of determining if a candidate agent inhibits SLC26A11 comprises stimulating the intake of $Na^+$ in the at least one cell of the brain section by depolarizing the at cell. In some embodiments, depolarizing the cell comprises contacting the medium with KCl. In particular embodiments, depolarizing the cell comprises contacting the at least one cell with an agent that triggers depolarization. In some embodiments, the agent is selected from the list consisting of: an excitatory neurotransmitter, an excitatory neurotransmitter receptor agonist, an excitatory amino acid transporter inhibitor (EAATI), glutamate, dopamine, norepinephrine, epinephrine, acetylcholine, cAMP agonists, and calcium channel agonists. In certain embodiments, depolarizing the cell comprises providing electrophysiological stimulation. In particular embodiments, electrophyiological stimulation is provided by an extracellular electrode. In some embodiments, the electrophysiological stimulation is provided by in intracellular electrode, optionally by patch-clamp technique. In certain embodiments, the cell expresses an optogenetic actuator, and wherein depolarizing the cell comprises stimulating the optogenetic actuator in the cell with optical stimulation.

Particular embodiments are directed to a method of determining if a candidate agent inhibits SLC26A11, wherein the candidate agent is a natural or chemically modified polypeptide, an antibody, a natural or chemically modified small oligopeptide, a natural, unnatural, or chemically modified amino acid, a polynucleotide, a natural or chemically modified oligonucleotide, RNAi, shRNA, siRNA, a small nucleotide, a natural or chemically modified mononucleotide, a lipopeptide, an antimicrobial, a small molecule, or a pharmaceutical molecule.

Certain embodiments are directed to a method of determining if a candidate agent inhibits SLC26A11, comprising: stimulating intake of Cl– in at least one cell of a brain section; contacting the brain section with the candidate agent; taking a first measurement of a property of the brain section; and comparing the measurement to a first reference standard and a second reference standard; wherein the property is swelling. In some embodiments, measuring swelling comprises: measuring size of the at least one cell and comparing it to a measurement of size of the at least one cell before $Cl^-$ intake was stimulated; thereby taking a measurement of swelling of the at least one cell. In certain embodiments, astrocytes are visualized with sulforhodamine101 (SR101). In particular embodiments, the at least one cell is visualized with CoroNaGreen. In particular embodiments, the at least one cell is visualized with sodium-binding benzofuran isophthalate (SBFI).

In some embodiments, the at least one cell is contacted with an intracellular fluorescent dye; and wherein taking a first measurement of swelling of the brain section comprises: measuring fluorescent intensity of the intracellular fluorescent dye of the at least one cell and comparing it to a measurement of fluorescent intensity of the intracellular fluorescent dye of the at least one cell before $Cl^-$ intake was stimulated; thereby taking a measurement of swelling of the at least one cell. In some embodiments, the at least one cell is visualized with CoroNaGreen, SBFI or Calcein red-AM. In particular embodiments, taking a first measurement of a property of the brain section comprises: measuring light transmittance through the at least one cell and comparing it to a measurement of light transmittance through the at least one cell before Cl– intake was stimulated; thereby taking a measurement of swelling of the at least one cell; wherein an increase in light transmittance through the cell indicates cellular swelling. In certain embodiments, the measurements are performed with fluorescence microscopy or two photon fluorescence lifetime imaging (FILM).

Certain embodiments are directed to a method of determining if a candidate agent inhibits SLC26A11, comprising: stimulating intake of Cl– in at least one cell of a brain section; contacting the brain section with the candidate agent; taking a first measurement of a property of the brain section; and comparing the measurement to a first reference standard and a second reference standard; wherein the property is internal $Cl^-$ concentration. In some embodiments, the at least one cell is visualized with MQAE. In particular embodiments, the first measurement is performed with fluorescence microscopy or FILM.

Certain embodiments are directed to a method of determining if a candidate agent inhibits SLC26A11, comprising: stimulating intake of Cl– in at least one cell of a brain section; contacting the brain section with the candidate agent; taking a first measurement of a property of the brain section; and comparing the measurement to a first reference standard and a second reference standard; wherein the property is cell death, wherein the cell death is necrosis or apoptosis. In some embodiments, the cell death is measured with an LDH assay, TUNEL staining, MTT assay, quantification of ATP consumption, caspase activation assay, nuclear morphology assay, quantification of DNA strand breaks, or quantification of a vital dye.

Some embodiments are directed to a method of determining if a candidate agent inhibits SLC26A11, comprising: (a) stimulating channel activity of SLC26A11; (b) contacting the cell with the candidate agent; (c) taking a measurement of a property of the cell; and (d) comparing the measurement to a first reference standard and a second reference standard; wherein the property is internal Cl– concentration, or Cl– channel conductance, wherein the first reference standard comprises at least one measurement of the property in a brain section not stimulated for SLC26A11 channel activity in a second at least one cell; wherein the second reference standard comprises at least one measurement of the property in a brain section stimulated for SLC26A11 channel activity in a third at least one cell; wherein the brain sections of the first and second references are not contacted with the candidate agent; and wherein a difference between the first measurement and the second reference standard and a lack of a difference between the first measurement and the first reference standard indicates that the candidate agent is an SLC26A11 inhibitor. In some embodiments, the cell is a HEK cell. In particular embodiments, the SLC26A11 is human SLC26A11.

Some embodiments are directed to a method of determining if a candidate agent inhibits SLC26A11, wherein the candidate agent is a natural or chemically modified polypeptide, an antibody, a natural or chemically modified small oligopeptide, a natural, unnatural, or chemically modified amino acid, a polynucleotide, a natural or chemically modified oligonucleotide, RNAi, shRNA, siRNA, a small nucleotide, a natural or chemically modified mononucleotide, a lipopeptide, an antimicrobial, a small molecule, or a pharmaceutical molecule.

In some embodiments, step (a) comprises depolarizing the cell; thereby activating SLC26A11. In certain embodiments, depolarizing the cell comprises contacting the cell with a medium containing KCl. In some embodiments, depolarizing the cell comprises contacting the at least one cell with an agent that triggers depolarization. In some embodiments, depolarizing the cell comprises providing electrophysiological stimulation. In some embodiments, electrophyiological stimulation is provided by an extracellular electrode. In particular embodiments, the electrophysiological stimulation is provided by in intracellular electrode. In some embodiments, the cell expresses an optogenetic actuator, and wherein depolarizing the cell comprises optical stimulation.

In certain embodiments, step (a) comprises contacting the cell with an agent that stimulates the intake of $Na^+$, thereby activating SLC26A11. In some embodiments, the agent is a voltage-gated sodium channel agonist. In particular embodiments, the voltage-gated sodium channel agonist is veratridine.

Some embodiments are directed to a method of determining if a candidate agent inhibits SLC26A11, wherein steps (a)-(c) are performed with patch clamp electrophysiology. In some embodiments, step (a) comprises applying an applied potential difference; thereby stimulating SLC26A11 channel activity. In some embodiments, step (c) comprises taking a measurement of channel conductance; thereby taking a measurement of a property of the cell.

Some embodiments are directed to a method of determining if a candidate agent inhibits SLC26A11, wherein steps (a) (c) are performed with a colorimetry technique, wherein the cell is contacted with a medium containing iodine ions ($I^-$). In some embodiments, step (c) comprises the steps of: (i) removing the cell from the medium containing $I^-$; (ii) lysing the cell, thereby obtaining a cell lysate; (iii) contacting the cell lysate with $Ce^{4+}$ and $As^{3+}$; (iv) detecting the color of the lysate whereby the color of the lysate indicates internal $I^-$ concentration, and whereby the internal I-concentration indicates Cl– conductance of cell.

Some embodiments are directed to a method of determining if a candidate agent inhibits SLC26A11, wherein steps (a) (c) are performed with a pH detection assay, wherein the cell is contacted with a medium with a pH below 7.4. In some embodiments, step (c) comprises measuring extracellular pH, wherein a decrease in extracellular pH indicates Cl– channel activity. In certain embodiments, the medium contains a fluorescent pH sensitive dye. In particular embodiments, the fluorescent pH sensitive dye is 2',7'bis-(2-carboxyethyl)-5-(and 6)-carboxyfluorescein (BCECF).

Some embodiments are directed to a method of determining if a candidate agent inhibits SLC26A11, wherein the cell is contacted with a voltage sensitive fluorescent dye. In certain embodiments, the voltage sensitive fluorescent dye is FLIPR fluorescent membrane potential dye. In some embodiments, step (c) comprises measuring the fluorescence signal of the voltage sensitive dye, thereby measuring the conductance of the channel.

Some embodiments are directed to a method of determining if a candidate agent inhibits SLC26A11, wherein the cell is contacted with a FRET detector that can detect negative membrane potentials, wherein the FRET detector comprises a donor and an acceptor. In some embodiments, the donor is CC2-DMPE and the acceptor is DiBac2, wherein the FRET detector produces a fluorescent signal with the membrane potential of the cell is negative, and wherein the fluorescent signal is weakened when the cell is depolarized.

Some embodiments are directed to a method of determining if a candidate agent inhibits SLC26A11, wherein the cell is contacted with a YFP molecule that is quenched by small anions. In some embodiments, the YFP molecule comprises a I152L mutation. In particular embodiments, the YFP molecule comprises a V163S mutation. In some embodiments, step (c) comprises measuring fluorescence signal of the YFP molecule, thereby measuring conductance of the channel.

BRIEF DESCRIPTION OF THE FIGURES

FIG. 2 shows NMDAR activation triggers neuronal swelling that requires $Na^+$ influx, but that is independent of $Ca^{2+}$ influx. (A and B) $Na^+$ influx triggers an increase in neuronal volume, measured as the cross sectional area in the absence of extracellular $Ca^{2+}$ (0 mM $Ca^{2+}$, 2 mM EGTA) (n=5). (C and D) Iso-osmotic replacement of extracellular $Na^+$ with NMDG (from 152 mM to 26 mM), to reduce $Na^+$ entry through NMDARs prevents neurons from swelling and causes them to shrink (86.7% of baseline, p<0.05) (n=4). Scale bars, 15 µm (B and D). Shaded area above and below mean represent SEM.

DETAILED DESCRIPTION

Figure 1B:
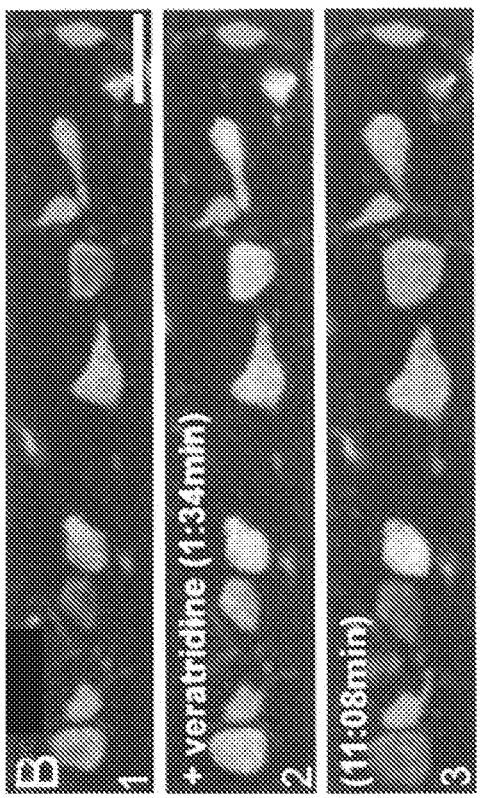
FIG. 1 shows that neuronal swelling is caused by prolonged increases in intracellular $Na^+$ and is independent of $Ca^{2+}$. (A) CoroNa Green ($Na^+$ indicator) loaded neurons versus SR101 stained astrocytes in a hippocampal brain slice imaged using two-photon laser scanning microscopy. (B-D) Cortical neurons treated with veratridine (50 µM) show increase in $[Na^+]i$ followed by swelling (increase in cross sectional area). Astrocytes do not swell. (E and F) CoroNaFLIM measurements of $[Na^+]i$ as neurons swell reveals true time course and magnitude of $Na^+$ signals that are independent of dye concentration (n=4). (G-I) Calibration of FLIM measurements of neuronal $[Na^+]i$ with CoroNa. (G) Decay of CoroNa fluorescence changes in salt solutions with varying $[Na^+]$. (H) Dual (simultaneous) whole cell patch-clamping of 2 neurons dialyzed with high (109 mM) and low (9 mM) $[Na^+]i$ show distinct separation of lifetimes. (I) Calibration of CoroNa lifetimes measured in soma of neurons dialyzed with different $[Na^-]$ shows that the $[Na^+]i$ can be predicted from T fast. (J and K) Quantified data shows neuronal swelling is triggered by sodium influx via independent pathways. NMDAR-mediated swelling was dependent on $Na^+$ influx and independent of $Ca^{2+}$. VER, veratridine; x-sectional, cross sectional; VGSC, voltage gated sodium channel; SR101, sulforhodamine 101. Scale bars, 20 µm (B), 15 µm (H).

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below. All of the patent and non-patent literature references listed herein are incorporated by reference in their entireties.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the ε-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "biological sample" includes a biological material that can be collected from a subject and used in connection with diagnosis or monitoring of biological states. Biological samples can include clinical samples, including body fluid samples, such as body cavity fluids, urinary fluids, cerebrospinal fluids, blood, and other liquid samples of biological origin; and tissue samples, such as biopsy samples, tumor or suspected tumor samples, and other solid samples of biological origin. Biological samples can also include those that are manipulated in some way after their collection, such as by treatment with reagents, culturing, solubilization, enrichment for certain biological constituents, cultures or cells derived therefrom, and the progeny thereof.

The term "conjugate" includes an entity formed as a result of covalent or non-covalent attachment or linkage of an agent or other molecule, e.g., a detectable entity, a biologically active molecule, PEG or other polymer, to an antibody described herein.

A "control" such as a "control subject" or "control tissue" includes a healthy subject or a healthy tissue sample, for example, which is not pathological or diseased. In certain embodiments, a control includes a non-diseased tissue from a different, healthy subject or the same subject being tested or diagnosed. A control can also include a reference standard, for example, a standard value generated from one or more healthy subjects or tissues.

As used herein, the terms "function" and "functional" and the like refer to a biological, enzymatic, or therapeutic function.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

"Homology" refers to the percentage number of amino acids that are identical or constitute conservative substitutions. Homology may be determined using sequence comparison programs such as GAP (Deveraux et al., Nucleic Acids Research. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances. In particular embodiments, the isolated polypeptide is an antibody.

A "decreased" or "reduced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) relative to a control. Other examples of comparisons and "statistically significant" amounts are described herein. "Decrease," as used herein, can refer to "inhibit," "reduce," "curb," "abate," "diminish," "lessen," "lower," or "weaken."

A "increased" or "enhanced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase. An increased or enhanced amount may also include a 2 fold, 3 fold, 4 fold, 5 fold, 6 fold, 7 fold, 8 fold, 9 fold, 10 fold, 20-fold, 30 fold, 40 fold, 50 fold, 60 fold 70 fold, 80 fold, 90 fold, 100 fold, 200 fold, 300 fold, 400 fold, 500 fold, 1,000 fold, 10,000 fold, or greater than 10,000 fold increase (including all integers and ranges in between) relative to a control. Other examples of comparisons and "statistically significant" amounts are described herein. "Increase," as used herein, can refer to "agonize," "enhance," "inflate," "escalate," expand," "augment," "enlarge," or "raise."

"Destabilization" as used herein, refers to reducing the half life of the functional form of a biological or pharmaceutical entity. Destabilization may be achieved, for example, by increasing the probability the entity will be degraded, or by decreasing the probability that the entity will be in an active confirmation or state.

In certain embodiments, the "purity" of any given agent (e.g., a pharmaceutical compound) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example, and by no means limiting, by high performance liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example, disclosed by Altschul et al., Nucl. Acids Res. 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

A "subject," as used herein, includes any animal that exhibits a symptom or condition, or is at risk for or suspected of exhibiting a symptom or condition, which can be diagnosed with an antibody described herein. Suitable subjects (patients) include laboratory animals (such as mouse, rat, rabbit, or guinea pig), farm animals, and domestic animals or pets (such as a cat or dog). Non-human primates and, preferably, human patients, are included.

A "subject subpopulation" or "patient subpopulation," as used herein, includes a subject or patient subset characterized as having one or more distinctive measurable and/or identifiable characteristics that distinguishes the subject or patient subset from others in the broader disease category (e.g., cancer) to which it belongs. Such characteristics include disease subcategories, gender, lifestyle, health history, organs/tissues involved, treatment history, etc. In some embodiments, a patient or subject subpopulation is characterized by the (e.g., reduced) amount or levels of an SLC26A11 polypeptide in a biological sample, for example, a tumor sample.

"Substantially" or "essentially" means nearly totally or completely, for instance, 80%, 85%, 90%, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild-type gene or gene product (e.g., a polypeptide) is that which is most frequently observed in a population and is thus arbitrarily designed the "normal" or "wild-type" form of the gene.

The term "firing" refers to the generation of one or more action potentials. "Neuron firing activity," as used herein, refers to the amount, frequency, and/or characteristics of action potentials generated by a neuron.

SLC26A11

The solute linked carrier 26 (SLC26) family of proteins is composed of functionally important anion transport proteins. In humans, the family has at least ten known members. Members of this family of proteins are essential for numerous cellular functions including homeostasis and intracellular electrolyte balance.

The SLC26A11 gene encodes a member of the SLC26 family of anion exchangers. SLC26A11 is also known as "Solute Carrier Family 26 (Anion Exchanger), Member 11", "Solute Carrier Family 26, Member 11," and "Sodium-Independent Sulfate Anion Transporter." SLC26A11 was originally identified as a sulfate transporter, but has been shown to operate in several modes, including as an exchanger for $Cl^-$, $SO_4^{2-}$, $HCO_3^-$ or $H^+$—$Cl^-$ or as a $Cl^-$ channel, depending upon the tissue type and the expression system.

In certain embodiments of the current invention, SLC26A11 is a functional $Cl^-$ influx pathway in brain cells. Particular embodiments contemplate, but are not bound by, a mechanism linking $Na^+$ influx and SLC26A11 mediated $Cl^-$ influx by membrane depolarization activating SLC26A11 in its $Cl^-$ channel mode, thereby leading to a sustained $Cl^-$ influx.

In certain embodiments, an inhibitor of SLC26A11 reduces SLC26A11 activity. In particular embodiments, an inhibitor of SLC26A11 reduces SLC26A11 activity by a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between). In particular embodiments, an inhibitor of SLC26A11 reduces SLC26A11 activity by a "statistically significant" amount. Determination if a reduction of activity is "statistically significant" can be made by employing standard methods in the art. A statistically significant reduction can refer to SLC26A11 activity in the presence of an inhibitor compared to a reference standard. Reference standards may include, but are not limited to, SLC26A11 activity before the SLC26A11 polypeptide is contacted with the inhibitor, an SLC26A11 polypeptide that is contacted with a vehicle control or a control agent that is structurally similar to the SLC26A11 polypeptide but lacks biological activity, or a reference standard generated by any other methods commonly employed in the art.

Particular embodiments contemplate, but are not bound by, SLC26A11 functioning as a $Cl^-$ channel, where activity of SLC26A11 refers to the $Cl^-$ conductance of SLC26A11. In such embodiments, "closed" refers to a conformation of the SLC26A11 where there is little or no $Cl^-$ conductance. Under certain physiological conditions, such as elevated internal $Na^+$ concentration or neuronal depolarizations of −20 mV, SLC26A11 adopts an open conformation which allows for $Cl^-$ conductance. "Open" refers to a conformation where Cl– ions are permitted to pass through the channel. In some embodiments, SLC26A11 can have one or more open and closed conformations. In some embodiments, the invention is directed to an agent that binds to or interacts with SLC26A11 and reduces its activity. This effect may be achieved by, for example but not limited to, changing the probability that the SLC26A11 channel will be in an open or closed conformation, changing the conditions, such as the internal cation concentration, that changes the conformation of the channel, changing the duration of time that SLC26A11 remains in an open or closed state, changing the $Cl^-$ conductance of SLC26A11 when it is in an open or closed state, or any combination thereof. In some embodiments, inhibiting activity of an SLC26A11 is achieved by reducing the probability that the channel will adopt an open conformation, changing the conditions (such as the threshold membrane potential following depolarization of a neuron), decreasing the duration of time the channel remains in an open conformation, reducing the $Cl^-$ conductance of the channel when it is in an open conformation, or any combination thereof.

In certain embodiments, the invention is directed to an inhibitor of SLC26A11 that reduces SLC26A11 expression. Expression refers to the level or amount of functional SLC26A11. Reduction in the expression of SLC26A11 can be achieved, for example but not limited to, preventing transcription of the SLC26A11 gene, reducing the amount of SLC26A11 mRNA, reducing the transcription of SLC26A11, destabilizing SLC26A11 mRNA, destabilizing the SLC26A11 polypeptide, increasing degradation of SLC26A11 mRNA, increasing the degradation of SLC26A11 polypeptide, preventing or reducing the presence of SLC26A11 at the cellular membrane, or any other manipulation that results in a reduced amount of functional SLC26A11. In particular embodiments, an inhibitor of SLC26A11 reduces SLC26A11 expression by a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between). In particular embodiments, the invention is drawn to an inhibitor of SLC26A11 that reduces SLC26A11 activity by a "statistically significant" amount.

In some embodiments, SLC26A11 is mammalian SLC26A11. In certain embodiments, SLC26A11 is human SLC26A11. In particular embodiments, SLC26A11 is rodent SCL26A11. In certain embodiments, SLC26A11 is mouse SLC26A11. In certain embodiments, SLC26A11 is rat SLC26A11. In particular embodiments, SLC26A11 refers to an SLC26A11 polypeptide, as well as subsequences, fragments, variants (including but not limited to variants resulting from alterative splicing), or derivatives thereof.

The primary amino acid sequence of human, rat, and mouse SLC26A11 are shown in Table 1 below. Of note, mRNAs encoding SLC26A11 have splice variants that can result in different isoforms of the polypeptide. Therefore, the amino acid sequences listed in table 1 are exemplary, and the current invention contemplates the use of the splice varients and isoforms thereof.

TABLE 1

SLC26A11 Polypeptides

| Name | Gene Symbol | Amino Acid Sequence | SEQ ID NO: |
|---|---|---|---|
| Human SLC26A11 | SLC26A11 | MPSSVTALGQARSSGPGMAPSACCCSPAALQRRLPILAWLPSYSLQWLKMDFVAG LSVGLTAIPQALAYAEVAGLPPQYGLYSAFMGCFVYFFLGTSRDVTLGPTAIMSL LVSFYTFHEPAYAVLLAFLSGCTQLAMGVLRLGFLLDFISYPVIKGFTSAAAVTI GFGQIKNLLGLQNIPRPFFLQVYHTFLRIAETRVGDAVLGLVCMLLLLVLKLMRD HVPPVHPEMPPGVRLSRGLVWAATTARNALVVSFAALVAYSFEVTGYQPFILTGE TAEGLPPVRIPPFSVTTANGTISFTEMVQDMGAGLAVVPLMGLLESIAVAKAFAS QNNYRIDANQELLAIGLTNMLGSLVSSYPVTGSFGRTAVNAQSGVCTPAGGLVTG VLVLLSLDYLTSLFYYIPKSALAAVIIMAVAPLFDTKIFRTLWRVKRLDLLPLCV TFLLCFWEVQYGILAGALVSLLMLLHSAARPETKVSEGPVLVLQPASGLSFPAME ALREEILSRALEVSPPRCLVLECTHVCSIDYTVVLGLGELLQDFQKQGVALAFVG LQVPVLRVLLSADLKGFQYFSTLEEAEKHLRQEPGTQPYNIREDSILDQKVALLK A | 1 |
| Rat SLC26A11 variant X4 | SLC26A11 | MAPDTHCCSRADLRRRLPVLAWLPNYSLRWLRMDVIAGLSVGLTVIPQALAYAEV AGLPPQYGLYSAFMGCFVYFVLGTSRDVTLGPTAIMSLLVSFYTFREPAYAVLLA FLSGCTQLAMGLLHLGFLLDFISCPVIKGFTSAASITIGFGQVKNLLGLQNIPRQ FFLQVYHTFLHIGETRVGDAILGLVCMVLLLVLKLMREHIPPPHPEMPLGVKFSR GLVWTVTTARNALVVSFAALIAYAFEVTGSHPFILTGKIAQGLPPVRMPPFSVTT DNKTISFSEMVQVSGCRASSMAEAERLHCPFSLASQNNYRIDANQELLAIGLTNV LGSLVSSYPVTGSFGRTAVNAQTGVCTPAGGLVTGVLVLLSLDYLTLLFYYIPKS ALAAVIIMAVAPLFDVKIFRRLWLVQRLDLLPLCVTFLLSFWEIQYGILAGTLVS LLILLHSVARPKTQVSEGQILVLQPASGLHFPAVDALREAMTKRALEASPPRSAV LECTHVSNIDYTVILGLGELLEDFQKKGVTLAFVGLQVPVLRTLLAADLKGFQYF TTLEEAEKSLQQEPGTQPYSIREDTAPEHRSSLLKSPSGP | 2 |
| Mouse SLC26A11 | SLC26A11 | MAPDTCCCSATALRRRLPVLAWVPDYSLQWLRLDFIAGLSVGLTVIPQALAYAEV AGLPPQYGLYSAFMGCFVYFFLGTSRDVTLGPTAIMSLLVSFYTFLGTSRDVTLGPTAIMSLLVSFYTFREPAYAVLLA FLSGCTQLAMGLLHLGFLLDFISCPVIKGFTSAASITIGFGQIKNLLGLQKIPRQ FFLQVYHTFLHIGETRVGDAVLGLASMLLLLVLKCMREHMPPPHPEMPLAVKFSR GLVWTVTTARNALVVSSAALIAYAFEVTGSHPFVLTGKIAEGLPPVRIPPFSVTR DNKTISFSEMVQDMGAGLAVVPLMGLLESIAVAKSFASQNNYRIDANQELLAIGL TNVLGSLVSSYPVTAVTPLFDVKIFRSLWRVQRLDLLPLCVTFLLSFWEIQYGILAGS PKSALAAVIITAVTPLFDVKIFRSLWRVQRLDLLPLCVTFLLSFWEIQYGILAGS LVSLLILLHSVARPKTQVSEGQIFVLQPASGLYFPAIDALREAITNRALEASPPR SAVLECTHISSVDYTVIVGLGELLEDFQKKGVALAFVGLQVPVLRTLLAADLKGF RYFTTLERAEKFLQQEPGTEPNSIHEDAVPEQRSSLLKSPSGP | 3 |

The exemplary mRNA sequences of human, rat, and mouse SLC26A11 are shown in Table 2 below. Of note, mRNAs encoding SLC26A11 have splice variants that can result in different isoforms of the polypeptide. Therefore, the amino acid sequences listed in table 2 are exemplary. In some embodiments, the invention contemplates the use of splice variants and isoforms.

TABLE 1

SLC26A11 mRNA

| Name | Gene Symbol | Amino Acid Sequence | SEQ ID NO: |
|---|---|---|---|
| Human SLC26A11 | SLC26A11 | acgtgcgcgccagacccgccccggcctgtccccggcgattcctgcggacccagc tgcggcgacgccaggagaccccaagctgcatcgccgagtggaagcaactagaact ccaggggctgtgaaagccacaggtggggctgagcgaggcgtggcctcaggagcgg aggaccccccactctccctcgagcgccgcagtccaccgtagcgggtggagcccg ccttggtgcgcagttggaaaacctcggagcccgctggatctcctggctgccacc cgcaccccccgccagcctacgccccaccgtagagatgccttcttcggtgacggcg ctgggtcaggccaggtcctctggccccgggatggccccgagcgcctgctgctgct ccctgcgggccctgcagaggaggctgcccatcctggcgtggctgcccagctactc cctgcagtggctgaagatggattttcgtcgccggcctctcagttggcctcactgcc attccccaggcgctggcctatgctgaagtggctggactcccgcccagtatggcc tctactctgccttcatgggctgcttcgtgtatttcttcctgggcacctcccggga tgtgactctgggccccaccgccattatgtccctcctggtctccttctacaccttc catgagcccgcctacgctgctgctggccttcctgtccggctgcatccagctgg ccatgggggtcctgcgtttgggttcctgctggacttcatttcctacccgtcat taaaggcttcacctctgctgctgccgtcaccatcggctttggacagatcaagaac ctgctgggactacagaacatcccccaggccgttcttcctgcaggtgtaccacacct tcctcaggattgcagagaccagggtaggtgacgccgtcctggggctggtctgcat gctgctgctgctggtgctgaagctgatgcgggaccacgtgcctcccgtccacccc | 4 |

TABLE 1 -continued

SLC26A11 mRNA

| Name | Gene Symbol | Amino Acid Sequence | SEQ ID NO: |
|---|---|---|---|
| | | gagatgcccctggtgtgcggctcagccgtgggctggtctgggctgccacgacag<br>ctcgcaacgccctggtggtctcttcgcagccctggttgcgtactccttcgaggt<br>gactggataccagcctttcatcctaacaggggagacagctgaggggctccctcca<br>gtccggatcccgcccttctcagtgaccacagccaacgggacgatctccttcaccg<br>agatggtgcaggacatgggagccgggctggccgtggtgcccctgatgggcctcct<br>ggagagcattgcggtggccaaagccttcgcatctcagaataattaccgcatcgat<br>gccaaccaggagctgctggccatcggtctcaccaacatgttgggctccctcgtct<br>cctcctacccggtcacaggcagctttggacggacagccgtgaacgctcagtcggg<br>ggtgtgcaccccggcgggggcctggtgacgggagtgctggtgctgctgtctctg<br>gactacctgacctcactgttctactacatcccaagtctgccctggctgccgtca<br>tcatcatggccgtggccccgctgttcgacaccaagatcttcaggacgctctggcg<br>tgttaagaggctggacctgctgcccctgtgcgtgaccttcctgctgtgcttctgg<br>gaggtgcagtacggcatcctggccggggccctggtgtctctgctcatgctcctgc<br>actctgcagccaggcctgagaccaaggtgtcagaggggccggttctggtcctgca<br>gccggccagcggcctgtccttccctgccatggaggctctgcgggaggagatccta<br>agccgggccctggaagtgtccccgccacgctgcctggtcctggagtgcacccatg<br>tctgcagcatcgactacactgtggtgctgggactcggcgagctcctccaggactt<br>ccagaagcagggcgtcgccctggccttgtgggcctgcaggtccccgttctccgt<br>gtcctgctgtccgctgacctgaaggggttccagtacttctctaccctggaagaag<br>cagagaagcacctgaggcaggagccagggaccagccctacaacatcagagaaga<br>ctccattctggaccaaaaggttgccctgctcaaggcataatggggccaccgtgg<br>gcatccacagtttgcagggtgttccggaaggttcttgtcactgtgattggatgct<br>ggatgccgcctgatagacatgctggcctggctgagaaacccctgagcaggtaacc<br>cagggaagagaaggaagccaggcctggaggtccacggcagtgggagtggggctca<br>ctggcttcctgtgggatgactggaaaatgacctcgctgctgttccctggcatgac<br>cctctttggaagagtggtttggagagagccttctagaatgacagactgtgcgagg<br>aagcaggggcaggggtttccagcccgggctgtgcgaggcatcctggggctggcag<br>caccttcccggctcaccagtgccacctgcggggagggacggggcaggcaggagt<br>ctgggaggcgggtccgctcctcttgtctgcggcatctgtgctctccgagagaaaa<br>ccaaggtgtgtcaaatgacgtcaagtctctatttaaaaataattttgtgttttct<br>aaatgaaaaagtgatagctttggtgattttgtaaaagtcataaatgcttattgt<br>aaaaaatacaggaaaccacccctcaccctgtccacttgggtgatcattccagacc<br>cctcccaaacatgcatatgtacctgtccgtcagtgtgtggatgtatgtttacag<br>ttctacataaatgggatcattttatacatggtgctctggaaccacatttttcat<br>gcagtcatttgcagtgaattatttattgtgataataaatagcattagaatacaag<br>attttaaaaaaaaa | |
| Rat SLC26A11 variant X4 | SLC26A11 | atgtactgcccactctgttcctgagattcctgaggactcagctacggccacttcg<br>gaggaccccgagcctcggcgttcggtggctttgtaaaaggtctgggtcaggccag<br>atcccccagcctgatcatggcaccagacacacactgctgctccagggcagacct<br>gaggaggaggctacccgtcctggctggctgcccaactactctctgcggtggctg<br>agaatggacgtcatcgctggactctccgtgggtctcaccgtcatccccaggccc<br>tggcctatgcagaagtggctggactcccgcccagtacggtctctactctgccttt<br>catggggtgcttcgtgtacttcgtcctgggcacctccgggatgtgactctgggc<br>cccacggctatcatgtctctcctggtatcctactacaccttccgtgagcctgcct<br>atgccgtgctgcttgccttcctgtctgggtgtatccagttggccatggggctcct<br>gcatttggggttcctgctggacttcatctcctgccctgtcattaaaggcttcaca<br>tccgctgccagcatcacaattggctttggacaggtcaagaacctgctgggattac<br>agaacatcccccggcagttcttcctccaggtgtaccacaccttcctccacatcgg<br>agagaccagggtgggcgatgccatcctgggactggtctgcatggtgctgctgctt<br>gtgctgaagcttatgcgtgaacacattcctcctcccatcctgagatgcccccttg<br>gcgtgaagttcagccgtgggctagtgtggaccgtcacaacagctcgcaacgcctt<br>ggtggtctccttcgcggccctgattgcttacgccttcgaggtgacaggatcccat<br>ccgttcattctgactggaaagatcgcccaggggctccctcctgtgaggatgccgc<br>ccttctcagtgaccacagacaataagaccatctctttctctgagatggtgcagga<br>catgggggtcggactggctgtggtgcctctgatgggcctcctggagaccattgct<br>gtggccaaatccttcgcctcccagaataattaccgcattgatgccaaccaggagc<br>tgctggccatcggcctcaccaatgtgctgggctccctagtctcgtcttacccggt<br>cactggcagctttggcggacagcagtgaatgcccagacggggtgtgtaccccg<br>gcaggaggctggtgactggtgtcctggtgctgctgtctctggactacctgacct<br>tactgttctactatatcccaagtctgcactggctgccgtcatcatcatggctgt<br>ggccccgctctttgacgtcaagatcttcaggaggctctggcttgttcagagtacg<br>taccgcaaagcaggcagctctggggtgacatctgggaatgcctaggcctttgtta<br>tccctcctggcctgtgggctggagctgtggcactctggtaaacttaggagaagat<br>acactggaggtggctgcttagcgagcgaagctggacttcggtccacacagagctg<br>gacagagctctgtagcttgagtggagaacagagtttcccactcggtgtcctc<br>atcctctcctcccccatctttctcttcctgaggggtggtgacagaaaggcctc<br>acacaatagtctctcagtctcccccatctcccgccctgagagccctcatccact<br>ggtttcttaacaaatcagaggttaacttttcctccttcctcgttgtccagttgt<br>cgggtgtgtgtcccagctttctgtgtaccaggtttcatcttaggacagcttga<br>gatatatcagtgtagatgtgtggaactgatgttctccaaggaaactaggactcca<br>gaaagggcatggcctgtcaggttgccacatcagaggtacaatctcagactgagt<br>ccaagtactttgtgcccagggcaataaatcctcctggtctcctggagtcacaaga<br>cacaccacacacgcaccat | 5 |

TABLE 1 -continued

SLC26A11 mRNA

| Name | Gene Symbol | Amino Acid Sequence | SEQ ID NO: |
|---|---|---|---|
| Mouse SLC26A11 | SLC26A11 | atgtcctgcccactctgtttctgagattcctgcggactcagctaccgccacttcg gaagaccctgagtctcagcgtccgctctgtgaaaggtctgggtcagaccagatcc cccagcctgcacatggcaccagacacatgctgctgctctgctacggccctgagga ggaggctacccgtcctggcctgggtgcctgactactctctgcagtggctgaggct ggacttcatcgctggactttccgtgggactcaccgtcattcccaggccctggcc tatgcagaagtggctggactccacccagtacggcctctactctgccttcatgg gatgcttcgtgtatttcttcctgggcacctcccgggatgtgactctgggccccac ggctatcatgtctctcctggtgtccttctacaccttccgtgagcctgcctatgct gtgctgcttgccttcctgtctgggtgtatccagctggccatggggctcctgcatt tggggttcctgctggacttcatctcctgccctgtcattaaaggcttcacctccgc tgccagcatcacaattggctttggacagatcaagaacctgctgggattgcagaaa atcccccggcagttcttcctccaggtgtaccacaccttcctccacatcggagaga ccagggtaggcgacgctgtcctcggactggcctccatgttgctgctgcttgtgct gaagtgtatgcgggaacacatgcctcctccccatcctgagatgcccttgccgtg aagttcagccgtgggctggtgtggactgtcacaacagctcgcaatgccctggtgg tctcctccgcggctctgattgcttacgccttcgaggtgacaggatcccatcctt tgttctgactggaaagatcgccgaggggctccctccggtgcggatcccacccttc tcagtgaccagggacaataagaccatctcgttctctgagatggtgcaggacatgg gggccggactggctgtggtacctctgatggggctcctggagagcattgccgtggc caaatccttcgcgtctcagaataactaccgcattgatgctaaccaggaactactg gccattggcctcaccaatgtgctgggctccctcgtctcctcttaccagtcactg gcagctttgggcggacagctgtgaatgcccagacaggggtgtgtaccccggcagg aggcctggtgactggtgccctggtgctgctgtccctgaactacttgacctcactc ttctcctatatccccaagtctgccctggctgccgtgatcatcacggctgtgaccc cactctttgatgtcaagatcttcaggagtctctggcgcgttcagaggctggatct gctaccactgtgtgtgacgttcctgctgtccttctgggagatccagtacggtatc ctggccggtagcctggtgtctttgctcattctcctgcactcggtagctaggccca agactcaggtgtcagaaggacaaattttttgttcttcagccggccagcggcctgta cttccctgcaattgatgccctccgagaggcaataacgaaccgggcactggaagca tccccaccacgttccgcggttctggagtgcacgcatatcagcagtgtagactaca ccgtgatcgtgggactcggtgagctcctggaggacttccagaagaaaggagtcgc cctggcctttgttggcctacaggtgcccgtgctccgcacactgttggccgctgac ctcaagggttccgttacttcaccactctggaggaggctgagaaattcctgcagc aggaaccaggaactgagcccaacagcatccatgaagatgctgttccagagcaaag gagctccctgctcaagtctccctccggcccctgaagagcagatggtataggaagg gtttctgaaggttctgtcaccatgacttggagtcacctgatagactcaccaacc tggtgggacttaaaaggcactgcataggtggctctggggaacagcagggagccat gtatgatttccagggtgtcacttttcctgctgtcccctaggtgtgagtatttgagg gctgggctgactgaaaagtcttcagagagagagagagagagacagagacccaga gacacacacatggcttctggcctggtctggcagggtaaggtgacactctccagat cccagattcttctttggaatcaggtcctactggagaaaaatcaaagagattgggc atctcggagatgtgtctgaccatgtcatgaagtctaatctgagctgaagaggtgg ccacagcatgccacacaaggtcaattctgtttaaaatcatgtgttttttaaatgg aagtcactctggtgtttttgtaaagcaaaacaaaaacatttatgcttactttaaa aaaaaaatccaagaactcatgcatcctgttcactattctcttaactgaggtcccc tgcccggacaggtgtgtatccgtcagtgtgtgcacacggtgccgtctgatgtgaa gacccgaatcactgtattaaggtgctttgtaaactgtcttcatgcagtcattaat tgtgaattatttattgtgatgatcaatgacattaaatgcaagatttatttaccttattaaaatacaagatttatttattgtattaaaatacaatattctgtgggtcc | 6 |

Methods of Use

Embodiments include methods relating to the use of SLC26A11 inhibitors. Particular embodiments are directed to methods of ameliorating cell death by contacting cells with an inhibitor of SLC26A11. Cell death is an event whereby a cell permanently ceases to perform its functions. Cell death results from the natural process of old cells being replaced by new ones, or from factors such as disease, injury, or death of the organism. Types of cell death include programed cell death which is mediated by an intracellular active, regulated process and includes apoptosis (also known as Type I cell death) and authophagic cell death (also known as macroauthophagic cell death or Type II cell death). Apoptosis is the process of programmed cell death whereby biochemical events lead to characteristic morpholocial changes and death. These changes include blebbing, cell shrinkage, nuclear fragmentation, chromatin condensation, and chromosomal DNA fragmentation. Autophagic cell death is a catabolic process that results in the autophagosomic-lysosomal degradation of bulk cytoplasmic contents, abnormal protein aggregates, and excess or damaged organelles.

In contrast to programmed cell death, necrosis is a form of cell injury that results in the premature death of cells in living tissue by autolysis. Necrosis is caused by factors external to the cell or tissue, such as infection, toxins, or trauma that result in the unregulated digestion of cell components. In contrast to programmed cell death, necrosis is not a controlled, regulated process. Cells that die due to necrosis do not follow a specific signal transduction pathway as in the case of programmed cell death, but rather various receptors are activated that result in the loss of cell membrane integrity and an uncontrolled release of cellular products into the extracellular space. This can trigger an inflammatory response in surrounding tissue.

In particular embodiments, an inhibitor of SLC26A11 contacts a cell and ameliorates cell death. Ameliorating cell death refers to reducing the probability or likelihood of death in the cell. When referring to more than one cell, for example more than one cell found in a tissue, ameliorating cell death can be used to mean reducing the amount of cells that undergo cell death. In some embodiments, an inhibitor of SCL26A11 contacts a cell and ameliorates necrosis. In some embodiments, an inhibitor of SCL26A11 contacts a cell and ameliorates programmed cell death. In some embodiments, an inhibitor of SCL26A11 contacts a cell and ameliorates apoptosis. In some embodiments, an inhibitor of SCL26A11 contacts a cell and prevents autophagic cell death. In some embodiments, an inhibitor of SLC26A11 contacts cells and reduces cell death by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In certain embodiments, an inhibitor of SLC26A11 contacts cells and reduces programmed cell death by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In particular embodiments, an inhibitor of SLC26A11 contacts cells and reduces apoptosis by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In certain embodiments, an inhibitor of SLC26A11 contacts cells and reduces necrosis by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In particular embodiments, the amelioration of cell death is statistically significant.

In some embodiments, the cell is a brain cell. In some embodiments, the cell is a neuron. In some embodiments, the cell is an excitatory neuron. In some embodiments, the cell an inhibitory neuron. In certain embodiments, the neuron expresses at least one ionotropic glutamate receptor. In particular embodiments, the ionotropic glutamate receptor is an AMPA receptor, a kainate receptor, and/or an NMDA receptor. In particular embodiments, the cell has experienced a depolarization. In some embodiments, the neuron expresses at least one NMDA receptor. In some embodiments, the neuron expresses at least one voltage-gated sodium channel. In some embodiments, the cell is a neuron of the central nervous system. In some embodiments, the cell is a glial cell, such as an astrocyte, oligodendrocyte, microglial cell, or an ependymal cell.

Some embodiments are directed to a model whereby permissive $Cl^-$ influx into a cell through activity of SLC26A11 leads to increased levels of internal Cr. Without being bound by theory, prolonged elevation of internal $Cl^-$ concentration causes water to enter the cell through osmotic pressure which results in cellular swelling, which in turn can lead to cell death. An inhibitor of SLC26A11 reduces $Cl^-$ influx and/or reduces internal $Cl^-$ concentration and thereby reduces water intake, which in turn reduces cellular swelling and ameliorates subsequent cell death. Thus, in some embodiments an inhibitor of SLC26A11 contacts cells and ameliorates cell death by reducing $Cl^-$ intake. In some embodiments, an inhibitor of SLC26A11 contacts cells that are swollen and ameliorates cell death. In some embodiments, an inhibitor of SLC26A11 contacts cells that have an elevated internal $Cl^-$ concentration and ameliorates cell death.

In particular embodiments, cellular swelling, also termed cellular edema, is defined as increased cell volume. This increase can be relative to the typical volume of the cell, relative to the mean volume of cells of the same type, relative to the median volume of cells of the same type, or a volume of the cell before an event, such as a cellular insult, that triggers an increase in cell volume. In some embodiments, swelling is defined as a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase in cell volume (including all integers and ranges in between). Swelling may also include a 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or 1000-fold increase of cellular volume (including all integers and ranges in between). In some embodiments, the swelling is statistically significant. In some embodiments, an inhibitor of SLC26A11 contacts a swollen cell and reduces swelling. In some embodiments, an inhibitor of SLC26A11 contacts a cell with an elevated internal concentration of $Cl^-$ and reduces cell swelling. In some embodiments, an inhibitor of SLC26A11 contacts a cell with an elevated internal concentration of $Na^+$ and reduces cell swelling. In some embodiment, an inhibitor of SLC26A11 contacts a cell and prevents or slows swelling.

In certain embodiments, elevated or increased internal $Cl^-$ concentration is relative to the typical internal $Cl^-$ concentration of the cell, relative to the mean internal $Cl^-$ concentration of cells of the same type, relative to the median internal $Cl^-$ concentration of cells of the same type, or an internal $Cl^-$ concentration of the cell before an event, such as a cellular insult, that triggered an increase in cell volume. In some embodiments, an increase of internal $Cl^-$ concentration is defined as a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase in internal $Cl^-$ concentration (including all integers and ranges in between). An increase of internal $Cl^-$ concentration may also include a 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or 1000-fold increase in $Cl^-$ concentration (including all integers and ranges in between). In some embodiments, an increase in $Cl^-$ concentration is an increase of about 1 mM, 2 mM, 3 mM, 4 mM, 5 mM, 6 mM, 7 mM, 8 mM, 9 mM, 10 mM, 15 mM, 20 mM, 30 mM, 40 mM, 50 mM, 60 mM, 70 mM, 80 mM, 90 mM, 100 mM, 200 mM, 300 mM, 400 mM, 500 mM, 600 mM, 700 mM, 800 mM, 900 mM, 1 M, 2 M, 3 M, 4 M, 5 M, 6 M, 7 M, 8 M, 9 M, 10 M (including all integers and ranges in between). In certain embodiments, the elevated or increased $Cl^-$ concentration is statistically significant.

Certain embodiments are directed to a model whereby a typical neuron in the CNS has an internal resting $Cl^-$ concentration of about 0 mM to about 40 mM. Therefore, in these embodiments, a neuron would be considered to have elevated internal $Cl^-$ concentration if the internal $Cl^-$ concentration was measured at 41 mM, 42 mM, 43 mM, 44 mM, 45 mM, 46 mM, 47 mM, 48 mM, 49 mM, 50 mM, 55 mM, 60 mM, 65 mM, 70 mM, 75 mM, 80 mM, 85 mM, 90 mM, 100 mM, 110 mM, 120 mM, 130 mM, 140 mM, 150 mM, 200 mM, 300 mM, 400 mM, 500 mM, 600 mM, 700 mM, 800 mM, 900 mM, 1 M, 2 M, 3 M, 4 M, 5 M, 6 M, 7 M, 8 M, 9 M, 10 M (including all integers and ranges in between).

In some embodiments, an inhibitor of SLC26A11 contacts a cell with an elevated internal $Cl^-$ concentration and reduces internal Cl⁻ concentration. In some embodiments, an inhibitor of SLC26A11 contacts a swollen cell and reduces internal Cl⁻ concentration. In some embodiments, an inhibitor of SLC26A11 contacts a cell with an elevated internal concentration of Na⁺ and reduces internal Cl⁻ concentration. In some embodiments, an inhibitor of SLC26A11 contacts a cell and prevents or slows an increase of internal Cl⁻ concentration.

Particular embodiments are directed to a model whereby cellular events that lead to sustained, elevated concentrations of cations, including Na⁺, trigger cell death that is dependent on SLC26A11 activity. Without being bound by theory, sustained buildup of intracellular cations results in an electrochemical gradient that favors Cl⁻ import. SLC26A11 permits pathological Cl⁻ intake, leading to events that trigger cell death. Some embodiments contemplate that cellular insult, such as hypoxia, trigger SLC26A11-dependent cell death. Hypoxia can trigger cell death in part by reducing or depleting cellular energy stores. Since internal concentrations of cations are maintained with active transport, hypoxia disrupts this regulation, resulting in sustained elevated internal concentrations of Na⁺. In neurons, a similar breakdown of ionic gradients occurs during pathological settings of cytotoxic edema, such as excitotoxicity or ischemia, when activation of voltage-gated and ligand-gated channels leads to massive increases in internal concentrations of Na⁺, followed by increases in extracellular K⁺ and almost complete depolarization of the neurons. In some embodiments, an inhibitor of SCL26A11 contacts cells with elevated internal Na⁺ concentration and ameliorates cell death.

In certain embodiments, elevated or increased internal Na⁺ concentration is relative to the typical internal Na⁺ concentration of the cell, relative to the mean internal Cl⁻ concentration of cells of the same type, relative to the median internal Na⁺ concentration of cells of the same type, or a internal Na⁺ concentration of the cell before an event, such as a cellular insult, that triggered an increase in cell volume. In some embodiments, an increase of internal Na⁺ concentration is defined as a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase in cell volume (including all integers and ranges in between). An increase of internal Na⁺ concentration may also include a 2-fold, 3-fold, 4-fold, 5-fold, 6-fold, 7-fold, 8-fold, 9-fold, or 10-fold increase in cell volume (including all integers and ranges in between). In some embodiments, an increase in Na⁺ concentration is an increase of about 1 mM, 2 mM, 3 mM, 4 mM, 5 mM, 6 mM, 7 mM, 8 mM, 9 mM, 10 mM, 15 mM, 20 mM, 30 mM, 40 mM, 50 mM, 60 mM, 70 mM, 80 mM, 90 mM, 100 mM, 200 mM, 300 mM, 400 mM, 500 mM, 600 mM, 700 mM, 800 mM, 900 mM, 1 M, 2 M, 3 M, 4 M, 5 M, 6 M, 7 M, 8 M, 9 M, 10 M (including all integers and ranges in between). In certain embodiments, the increase of internal Na⁺ concentration is statistically significant.

Certain embodiments are directed to a model whereby a typical neuron in the CNS has an internal resting Na⁺ concentration of about 1 mM to about 10 mM. Therefore, in these embodiments, a neuron would be considered to have an elevated internal Na⁺ concentration if the resting internal Na⁺ concentration was measured at 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 100 mM, 110 mM, 120 mM, 130 mM, 140 mM, 150 mM, 200 mM, 300 mM, 400 mM, 500 mM, 600 mM, 700 mM, 800 mM, 900 mM, 1 M, 2 M, 3 M, 4 M, 5 M, 6 M, 7 M, 8 M, 9 M, 10 M (including all integers and ranges in between).

In some embodiments, an inhibitor of SLC26A11 contacts a cell with an elevated internal Na⁺ concentration and reduces internal Cl⁻ concentration. In some embodiments, an inhibitor of SLC26A11 contacts a with elevated internal Na⁺ concentration and reduces cell swelling. In some embodiments, an inhibitor of SLC26A11 contacts a cell with an elevated internal concentration of Na⁺ prevents or slows an increase of internal Cl⁻ concentration and/or cellular swelling.

In some embodiments, an SLC26A11 inhibitor contacts cells and ameliorates cell death and/or reduces swelling that is due, at least in part, to abnormal levels of internal Na⁺ concentration. In some embodiments, an SLC26A11 inhibitor contacts cells and ameliorates cell death and/or reduces cellular swelling that is due, at least in part, to abnormal levels of internal Cl⁻ concentration. Abnormal internal concentrations of Na⁺ or Cl⁻ can result from, for example but limited to, cellular insults such as disruptions between neuron and astrocyte interactions, abnormal neurotransmitter signaling, including but not limited to, abnormal extracellular levels of glutamate, GABA, glycine, acetylcholine, dopamine, serotonin, norepinephrine, peptide neurotransmitters, or any combination thereof. Abnormal concentrations of Na⁺ and/or Cl⁻ can also result from depletion of energy sources to the cell, for example, reduced supply of glucose or oxygen, or reduced intracellular levels of ATP. Proper maintenance of internal and external ion concentrations of a cell require ATP-dependent processes. Lack of cellular energy disrupts these processes and can generate elevated internal Na⁺ and Cl⁻ concentrations.

Depolarization may also trigger abnormal levels of internal Na⁺ and Cr. Normal depolarizations occur in neurons in the form of action potentials, however, abnormal increases in ion concentrations can result when neurons experience altered or abnormally rapid pulses of action potenials. Such activity can result in increased internal ion levels that overwhelm the cell's ability to restore ion levels to that of the normal resting concentrations. This can occur, for example, during a seizure. Abnormal internal concentrations of Na⁺ and Cl⁻ can result from excitotoxic events such as an epileptic seizure, stroke, hypoxia, or any combination thereof. Abnormal internal concentrations of Na⁺ and Cl⁻ can also result from a pathological condition caused by a disease. Such diseases include, but are not limited to, neurodegenerative diseases such as Alzheimer's disease, Parkinson's disease, amyotrophic lateral sclerosis (ALS), frontotemporal dementia and parkinsonism linked to chromosome 17 (FTDP-17), polyglutamine diseases, Huntington's disease, spinocerebellar ataxia, and corticobasal degeneration.

In some embodiments, an inhibitor of SLC26A11 contacts a cell that has experienced a depolarization. In some embodiments, the cell that has experienced a depolarization is a cell that has experienced an action potential. In neurons, action potentials play the central role for cell-to-cell communication. An action potential is a short-lasting event in which the electrical membrane potential of a cell rapidly rises and falls, following a consistent trajectory. Action potentials are generated by voltage-gated sodium channels at the membrane. These channels are closed when the membrane potential is near the resting potential, but they rapidly begin to open if the membrane potential increases to a precisely defined threshold value. When the channels open (in response to depolarization in transmembrane voltage), they allow an inward flow of sodium ions, which changes the electrochemical gradient, which in turn produces a further rise in the membrane potential. This then causes more channels to open, producing a greater electric current across the cell membrane. The process proceeds until all of the available ion channels are open, resulting in a large upswing in the membrane potential. The rapid influx of sodium ions causes the polarity of the plasma membrane to reverse, and the ion channels then rapidly inactivate. As the sodium channels close, sodium ions can no longer enter the neuron, and then they are actively transported back out of the plasma membrane. In some embodiments, a cell that has experienced a depolarization is a neuron. In some embodiments, an inhibitor of SLC26A11 contacts a neuron that has experienced one or more action potentials.

In some embodiments, an inhibitor of SLC26A11 contacts a cell that has experienced a depolarization wherein the cell is a neuron and wherein the depolarization was action potentials in rapid succession. In some embodiments, a neuron that experienced depolarization is a neuron that has experienced action potentials in rapid succession, wherein the rapid succession of action potentials leads to a persistent increase in internal $Na^+$ concentration. In some embodiments, the rapid succession of action potentials are of a pathological nature, for example the neuronal firing activity seen during a seizure or neuronal neuronal firing associated with excitotoxicity, such as excitotoxicity following an ischemic or hypoxic event.

In some embodiments, an inhibitor of SLC26A11 contacts a cell that has experienced a depolarization, wherein the cell is a neuron that has experienced an excitotoxic event. In some embodiments, an inhibitor of SLC26A11 contacts a cell that has experienced a depolarization that is at risk of excitotoxicity. Particular embodiments are directed to a model whereby excitotoxicity is the pathological process by which nerve cells are damaged or killed by excessive stimulation by neurotransmitters such as glutamate. This occurs when ionotropic glutamate receptors are over-activated by excess extracellular glutamate. Excess activation allows high levels of $Ca^{2+}$ and $Na^+$ to enter the cell. Excitotoxic damage is caused in part by the excess $Ca^{2+}$ influx that activates phospholipases, endonucleases, and proteases such as calpain that go on to damage the cytoskeleton, organelles, membrane, and DNA. Excitotoxic damage is also caused in part by prolonged depolarization and/or prolonged elevation of $Na^+$ levels that can increase internal $Cl^-$ concentration, trigger cellular swelling, and/or lead to cell death. Excitotoxicity is implicated in damage, for example but not limited to, resulting from spinal cord injury, stroke, traumatic brain injury, hearing loss (through noise overexposure or toxicity) and in neurodegenerative diseases of the central nervous system including Alzheimer's disease, amyotrophic lateral sclerosis (ALS), Parkinson's disease, Huntington's, alcoholism or alcohol withdrawal, and rapid benzodiazepine withdrawal. In some embodiments, an inhibitor of SLC26A11 contacts a cell that has experienced a depolarization as a result of a pathological condition. In some embodiments, depolarization is excitotoxic. In some embodiments, an inhibitor of SLC26A11 contacts a cell that has experienced a depolarization to reduce or prevent excitotoxicity.

In some embodiments, an inhibitor of SLC26A11 contacts a cell to ameliorate or reduce NMDA receptor-dependent cell death. Particular embodiments are directed to a model whereby prolonged NMDA receptor activity contributes to cell death resulting from excitotoxicty in neurons. Without being bound by theory, NMDA receptor-dependent toxicity has been attributed sustained $Ca^{2+}$ influx, which under the conditions of excitotoxicity, triggers a signaling cascade that leads to neuronal apoptosis. Particular embodiments contemplate a model whereby NMDA receptor-dependent toxicity can also result from a previously unrecognized mechanism (see Examples) of $Ca^{2+}$-independent NMDA receptor-dependent cell death. NMDA receptors opened by excitotoxic insults permit $Ca^{2+}$ and $Na^+$ intake into neurons. Experiments described herein have identified a mechanism whereby $Na^+$ that enters through NMDA receptors triggers cell death. Applications of NMDA receptor agonist resulted in elevated internal concentrations of $Na^+$ ions in neurons, which in turn triggered an influx of $Cl^-$, cellular swelling, and cell death. In some embodiments, Nat dependent NMDA receptor-dependent cell death is reduced or ameliorated by contacting cells with an SLC26A11 inhibitor. In some embodiments, NMDA receptor-dependent cellular swelling is reduced by contacting cells with an SLC26A11 inhibitor. In some embodiments, $Cl^-$ influx resulting from prolonged opening of NMDA receptors is reduced by contacting cells with an SLC26A11 inhibitor.

In some embodiments, an SLC26A11 inhibitor contacts a cell to reduce cellular swelling. In certain embodiments, an inhibitor of SLC26A11 contacts cells and reduces swelling by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In some embodiments, the reduction in cellular swelling is statistically significant.

In some embodiments, an SLC26A11 inhibitor contacts a cell to reduce internal $Cl^-$ concentration. In certain embodiments, an inhibitor of SLC26A11 contacts cells and reduces internal $Cl^-$ concentration by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In some embodiments, an inhibitor of SLC26A11 contacts a cell and reduces internal $Cl^-$ concentration by 1 mM, 2 mM, 3 mM, 4 mM, 5 mM, 6 mM, 7 mM, 8 mM, 9 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 300 mM, 400 mM, 500 mM, 600 mM, 700 mM, 800 mM, 900 mM, 1 M, 2 M, 3 M, 4 M, 5 M, 6 M, 7 M, 8 M, 9 M, 10 M (including all integers and ranges in between). In some embodiments, the reduction of internal $Cl^-$ concentration is statistically significant.

In particular embodiments, an inhibitor of SLC26A11 is administered to a subject to treat brain edema. In some embodiments, the brain edema is cytotoxic brain edema. In some embodiments, the edema is vasogenic edema. In some embodiments, the brain edema is focal brain edema. In some embodiments, the brain edema is global brain edema. In some embodiments, an inhibitor of SLC26A11 is administered to a subject to amielorate brain cell death. In some embodiments, the inhibitor of SLC26A11 is administered to a subject to reduce swelling of brain cells. In some embodiments, the inhibitor of SLC26A11 is administered to the subject to reduce internal $Cl^-$ concentration of brain cells. In some embodiments, an inhibitor of SLC26A11 is administered to a subject with cytotoxic brain edema to reduce or prevent vasogenic brain edema.

In certain embodiments, an inhibitor of SLC26A11 is administered to injured brain tissue to reduce or prevent brain tissue swelling. In some embodiments, the brain tissue swelling is cytotoxic brain edema. In some embodiments, the brain edema is focal brain edema. In some embodiments, the brain edema is global brain edema. In some embodiments, an inhibitor of SLC26A11 is administered to a brain tissue to amielorate brain cell death. In some embodiments, the inhibitor of SLC26A11 is administered to brain tissue to reduce swelling of brain cells. In some embodiments, the inhibitor of SLC26A11 is administered to brain tissue to reduce internal Cl⁻ concentration of brain cells. In some embodiments, an inhibitor of SLC26A11 is administered to an injured brain tissue with cytotoxic edema to reduce or prevent vasogenic brain edema.

In some embodiments, an inhibitor of SLC26A11 is administered to a subject with an injury or illness to prevent brain edema. In some embodiments, an inhibitor of SLC26A11 is administered to a subject with an injury or an illness to prevent cytotoxic brain edema. In some embodiments, an inhibitor of SLC26A11 is administered to a subject with an injury or an illness to amielorate brain cell death. In some embodiments, the inhibitor of SLC26A11 is administered to a subject with an injury or an illness to reduce swelling of brain cells. In some embodiments, the inhibitor of SLC26A11 is administered to the subject to reduce internal Cl⁻ concentration of brain cells.

Injured brain tissue refers to brain tissue that has been damaged as a result of a disease, disorder, condition, or traumatic injury. Injured brain tissue can lead to edema, as a result of, for example but not limited to, excessive permeability of the blood brain barrier, disruption of cellular metabolism, dysregulation of cellular electrochemical gradient, or a combination thereof. Diseases, disorders, conditions or injuries associated with edema include, but are not limited to: infarction, for example, cerebral artery infarction or brain infarction; injury, for example, brain injury, head injury, spinal cord injury, traumatic brain injury, traumatic head injury or traumatic spinal cord injury; trauma, for example, head trauma, cerebral trauma or spinal cord trauma; cerebral venous thrombosis; intracerebral hemorrhage; ischemia, for example, brain ischemia, hemorrhagic ischemia or cerebral ischemia; acute disseminated encephalitis (ADEM); stroke, for example, ischemic stroke; tumors, for example, brain tumor or spinal cord tumor; brain infection; brain abscess; surgery; post-surgical manipulation; sepsis; hypertension; respiratory insufficiency; poisoning, for example, CO poisoning, tin poisoning, lead poisoning or arsenical poisoning; hyponatremia; acute nephropathy; hepatic encephalopathy; disequilibrium syndrome caused by hemodialysis; hyperglycemia; hypoglycemia; adrenal insufficiency; collagen diseases; blood-central nervous system barrier dysfunction; or optical diseases, for example, diabetic retinopathy. Diseases, disorders, conditions, or injuries associated with cytotoxic edema include, but are not limited to: intracerebral hemorrhage, cerebral contusion, cerebral infarction, brain tumor, stroke, drug-induced lung injury, drug-induced pulmonary disease, anthrax toxicity, hepatic encephalopathy, influenza encephalopathy, intracranial hypertension, hepatic failure, hepatic encephalopathy, nephrotic syndrome, diabetes, sarcoidosis, high altitude, and altitude sickness.

Malignant brain edema can occur during neurosurgical surgery, generating a life-threatening emergency. Open brain herniation is more commonly seen during intracranial procedures being conducted for head injury, as compared to elective neurosurgical operations. In the case of the latter, brain edema may be due to subarachnoid haemorrhage (SAH) secondary to aneurysm rupture or intraventricular haemorrhage during resection of brain tumors. The brain may suddenly swell uncontrollably and inexplicably, so that the surgical procedure may have to be abandoned due to lack of access to the intracranial operating site. In some embodiments, an inhibitor of SLC26A11 is administered to a subject to treat or prevent brain edema resulting from or occurring during neurosurgery.

An ischemic stroke, sometimes referred to as a cerebrovascular accident, or cerebrovascular insult, is the loss of brain function due to a disturbance in the blood supply to the brain. This disturbance is due to either ischemia (lack of blood flow) or hemorrhage. Stroke, as the third leading cause of death, affects more than 700,000 people in the United States each year. A major unmet medical need is treatment of edema associated with stroke. The extent of brain edema is a major determinant of patient survival after a stroke event. For progressive edema due to middle cerebral artery occlusion, mortality approaches 80%. The propensity of ischemic brain tissue to develop edema remains the major cause of death in patients with large infarctions, particularly within the middle cerebral artery territory and cerebellum involved in 15-20% of all strokes. Clinically acceptable strategies for management of ischemic brain edema have remained elusive, and available treatments are often of limited value for patients with massive edema. Cytotoxic edema correlates with initial infarct size, and vasogenic edema contributes to the delayed risk-prone processes of brain swelling. In some embodiments, an inhibitor of SLC26A11 is administered to a subject who has had an ischemic stroke to treat brain edema. In some embodiments, the brain edema is cytoxic brain edema. In some embodiments, the brain edema is vasogenic brain edema.

Encephalitis is inflammation of the brain tissue which can lead to brain edema. Most cases of encephalitis are caused by viral infections, but in rare cases it can also be caused by bacteria. There are two main types of encephalitis, primary and secondary. Primary encephalitis is when a virus directly infects the brain and spinal cord. Secondary encephalitis is when an infection that starts elsewhere and travels to the brain. The most common virus that causes encephalitis is herpes simplex. Usually the herpes virus travels via a nerve to the skin, but in rare cases, the virus travels to the brain. This form of encephalitis will often affect the temporal lobe—the part of the brain that controls memory and speech. It can also affect the frontal lobe—which affects emotions and behavior. Herpes encephalitis can cause severe and long lasting damage, in part, through the generation of brain edema. Other viral infections that can lead to encephalitis and brain edema include, but are not limited to, the mumps virus, Epstein-Barr virus, HIV, cytomegalovirus, California encephalitis, West Nile Virus, Colorado encephalitis, Eastern Equine encephalitis, Kyasanur forest disease. In some embodiments, an inhibitor of SLC26A11 is administered to a subject with a viral infection to treat or prevent brain edema. In some embodiments, an inhibitor of SLC26A11 is administered to a subject with encephalitis to treat or prevent brain edema.

Reye syndrome or Reye's syndrome is a potentially fatal syndrome that has numerous detrimental effects to many organs, especially the brain and liver. Reye's syndrome occurs almost exclusively in children. The classic features are a rash, vomiting, and liver damage. The exact cause is unknown and, while it has been associated with aspirin consumption by children with viral illness, it also occurs in the absence of aspirin use. The serious symptoms of Reye's syndrome appear to result from damage to cellular mitochondria, at least in the liver, and there are a number of ways that aspirin could cause or exacerbate mitochondrial damage. Cytotoxic edema in seen in the brain of patients with Reye's syndrome. In some embodiments, an inhibitor of SLC26A11 is administered to a subject for the treatment of Reye's syndrome.

Edema associated with brain tumors plays a major role in determining symptoms caused by cerebral tumors. Not only does edema cause additional mass effect, often exceeding the mass induced by the tumor itself and resulting in increased intracranial pressure, it also leads to neurological disturbances by disrupting tissue homeostasis and reducing local blood flow. Brain tumors are most often associated with vasogenic edema, with the primary disturbance at the level of the microvasculature. The tight junctions that form the blood brain barrier protect the brain's interstitial space from plasma extravasation under normal conditions, as there is no lymphatic system within the brain. In tumors, morphologically disrupted tight junctions in newly formed brain tumor capillaries lack sufficient molecular composition to form functioning tight junctions. This breakdown of the blood brain barrier increases vascular permeability. Under normal conditions, the ventricles and subarachnoid cerebrospinal fluid allow steady circulation and replenishment of the extracellular space. This process is overwhelmed in when the brain vasculature becomes too permeable, resulting in extracellular fluid accumulation and vascular edema. In certain embodiments, an inhibitor of SLC26A11 is administered to a subject with a brain tumor for the treatment of brain edema.

Severe Acute Mountain Sickness is caused by reduced air pressure and lower oxygen levels at high altitudes. It can caused by traveling to a high altitude, and the risk increases with the speed of the ascent. Symptoms of mild or moderate acute mountain sickness can include difficulty sleeping, dizziness, fatigue, headache, nausea, rapid pulse, and shortness of breath. More severe cases can cause confusion, cyanosis, chest tightness or congestion, difficulty of movement. Severe cases can also lead to complications such as cerebral edema, which can be signaled by persistent headache, unsteady gait, gradual loss of consciousness, and retinal hemorrhage. In some embodiments, an inhibitor of SLC26A11 is administered to a subject for the treatment of Severe Acute Mountain Sickness.

High altitude cerebral edema is a medical condition in which the brain swells with fluid because of the physiological effects of traveling to a high altitude. It generally appears in patients who have acute mountain sickness and involves disorientation, lethargy, and nausea among other symptoms. It occurs when the body fails to acclimatize while ascending to a high altitude. It appears to be a vasogenic edema, fluid penetration of the blood-brain barrier, although cytotoxic edema is thought to occur as well. Individuals with the condition must immediately descend to a lower altitude or coma and death can occur. Patients are usually given supplemental oxygen and dexamethasone as well. If left untreated, patients can die within 48 hours, and those who receive treatment often take days or weeks to fully recover. In some embodiments, an inhibitor of SLC26A11 is administered to a subject for the treatment of high altitude cerebral edema.

Particular embodiments contemplate treating a subject with an injury or disease associated with brain edema in a subject with an inhibitor of SLC26A11 before brain edema develops or becomes detectable to prevent brain edema or to lessen the degree to which brain edema will develop in the subject. In certain embodiments, an inhibitor of SLC26A11 is administered to a subject with an injury or disease associated with brain edema where brain edema has been detected to slow the progression of the brain edema. In some embodiments, and inhibitor of SLC26A11 is administered to a subject with brain edema to reduce the extent of brain edema.

Global brain edema as used herein, refers to brain edema that occurs or effects a majority of the brain. In some embodiments global brain edema is a brain edema that occurs in at least 50%, 55%, 60%, 65%, 70%, 75%, 80%, 85%, 90%, 95%, or 100% (including all integers and ranges in between) of the brain. Focal brain edema, as used herein, refers to edema that occurs in a limited region of the brain or spinal cord. In some embodiments, focal brain edema occurs in cortex, including frontal, parietal, temporal, and occipital cortex, myelencephalon, metencephalon, mesencephalon, diencephalon, thalamus, hypothalamus, medial temporal lobe, hippocampus, amygdala, claustrum, or basal ganglia.

Particular embodiments contemplate that inhibition of SLC26A11 is useful for treatments of diseases associated with elevated or dysregulated chloride ion transport. Further, as SLC26A11 is implicated in the transport of other anions, certain embodiments contemplate that the application of SLC26A11 towards the treatments for diseases associated with disrupted anion transport. Such diseases include, but are not limited to, Bartter's syndrome, alkalosis, Dent's disease, Thomsen disease, Becker disease, diastrophic dysplasia, congenital chloride diarrhea, and cystic fibrosis. In some embodiments, an inhibitor of SLC26A11 is administered to a subject for the treatment of a disease associated with disrupted anion transport. In some embodiments, an inhibitor of SLC26A11 is administered to a subject for the treatment of a disease associated with disrupted $Cl^-$ transport.

Certain embodiments contemplate that inhibition of SLC26A11 is useful for treatment of diseases that involve disrupted neurotransmission. The main inhibitor neurotransmitter receptors of the CNS, GABA, exerts its influence in the CNS in part through the activation of $GABA_A$ receptors. The $GABA_A$ receptor is a ionotropic neurotransmitter receptor, so that when GABA binds to $GABA_A$ receptors, $GABA_A$ receptors convert into an open channel confirmation and permit $Cl^-$ influx into the neuron. The $Cl^-$ influx increases the net negative charge of the neuron and thus reduces the neurons excitability. In certain embodiments, an SLC26A11 inhibitor is administered to a subject for the treatment of a disease that involves disrupted neurotransmission. In some embodiments, the disrupted neurotransmission comprises GABAergic signaling. Diseases associated with disrupted GABAergic signaling include alcoholism, neonatal seizures, epilepsy, including epilepsy resulting from hypoxic-ischemic insult, epilepsy resulting from head trauma, temporal lobe epilepsy, absence epilepsy, epilepsy resulting from K289M mutation in the gamma 2 subunit of $GABA_A$, anxiety disorders, sleep disorders.

In particular embodiments, an inhibitor of SLC26A11 is administered to a subject for the treatment of edema. In some embodiments, the inhibitor is administered orally, nasally, intravenously, intramuscularly, ocularly, transdermally, intracranially, intrathecally, or subcutaneously.

Methods of Screening Inhibitor of SLC26A11

Particular embodiments are directed to a method of screening candidate agents to identify inhibitors of SLC26A11. Certain embodiments employ a strategy whereby a cell stimulated to have increased internal $Cl^-$ concentration, swelling, and/or an increased risk of cell death is contacted with the candidate agent. A measurement of a property of the cell is taken and compared to a first reference standard and a second reference standard. The first reference standard is comprised of a measurement or measurements of the property of a cell that is not stimulated to have increased internal Cl⁻ concentration, swelling, and/or an increased risk of cell death and not is contacted with the candidate agent. The second reference standard is a measurement of the property in a cell that is stimulated to have increased internal Cl⁻ concentration, swelling, and/or an increased risk of cell death and is not contacted with the candidate agent. By comparing measurement of the cell contacted with the candidate agent to the first and the second reference standard, the candidate agent can be assessed to determine if it is an inhibitor of SLC26A11. For example, in some embodiments, a candidate agent is an inhibitor of SLC26A11 if the measurement of a cell contacted with the candidate agent is similar to the first reference standard and different from the second reference standard.

Certain embodiments are directed to screening candidate agents to identify inhibitors of SLC26A11. In certain embodiments, a candidate agent is a natural or chemically modified polypeptide, an antibody, a natural or chemically modified small oligopeptide, a natural, unnatural, or chemically modified amino acid, a polynucleotide, a natural or chemically modified oligonucleotide, RNAi, shRNA, siRNA, a small nucleotide, a natural or chemically modified mononucleotide, a lipopeptide, an antimicrobial, a small molecule, or a pharmaceutical molecule. Some embodiments contemplate that a candidate agent is determined to be an inhibitor of SLC26A11 if reduces Cl⁻ channel activity. In some embodiments, a candidate agent is deemed an inhibitor of SLC26A11 if the candidate agent reduces the probability that the SLC26A11 channel will be in an open confirmation and increases the probability that the channel with be closed conformation, increasing the threshold conditions that result in channel opening, such as the threshold depolarization, reducing the duration of time that SLC26A11 remains in an open state, reducing the Cl⁻ conductance of SLC26A11 when it is in an open, reducing the amount of functional SLC26A11 polypeptide, reducing the amount of SLC26A11 at the plasma membrane, reducing the total levels of SLC26A11, or any combination thereof.

Certain embodiments are directed to screening candidate agents to identify agents that can reduce swelling. In particular embodiments, a candidate agent that inhibits SLC26A11 activity or reduces SLC26A11 expression also reduces cellular swelling. Particular embodiments are directed to screening candidate agents that can ameliorate cell death. In some embodiments, candidate agents that inhibit SLC26A11 activity or reduce SLC26A11 expression ameliorate cell death. Some embodiments are directed to identifying candidate agents that reduce internal Cl- concentration. In particular embodiments, candidate agents that reduce SLC26A11 activity or reduce SLC26A11 expression reduce internal Cl⁻ concentration.

In particular embodiments, a screen for detecting inhibitors of SLC26A11 is performed by contacting a candidate agent to a cell. In some embodiments, the cell is a cultured cell. In some embodiments, the cell is a primary cell in cell culture. In some embodiments, the cell is a primary cultured neuron. In some embodiments the neuron is dissociated from tissue. In some embodiments, the cell expresses an NMDA receptor. In some embodiments, the cell expresses a voltage gated sodium channel. In some embodiments, the cell expresses SLC26A11. In some embodiments, the cell is a primary neuron from a region of a mammalian brain, for example from cortex, hippocampus, striatum, cerebellum, olfactory bulb, amygdala, thalamus, hypothalamus, or spinal cord. In some embodiments, the cell is a cell from a stable neuron-like cell line. Stable neuron-like cell lines include n13, N1E-115, PAJU, PC-12, SH-SY5Y, SHEP, SK-N-SH, SKNMC, SNB 19, T98t, and TR2 cell lines. Cell cultures can be generated or obtained from standard methods known in the art.

In some embodiments, a screen for detecting inhibitors of SLC26A11 is performed by contacting a candidate agent to at least one cell in a portion of mammalian brain. The portion of a mammalian brain can be a portion of mammalian brain in culture (e.g. hippocampal brain slice with or without a septum input, a dissociated hippocampal neuron preparation, a co-culture of septum and hippocampus, a neocortical slice, a thalamocortical slice, a basal ganglia (striatal) slice, and/or a corticostriatal slice). In certain embodiments, the brain tissue sections or tissue slices are brain tissue sections considered suitable by persons of skill in the art for electrophysiological recording, for example to simulate and detect long-term potentiation. Such tissue preparations are standard to those of skill in the art. In some embodiments, brain slices, also referred to herein as brain sections, comprise tissue from region of a mammalian brain, for example from cortex, hippocampus, striatum, cerebellum, olfactory bulb, amygdala, thalamus, hypothalamus, or spinal cord. In some embodiments, the brain tissue section contains hippocampus. In some embodiments, the brain tissue section or slice is from mammalian brain. In some embodiments, the brain tissue section is from rat. In some embodiments the brain tissue section is from mouse. In some embodiments, the mouse is transgenic. In some embodiments, the tissue comprises neurons and astrocytes.

In particular embodiments, screening for an inhibitor of SLC26A11 comprises inducing Cl⁻ intake into the cell. In certain embodiments, the induction of Cl⁻ intake into a cell is achieved by depolarizing the cell. In some embodiments, depolarizing a cell stimulates Na⁺ intake into the cell, which in turn results in Cl⁻ uptake. Techniques and methods to trigger depolarization of a cell, including neurons and neurons in a tissue section, are commonly known in the art. These include, but are not limited to, chemical stimulation and electrical stimulation. In some embodiments, stimulating Na⁺ entry into the cell stimulate a depolarization of the cell, which in turn stimulates Cl⁻ uptake.

In particular embodiments, depolarization of a cell is stimulated by adding a KCl to the cell culture medium. In some embodiments, KCl is added to the medium resulting in a concentration of 40 mM, 45 mM, 50 mM, 55 mM, 60 mM, 65, mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 210 mM, 220 mM, 230 mM, 240 mM, 250 mM, 260 mM, 270 mM, 280 mM, 290 mM, 300 mM, 400 mM, 500 mM, 1 M, (including all integers and ranges in between) to trigger a depolarization of the cell.

In some embodiments, an agent that triggers depolarization is contacted to the cell. Agents that trigger depolarization of a cell include excitatory neurotransmitters and excitatory neurotransmitter agonists. In some embodiments, an excitatory neurotransmitter agonist is an excitatory neurotransmitter, an agent that activates an excitatory neurotransmitter receptor, an agent that increases extracellular levels of excitatory neurotransmitter, for example by stimulating release, inhibiting cellular reuptake, or by inhibiting degradation of the excitatory neurotransmitter. In some embodiments, an agent that triggers depolarization opens channels that are conductive to cations, such as sodium channels, potassium channels, or calcium channels. In some embodiments, an agent that triggers depolarization opens $Na^+$ channels. In certain embodiments, agents that trigger depolarization of a cell include, but are not limited to, excitatory neurotransmitters, excitatory neurotransmitter receptor agonists, excitatory amino acid transporter inhibitors (EAATI), glutamate, dopamine, norepinephrine, epinephrine, acetylcholine, acetylcholinesterase inhibitors, cAMP agonists, sodium channel agonists, and calcium channel agonists. As used herein, an agent "triggers" a depolarization of a cell if contacting the cell with the agent results in the cell's depolarition. As used herein, trigger may be taken to mean to cause, activiate, drive, induce, or stimulate.

In some embodiments, depolarization of a cell is stimulated by providing electrophysiological stimulation. In some embodiments, electrophysiological stimulation is provided by an extracellular electrode. In some embodiments, electrophysiological stimulation is triggered by an intracellular electrode. In some embodiments, the electrophysiological stimulation is provided with the patch clamp technique.

In some embodiments, the cell expresses an optogenetic actuator. In some embodiments, the optogenetic actuator is a channelrhodopsin, halorhodopsin, achaerhodopsin, leptosphaeria rhodopsin, or any other optogenetic actuator known in the art. Channelrhodopsins include variants such as ChR2, ChETA (ChR2 with mutations at position 123), VChR1, C1C2, ChiEF, V1C1, ChR2$^-$2A$^-$ Halo, and ChIoC. Halorhodopsins include variants such as Halo, eNpHR, and eNpHR 3.0. Archaerhodopsins include Arch, eArch 3.0, and ArchT. Leptosphaeria rhodopsins include Mac and eMac. In some embodiments, the cell expresses an optogenetic actuator, and depolarizing the cell is achieved by providing the cell optical stimulation sufficient to activate the optogenetic actuator.

In some embodiments, the induction of $Cl^-$ intake into a cell is achieved by inducing $Na^+$ intake into the cell. Inducing $Na^+$ intake may be achieved by contacting the cell with a sodium channel agonist. In some embodiments, contacting the cell with a sodium channel agonist increases internal $Na^+$ concentration, increases internal $Cl^-$ concentration, induces swelling, and/or causes cell death. Sodium channel agonists include, but are not limited to, alkaloid based toxins, aconitine, batrachotoxin, brevetoxin, ciguatoxin, delphinine, graanotoxin I, and veratridine. In some embodiments, the cell is contacted with veratridine to increase internal $Na^+$ concentration.

In particular embodiments, $Na^+$ intake is achieved by contacting the cell with an ionotropic glutamate receptor agonist. In some embodiments, the ionotropic glutamate receptor is an AMPA receptor agonist. In some embodiments, the ionotropic glutamate receptor is a kainate receptor agonist. In some embodiments, the ionotropic glutamate receptor is an NMDA receptor agonist.

Inducing $Na^+$ intake may be achieved by contacting the cell with an AMPA receptor agonist. When in an open confirmation, an AMPA receptor permits an influx of $Na^+$. In some embodiments, contacting the cell with an AMPA receptor agonist increases internal $Na^+$ concentration, increases internal $Cl^-$ concentration, induces swelling, and/or causes cell death. AMPA receptor agonists include, but are not limited to, Glutamate, AMPA, 5-Fluorowillardiine, Domoic acid, Quisqualic acid, Aniracetam, Cyclothiazide, CX-516, CX-546, CX-614, derivative 11r, CX-691, CX-717, IDRA-21, Org 26576, LY-392,098. LY-404,187, LY-451,395, LY-451,646, LY-503,430, Oxiracetam, PEPA, Piracetam, Pramiracetam, Sunifiram, and Unifiram.

When activated, kainate receptors permit the flow of $Na^+$ into neurons. In some embodiments, contacting the cell with a kainate receptor agonist increases internal $Na^+$ concentration, increases internal $Cl^-$ concentration, induces swelling, and/or causes cell death. Kainate receptor agonists include, but are not limited to, Glutamate, 5-Iodowillardiine, ATPA, Domoic acid, Kainic acid, LY-339,434, or SYM-2081.

In some conditions, binding of glutamate to NMDA receptors is not sufficient to the activate channel activity. At resting membrane potentials, the NMDA receptor channel contains a magnesium or zinc ion that prevents passage of $Na^+$ and $Ca^{2+}$. However, when glutamate binds to the NMDA receptor when the cell is depolarized, the zinc or magnesium ion is removed from the channel and the NMDA receptor becomes conductive to $Na^+$ and $Ca^{2+}$. Some embodiments contemplate that under physiological conditions, AMPA and/or kainate receptor activation of a cell results in, or is accompanied by, NMDA receptor activation in the cell. This is because AMPA receptors, kainate receptors, and NMDA receptors are all activated by extracellular glutamate and these receptors are found in the same cellular regions, e.g. at or near the post synaptic density. Further, AMPA and/or kainate receptor activation can depolarize the cell. Therefore, in some embodiments, NMDA receptor-dependent increases in internal $Na^+$ concentration, internal $Cl^-$ concentration, cellular swelling, and/or cell death are triggered by activation of AMPA and/or kainate receptors.

Inducing $Na^+$ intake may be achieved by contacting the cell with a NMDA receptor agonist. When in an open confirmation, an NMDA receptor permits the flow of $Ca^{2+}$ and $Na^+$. In some embodiments, contacting the cell with a NMDA receptor agonist increases internal $Na^+$ concentration, increases internal $Cl^-$ concentration, induces swelling, and causes cell death. NMDA receptor agonists include, but are not limited to, Aminocyclopropanecarboxylic acid (ACC), D-Cyclosterine, cis-2,3-Piperidinedicarboxylic acid, Aspartic acid, Glutamate, Quinolinate, Homocysteic acid, D-serine, L-serine, D-Alanine, L-Alanine, N-Methyl-D-aspartic acid (NMDA), 3,5-Dibromo-L-phenylalianine, Rapastinel (GLYX-13), NRX-1074. In some embodiments, the cell is contacted with NMDA to increase internal $Na^+$ concentration.

In some embodiments, a cell is contacted with a sodium channel agonist and further contacted with an NMDA receptor antagonist. Conversely, in some embodiments, a cell is contacted with an NMDA receptor agonist and further contacted with a sodium channel antagonist. In certain embodiments, the approach of pairing the inhibitor of an NMDA receptor with a sodium channel agonist or pairing the sodium channel inhibitor with the NMDA receptor agonist is performed to ensure the selectivity of either approach. Sodium channel inhibitors include, but are not limited to, Saxitoxin (STX), Neosaxitoxin (NSTX), Tetrodotoxin (TTX), Benzocaine, Chloroprocaine, Cocaine, Cyclomethycaine, Larocaine, Piperocaine, Propoxycaine, Novocaine, Proparacaine, Amethocaine, Articaine, Bupivacaine, Dibucaine, Etidocaine, Levobupivacaine, Lidocaine/Lignocaine, Mepivacaine, Prilocaine, Ropivacaine, Trimecaine, Atenolol, Esmolol, and Metoprolol, Quinidine, Procainamide, Disopyramide, Mexiletine, Tocainide, Phenytoin, Encainide, Flecainide, Moricizine, and Propafenone. In some embodiments, the sodium channel inhibitor is TTX. NMDA receptor antagonists include, but are not limited to, AP5, Conantokinsm, Dextromethorphan, Dexanabinol, Dizocilpine (MK-801), Ketamine, Memantine, Nitrous oxide, Phencyclidine, Xenon, and Kynurenic acid. In some embodiments, the NMDA receptor antagoinist is AP5.

In some embodiments, cellular Na$^+$ entry is induced under conditions in which other voltage-gated ion channels and ligand-gated transmitter receptors are blocked. In some embodiments, the cell stimulated for Na$^+$ intake is further contacted with at least one calcium channel blocker. Suitable calcium channel blockers include, but are not limited to, Amlodipine (Norvasc), Aranidipine (Sapresta), Azelnidipine (Calblock), Barnidipine (HypoCa), Benidipine (Coniel), j Cilnidipine (Atelec, Cinalong, Siscard), Clevidipine (Cleviprex), Isradipine (DynaCirc, Prescal), Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine, Nisoldipine, Nitrendipine, Pranidipine, Verapamil, Gallopamil, Fendiline, Mebefradil, Bepridil, Flunarizine, Fluspirilene, Gabapentinoids, Gabapentin, Pregabalin, Ziconide, and Cadium ions. In some embodiments, the cell stimulated for Na$^+$ intake is further contacted with cadmium ions (Cd$^{2+}$).

In some embodiments, the cell stimulated for Na$^+$ intake is further contacted with at least one AMPA/kainite receptor antagonist. Suitable AMPA/kainite receptor antagonists include, but are not limited to, CNQX, kynurenic acid, NBQX, PNQX, YM-90K, ZK200775, CP-465,022, Tezampanel, Talampanel, Perampanel, GYKI-52,466, GYKI-53, 655. In some embodiments, the cell stimulated for Na$^+$ intake is further contacted with CNQX.

In some embodiments, the cell stimulated for Na$^+$ intake is further contacted with at least one GABA receptor antagonist. Suitable GABA receptor antagonists include, but are not limited to, Bicuculline, Forsemide, PHP 501 trifluoroacetate, Picrotoxin, Cicutoxin, Cyclothiazide, SCS, SR 95531 hydrobromide, TB 21007, U93631. In some embodiments, the cell stimulated for Na$^+$ intake is further contacted with picrotoxin.

In some embodiments, the cell stimulated for Na$^+$ intake is further contacted with at least one calcium channel antagoinist, at least one AMPA/kainite receptor antagonist, and at least one GABA receptor antagonist. In particular embodiments, the cell stimulated for Na$^+$ intake is further contacted with Cd$^{2+}$, CNQX, and picrotoxin.

In some embodiments, screening for inhibitors of SLC26A11 comprises contacting a candidate agent to the at least one cell. In some embodiments, the cell is induced to have an increased internal concentration of Cr. As discussed above, the cell can be a cell in a cell culture, for example a cell in a primary cell culture or a cell from a stable cell line, as well as in a tissue, such as a brain slice. In some embodiments, the candidate agent contacts the cell by being added to the cell culture or tissue media. In some embodiments, the candidate agent is directly applied to a local region of tissue.

Certain embodiments contemplate a model, based on data presented herein, where prolonged elevation of internal Na$^+$ levels activate a Cl$^-$ influx pathway via SLC26A11 that is ultimately required for neuronal swelling and subsequent cell death. Unlike Na$^+$ whose osmotic influence on the cell can initially be met by a compensating efflux in K$^+$, the anionic intracellular milieu of the cell is largely made up of large impermeable anions. As such, increases in internal Cl$^-$ likely maintain electroneutrality by retaining Na$^+$ and K$^+$ ions intracellularly, thereby increasing intracellular osmolarity and drawing water into the cell. The influx of water increases cellular volume, (i.e. swelling or cellular or cytoxic edema), and later cell death. Based on this model, certain embodiments contemplate that an agent will reduce intracellular Cl$^-$ concentration, reduce cellular swelling, and ameliorate cell death if the agent reduces Cl$^-$ conductance of SLC26A11. These embodiments contemplate that in a controlled system, SLC26A11 inhibitors can be identified among candidate agents by measuring these properties. Thus, particular embodiments are directed to a method for screening candidate agents to identify SLC26A11 inhibitors by contacting a cell having increased Cl$^-$ concentration with a candidate agent and measuring a property of the cell wherein the property is internal Cl$^-$ concentration, cellular swelling, and/or cell death.

Particular embodiments are directed to a method of determining if a candidate agent inhibits SLC26A11 by determining if the agent can reduce swelling in a cell. This method comprises the steps of stimulating intake of Cl$^-$ in a cell, contacting the cell with a candidate agent, measuring the volume of the cell, and comparing the cell volume of the cell to a first reference standard and a second reference standard. The first reference standard comprises at least one measurement of cell volume in a cell that was not stimulated for Cl$^-$ intake, and the second reference standard comprises at least one measurement of cell volume in a cell stimulated for Cl$^-$ intake. Neither the first nor the second references are contacted with the candidate agent. The effects of a candidate agent on cellular swelling can be made by comparing the swelling of the contacted cell to the swelling of the second reference standard. If the cell contacted with the candidate agent has reduced swelling compared to second reference standard, then the candidate agent is deemed to reduce cellular swelling and is a likely inhibitor of SLC26A11.

In some embodiments, cellular swelling is assessed by comparing the cell volume of the cell contacted with the agent to the cell volume in the first reference; that is, the cell volume of the contacted cell is compared to a volume of a cell where Cl$^-$ influx was not stimulated. Swelling can be expressed, for example, as a ratio of the volume of the contacted cell over the volume of the first reference standard. Swelling in the absence of the candidate agent is assessed by taking the volume of the second reference standard over the volume of the first reference standard.

In some embodiments, cellular swelling is measured by taking a measurement cell volume of the cell before Cl$^-$ intake is stimulated in the cell and then taking a second measurement of cell after Cl$^-$ intake has been stimulated in the cell. In some embodiments, cellular swelling is measured in a cell that is in a tissue, such as a brain slice. In some embodiments, the cell is in a brain slice comprising neurons and astrocytes. In some embodiments, astrocytes are visualized with a detectable label. In particular embodiments, astrocytes are visualized with a fluorescent dye. In some embodiments, astrocytes are visualized with sulforhodamine101 (SR101). In some embodiments, neurons are visualized with a detectable label, such as a fluorescent dye. In some embodiments, neurons are visualized with CoroNaGreen. In some embodiments, neurons are visualized sodium-binding benzofuran isophthalate (SBFI). Stimulation with NMDA or veratridine does not induce Cl$^-$ influx or cellular swelling in astrocytes. Thus, in some embodiments, astrocytes can be visualized to serve as constant marker of cell size, or as a reference point for cell size over time. In particular embodiments, cellular swelling in a neuron is measured by taking a measurement of cell volume of the neuron before Cl$^-$ intake is stimulated and normalizing the measurement to a measurement of astrocyte cell volume of an astrocyte in the same brain slice, and then taking a second measurement of neuron volume after Cl$^-$ intake has been stimulated and normalizing it to the astrocyte cell volume.

Certain embodiments contemplate that cellular swelling reduces fluorescence intensity of an intracellular fluorescent dye in a cell. Magnitude and duration of fluorescence signals are, in some instances, distorted during cellular swelling due to dye dilution. Swelling can reduce fluorescence intensity of inert dyes, such as Calcein red-AM, as well as ion-sensitive dyes, such as CoroNaGreen or SBFI. In some embodiments, cellular swelling is measured by detecting a decrease of fluorescence intensity of an intracellular dye in a cell. Particular embodiments contemplate that light transmittance through a cell increases with cellular swelling. In particular embodiments, cellular swelling is measured by detecting an increase in light transmittance of the cell.

As used herein, cell volume can refer to an approximation of cell volume or cell size, and can be made with any standard technique known in the art. Cell volume may be expressed as relative value, i.e. as compared to another cell, or as compared to the same cell at a different time point. Cell volume may also be estimated based on a marker with a known distance, either physical or virtual. Cell volume may be estimated from 2-D images, or may be estimated by analyzing stacked images, such as can be generated with a confocal microscope, to generate 3D models of the cell.

In certain embodiments, a candidate agent is an SLC26A11 inhibitor if it reduces cellular swelling. In certain embodiments, a candidate agent is an inhibitor of SLC26A11 if it reduces swelling by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In some embodiments, a candidate agent is an SLC26A11 inhibitor if it reduces cellular swelling by a statistically significant amount.

Particular embodiments are directed to a method of determining if a candidate agent inhibits SLC26A11 by determining if the agent can reduce internal $Cl^-$ concentration in a cell. Certain embodiments are directed to a method of determining if a candidate agent inhibits SLC26A11 by determining if the agent can reduce the increase of internal $Cl^-$ levels in a cell stimulated to uptake $Cl^-$, for example $Cl^-$ uptake stimulated by increasing the cell's internal $Na^+$ levels. These methods comprise the steps of stimulating intake of $Cl^-$ in a cell; contacting the cell with a candidate agent, measuring the internal $Cl^-$ concentration of the cell, and comparing the internal $Cl^-$ concentration of the cell to a first reference standard and a second reference standard. The first reference standard comprises at least one measurement of internal $Cl^-$ concentration in a cell that was not stimulated for $Cl^-$ intake, and the second reference standard comprises at least one measurement of internal $Cl^-$ concentration in a cell stimulated for $Cl^-$ intake. Neither the first nor the second references are contacted with the candidate agent. The effects of a candidate agent on internal $Cl^-$ concentration can be made by comparing the $Cl^-$ concentration of the contacted cell to the $Cl^-$ concentration of the second reference standard. If the cell contacted with the candidate agent has reduced internal $Cl^-$ concentration compared to second reference standard, then the candidate agent is deemed to reduce chloride intake and is a likely inhibitor of SLC26A11.

In some embodiments, an increase in $Cl^-$ concentration is assessed by comparing the internal $Cl^-$ concentration of the cell contacted with the agent to the internal $Cl^-$ concentration in the first reference; that is, the internal $Cl^-$ concentration of the contacted cell is compared to an internal $Cl^-$ concentration of a cell where $Cl^-$ influx was not stimulated. The increase of internal $Cl^-$ levels can be expressed, for example, as a ratio of the internal $Cl^-$ concentration of the contacted cell over the internal $Cl^-$ concentration of the first reference standard. The increase in $Cl^-$ levels in the absence of the candidate agent is assessed by taking the internal $Cl^-$ concentration of the second reference standard over the internal $Cl^-$ concentration of the first reference standard.

In some embodiments, an increase in $Cl^-$ levels is measured by taking a measurement cell internal $Cl^-$ concentration of the cell before $Cl^-$ intake is stimulated and then taking a second measurement of cell after $Cl^-$ intake has been stimulated. In some embodiments, cellular the increase in $Cl^-$ is measured in a cell that is in a tissue, such as a brain slice. In some embodiments, the cell is in a brain slice comprising neurons and astrocytes. In some embodiments, cells are visualized with a dye that is sensitive to internal $Cl^-$ concentration. In some embodiments, cells are contacted with a dye that is sensitive to internal $Cl^-$ concentrations. Dyes sensitive to internal $Cl^-$ concentrations include SPQ (6- methoxy-N-(3-sulfopropyl)quinolinium), MQAE (N-(ethoxycarbonylmethyl)-6-methoxyquinolinium bromide), lucigenin (bis-N-methylacridinium nitrate), and MEQ (6-methoxy-N-ethylquinolinium chloride). Measuring $Cl^-$ concentrations with $Cl^-$ sensitive dyes are well known in the art, for example as referenced by Verkman et al., Am J Physiol 259, C375 (1990). In particular embodiments, cells are contacted with MQAE, and signal form MQAE is detected to measure internal $Cl^-$ concentration.

In certain embodiments, a candidate agent is an SLC26A11 inhibitor if it reduces internal $Cl^-$ concentration. In particular embodiments, an agent is an SLC26A11 inhibitor if it reduces an increase of internal $Cl^-$ concentration. In certain embodiments, an agent is an inhibitor of SLC26A11 if it reduces internal $Cl^-$ concentration by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In some embodiments, an agent is an inhibitor of SLC26A11 if it reduces internal $Cl^-$ concentration by 1 mM, 2 mM, 3 mM, 4 mM, 5 mM, 6 mM, 7 mM, 8 mM, 9 mM, 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 110 mM, 120 mM, 130 mM, 140 mM, 150 mM, 160 mM, 170 mM, 180 mM, 190 mM, 200 mM, 300 mM, 400 mM, 500 mM, 600 mM, 700 mM, 800 mM, 900 mM, 1 M, 2 M, 3 M, 4 M, 5 M, 6 M, 7 M, 8 M, 9 M, 10 M (including all integers and ranges in between). In some embodiments, a candidate agent is a likely inhibitor of SLC26A11 the candidate agent causes a statistically significant reduction in internal $Cl^-$ concentration.

In some embodiments, cells are visualized with known techniques that are standard in the art. Such techniques include, but are not limited to fluorescence microscopy, confocal microscopy, and two fluorescence-lifetime imaging microscopy (FILM). FLIM is an imaging technique for producing an image based on the differences in the exponential decay rate of the fluorescence from a fluorescent sample. It can be used as an imaging technique in confocal microscopy, two-photon excitation microscopy, and multiphoton tomography. FILM has the advantage of minimizing the effect of photon scattering in thick layers of sample. FLIM imaging is particularly useful in neurons, where light scattering by brain tissue is problematic for ratiometric imaging.

Certain embodiments are directed to a method of determining if a candidate agent inhibits SLC26A11 by determining if the agent can ameliorate death in cells. This method comprises the steps of stimulating intake of Cl⁻ in cells; contacting the cells with a candidate agent, measuring cell death, and comparing the measurement of cell death to a first reference standard and a second reference standard. The first reference standard comprises at least one measurement of cell death in cells that were not stimulated for Cl⁻ intake, and the second reference standard comprises at least one measurement of cell death in cells stimulated for Cl⁻ intake. Neither the first nor the second references are contacted with the candidate agent. The effects of a candidate agent on cell death can be made by comparing the amount of cell death of the contacted cells to the amount of cell death in the second reference standard. If the cells contacted with the candidate agent have a reduced amount of cell death compared to second reference standard, then the candidate agent is deemed to ameliorate cell death and is a likely inhibitor of SLC26A11.

In some embodiments, cell death can be observed in cultured cells in the same culture dish or the same well of a multiple well plate, for example a 6-well plate, a 12-well plate, a 24-well plate, or a 96-well plate. In particular embodiments, cell death can be observed in a tissue, for example a brain slice. In certain embodiments, cell death is measured by standard methods known in the art, for example but not limited to, an LDH assay, TUNEL staining, MTT assay, quantification of ATP consumption, caspase activation assay, nuclear morphology assay, quantification of DNA strand breaks, or quantification of a vital dye.

In certain embodiments, a candidate agent is an SLC26A11 inhibitor if it ameliorates cell death. In certain embodiments, a candidate agent is an inhibitor of SLC26A11 if it reduces cell death by 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In some embodiments, a candidate agent is an SLC26A11 inhibitor if it reduces cell death by a statistically significant amount.

As used herein, a candidate agent is deemed "an inhibitor of SLC26A11" if the agent displays a predicted property of an SLC26A22 inhibitor following any of the methods for identifying inhibitors of SLC26A11 described herein. In some embodiments, this denotes the fact that an agent that displays a predicted property of an SLC26A11 inhibitor, however, in some cases it might possible that a candidate agent that displays predicted properties of an SLC26A11 inhibitor, such as reducing cellular levels of internal Cl⁻, reducing swelling, or ameliorating cell death, may not actually be an SLC26A11 inhibitor. In such cases, the candidate agent may display such a property due to an activity independent of SLC26A11. Therefore, in some embodiments, a candidate agent that displays a predicted property of an SLC26A11 inhibitor in an experiment described herein will be further tested by standard methods known in the art to verify that the candidate agent is an inhibitor of SLC26A11.

Particular embodiments are directed to a method of screening candidate agents to identify inhibitors of SLC26A11 with cells overexpressing SCL26A11. In some embodiments, the cell is a HEK cell. Certain embodiments employ a strategy whereby a cell overexpressing SCL26A11 is stimulated to activate SLC36A11 and is contacted with the candidate agent. A measurement of a property of the cell is taken and compared to a first reference standard and a second reference standard. The first reference standard is comprised of a measurement or measurements of the property of a cell that is not stimulated to have activated SLC36A11 and not is contacted with the candidate agent. The second reference standard is a measurement of the property in a cell that is stimulated to have activated SLC36A11 and is not contacted with the candidate agent. By comparing measurement of the cell contacted with the candidate agent to the first and the second reference standard, the candidate agent can be assessed to determine if it is an inhibitor of SLC26A11. For example, in some embodiments, a candidate agent is an inhibitor of SLC26A11 if the measurement of a cell contacted with the candidate agent is similar to the first reference standard and different from the second reference standard.

In some embodiments the cell that overexpresses SLC26A11 is from a cell line. In some embodiments, suitable cell lines include, but are not limited to, SH-SY5Y, HepG2, HeLa, THP 1, MCF7, SNL 76/7, C3H, C2C12, 3T3 L1, PC-12, Jurkat E6.1, NIH 3T3, U-87 MG, CHO-K1, MDCK, 1321N1, Neuro 2a, SK-N-SK, MDCK, Cos-7, PANC-1, and ND7/23. In some embodiments, the cells are HEK cells (also known as HEK 293 cells or 293 cells). Overexpression of SLC26A11 can be performed by standard techniques known in the art, such as transfection of a nucleotide encoding SLC26A11, for example by electroporation, sonoporation, optical transfection, or chemical based transfection. Chemical based transfection includes transfection by calcium phosphate techniques, dendrimer based techniques, lipofection. Overexpression is also achieved by viral delivery of a nucleotide encoding SLC26A11. As used herein, overexpression refers to inducing expression of a protein in a cell in an amount that is greater than the normal physiological expression of the protein in the cell. Overexpression as used herein also refers to inducing expression of a protein in a cell that does not express the protein under normal physiological conditions.

In some embodiments, the cells are HEK cells that overexpress SLC26A11. In some embodiments, the cells overexpress mammalian SLC26A11. In certain embodiments, the cells overexpress human SLC26A11. In particular embodiments, the cells overexpress rodent SCL26A11. In certain embodiments, the cells overexpress mouse SLC26A11. In certain embodiments, the cells overexpress rat SLC26A11. In particular embodiments, the cells overexpress SLC26A11 polypeptide, or subsequences, fragments, variants (including but not limited to variants resulting from alterative splicing), or derivatives thereof. In some embodiments, the cells are HEK cells that overexpress human SLC26A11.

In particular embodiments, a cell overexpressing SLC26A11 is contacted with a candidate agent. In some embodiments, the cell overexpressing SLC26A11 is contacted with a candidate agent that is a natural or chemically modified polypeptide, an antibody, a natural or chemically modified small oligopeptide, a natural, unnatural, or chemically modified amino acid, a polynucleotide, a natural or chemically modified oligonucleotide, RNAi, shRNA, siRNA, a small nucleotide, a natural or chemically modified mononucleotide, a lipopeptide, an antimicrobial, a small molecule, or a pharmaceutical molecule.

In particular embodiments, screening for an inhibitor of SLC26A11 comprises inducing Cl⁻ intake into a cell overexpressing SLC26A11. In certain embodiments, the induction of Cl⁻ intake into a cell overexpressing SLC26A11 is achieved by depolarizing the cell. In some embodiments, depolarizing a cell stimulates influx of cations into the cell, which in turn results in Cl⁻ uptake. In some embodiments, depolarizing a cell stimulates influx of Na⁺ into the cell, which in turn results in Cl− uptake. In some embodiments, depolarizing a cell stimulates Na+ intake into the cell, which in turn results in Cl− uptake.

In particular embodiments, depolarization of a cell overexpressing SLC26A11 is stimulated by adding a KCl to the cell culture medium. In some embodiments, KCl is added to the medium resulting in a concentration of 40 mM, 45 mM, 50 mM, 55 mM, 60 mM, 65, mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, 150 mM, 155 mM, 160 mM, 165 mM, 170 mM, 175 mM, 180 mM, 185 mM, 190 mM, 195 mM, 200 mM, 210 mM, 220 mM, 230 mM, 240 mM, 250 mM, 260 mM, 270 mM, 280 mM, 290 mM, 300 mM, 400 mM, 500 mM, or 1 M, (including all integers and ranges in between) of KCl to trigger a depolarization of the cell.

In some embodiments, depolarization of a cell overexpressing SLC26A11 is stimulated by providing electrophysiological stimulation. In some embodiments, electrophysiological stimulation is provided by an extracellular electrode. In some embodiments, electrphysiological stimulation is triggered by an intracellular electrion. In some embodiments, the electrophysiological stimulation is provided with the patch clamp technique.

In some embodiments, the cell overexpressing SLC26A11 also expresses an optogenetic actuator. In some embodiments, the optogenetic actuator is a channelrhodopsin, halorhodopsin, achaerhodopsin, *leptosphaeria* rhodopsin, or any other optogenetic actuator known in the art. In some embodiments, the cell expresses an optogenetic actuator, and depolarizing the cell is achieved by providing the cell with optical stimulation sufficient to activate the optogenetic actuator.

Particular embodiments are directed to a method for screening candidate agents to identify SLC26A11 inhibitors by contacting a cell overexpressing SLC26A11 with a candidate agent and measuring a property of the cell wherein the property is Cl− conductance, internal Cl− concentration, cellular swelling, and/or cell death. In some embodiments, the property is Cl− conductance of SLC26A11. In some embodiments, Cl− conductance is measured by detecting the Cl− influx when SLC26A11 is in an open confirmation. In some embodiments, Cl− conductance is measured by detecting Cl− outflow when the SLC26A11 is in an open confirmation. In some embodiments Cl− conductance is detected by Cl− outflow under conditions where the cell is contacted with a medium that has a physiologically low concentration of Cr.

Particular embodiments are directed to a method of screening candidate agents to identify inhibitors of SLC26A11 with cells overexpressing SCL26A11 utilizing patch clamp techniques. Patch clamping is standard technique to measure ion channel function, and allows the study of single or multiple ion channels in cells. Patch clamp recording uses a glass micropipette (patch pipette) as a recording electrode, and another electrode in the bath around the cell as a reference ground electrode. Depending on the experiment, the interior of the pipette can be filled with a solution matching the ionic composition of the bath solution, as in the case of cell-attached recording, or matching the cytoplasm, for whole-cell recording. The researcher can also change the content or concentration of these solutions by adding ions or drugs to study the ion channels under different conditions. The technique provides an ideal signal to noise ratio and also tracts the effects of agents in real time. Tracking the effects of an agent in real time permits complex effects on a channel to be resolved. For example, an agent that elicits a transient potentiation of current followed by a sustained inhibition can be identified. Several variations of patch clamp techniques are well known in the art, and include cell attached patch, whole cell recording, outside cell patch, and perforated patch. Automated systems for patch clamp experiments have been developed and can be applied for screening compounds. In some embodiments, candidate agents are contacted to cells overexpressing SCL26A11 identify inhibitors of SLC26A11 utilizing a patch clamp technique. In some embodiments, the patch clamp technique is automated.

Particular embodiments are directed to a method of screening candidate agents to identify inhibitors of SLC26A11 with cells overexpressing SCL26A11 utilizing patch clamp techniques, whereby the method comprises stimulating channel activity of SLC26A11 by providing applying an applied potential difference; contacting the cell overexpressing with the candidate agent; taking a measurement of SLC26A11 channel conductance; and comparing the measurement to a first reference standard and a second reference standard. The first reference standard is comprised of a measurement or measurements of the property of a cell that is not stimulated with an applied potential difference and not is contacted with the candidate agent. The second reference standard is a measurement from of the property in a cell that is stimulated with an applied potential difference and is not contacted with the candidate agent.

Certain embodiments are directed to a method of screening candidate agents to identify inhibitors of SLC26A11 with cells overexpressing SCL26A11 utilizing colorimetry. Colorimetry as applied to Cl− channel screening is described by Tang and Wildey ((2004) J. Biomol. Screen. 9, 607-613). The method detects transmembrane iodide flux with the Sandell-Kolthoff reaction, whereby the I− converts yellow solution of $Ce^{4+}$ and As to a colorless solution of $Ce^{3+}$ and $As^{4+}$. Cells are placed in an F containing buffer. The channels are activated, allowing I− to flow into the cell down the electrochemical gradient. The rate of accumulation of intracellular I− will depend on the degree to which the Cl− channels are activated. Following the experiment, cells are lysed and the lysate is placed in a detection buffer containing equimolar amounts of Ce4+ and As3+. Since the rate of the above reaction is F dependent, the color of the detection buffer after a given time provides an indication of the transmembrane I− flux rate. This provides a measurement of the Cl− conductance. Since this assay provides a measurement of Cl− conductivity through the detection of a color, it can be utilized for high-throughput screens.

Certain embodiments are directed to a method of screening candidate agents to identify inhibitors of SLC26A11 with cells overexpressing SCL26A11 utilizing colorimetry. In some embodiments, cells overexpressing SLC26A11 are placed in a medium containing F and are contacted with a candidate agent, and SLC26A11 activation is stimulated. SLC26A11 conductance is then measured by removing the cell from the medium, lysing the cell; contacting the cell lysate with a solution containing $Ce^{4+}$ and $As^{3+}$; and detecting the color of the lysate. The color of the lysate indicates internal I− concentration, which is used to measure Cl− conductance of cell.

Certain embodiments are directed to a method of screening candidate agents to identify inhibitors of SLC26A11 with cells overexpressing SCL26A11 utilizing a pH detection assay. Most Cl− channels are permeable $HCO_3^-$ ions. Since $HCO_3^-$ exists at a high concentration inside cells, it diffuses out of cells when Cl− channels are opened, leading to a detectable decrease in extracellular pH. in a cell culture medium acidified to a pH of 6.9 (Simpson et al. J. Neurosci Methods, 99, 91-100). This pH change can be measured with a pH sensitive dye, such as by detecting fluorescence changes of the pH sensitive dye 2',7'bis⁻ (2-carboxyethyl)-5-(and 6)-carboxyfluorescein (BCECF).

Particular embodiments are directed to a method of screening candidate agents to identify inhibitors of SLC26A11 with cells overexpressing SCL26A11 utilizing a pH detection assay. In some embodiments, cells overexpressing SLC26A11 are placed in a medium with a pH of about 6.9 and are contacted with a candidate agent, and SLC26A11 activation is stimulated. SLC26A11 conductance is then measured by detecting changes in the extracellular pH, wherein a decrease in extracellular pH indicates Cl⁻ channel conductance of SLC26A11. In some embodiments, changes in the extracellular pH are detected with a pH sensitive dye. In some embodiments, the pH sensitive dye is BCECF.

Some embodiments are directed to a method of screening candidate agents to identify inhibitors of SLC26A11 with cells overexpressing SLC26A11 utilizing voltage sensitive dyes. A range of voltage sensitive dyes are commercially available, which provide different characteristics. The FLIPR fluorescent membrane potential dye marketed by Molecular Devices is a commonly used dye for high throughput screening of Cl⁻ channel inhibitors. It can be used for screening cation-selective channels and used with HEK293 cells stably expressing glycine receptors. In some instances, an assay is set up so that Cl⁻ channel activation induces a depolarization and a consequent increase in fluorescence.

Certain embodiments are directed to a method of screening candidate agents to identify inhibitors of SLC26A11 with cells overexpressing SLC26A11 by contacting the cell with a voltage sensitive dye. In particular embodiments, measuring Cl⁻ conductance of SLC26A11 is performed by detecting a change in membrane potential following SLC26A11 activation. In some embodiments, a change in membrane potential is performed by measuring the fluorescence signal of the voltage sensitive dye, thereby measuring the conductance of the channel. In some embodiments, the voltage sensitive dye is FLIPR fluorescent membrane potential dye.

Particular embodiments are directed to a method of screening candidate agents to identify inhibitors of SLC26A11 with cells overexpressing SCL26A11 utilizing fluorescence resonance energy transfer (FRET). This technique involves the non-radiative transfer of energy from a donor fluorophore to an acceptor fluorophore when the donor emission spectra and acceptor absorption spectra overlap and they are in close proximity, about 20 about 100 angstrom. When the donor is stimulated at its absorption wavelength, FRET causes the acceptor fluorescence to increase and donor fluorescence to decrease. It has been shown that the donor, CC2-DMPE, and the acceptor, DiBac2, produce a robust FRET at negative membrane potentials when both are localized to the external membrane surface. Upon depolarization, DiBac2 crosses the membrane, thereby increasing its distance from CC2-CPMPE and decreasing FRET efficiency.

Certain embodiments are directed to a method of screening candidate agents to identify inhibitors of SLC26A11 with cells overexpressing SLC26A11 by contacting the cell with a FRET acceptor and a FRET donor. In particular embodiments, screening a candidate agent with cells overexpressing SLC26A11 is performed whereby a candidate agent is contacted to a cell overexpressing SLC26A11; SLC26A11 is stimulated; and FRET signal is measured to determine if there is a change in membrane potential, thereby measuring Cl⁻ conductance. In certain embodiments, the cell overexpressing SLC26A11 is contacted with the FRET donor CC2-DMPE, and the FRET acceptor DiBac2. In some embodiments, determining if a candidate agent is an inhibitor of SLC26A11 is performed by contacting the cell overexpressing SLC26A11 with the FRET donor CC2-DMPE and the FRET acceptor DiBac2; activating SLC26AA in the cell overexpressing SLC26A11; contacting the cell overexpressing SLC26A11 with a candidate agent; and measuring the FRET signal in the cell, where change in the FRET signal indicates a change in Cl⁻ conductance of SLC26A11.

Some embodiments are directed to a method of screening candidate agents to identify inhibitors of SLC26A11 with cells overexpressing SLC26A11 utilizing YFP. YFP, an engineered variant of green fluorescent protein, is quenched by small anions and is thus suited to reporting anionic influx into cells. Two mutations in YFP have been identified, I152L and V163S, each of which greatly enhance YFP anion sensitivity. The I152L mutation confers a particularly high sensitivity to Iquench (Ki ~3 mM). YFP has been applied to monitor GlyR and GABAAR activities (Kruger et al. (2005) Neurosci. Lett., 380, 340-345).

Particular embodiments are directed to a method of screening candidate agents to identify inhibitors of SLC26A11 with cells overexpressing SLC26A11 and also expresseing YFP. In certain embodiments, the YFP has an I152L mutation. In some embodiments, the YFP has a V163S mutation.

In particular embodiments, screening candidate agents to identify SLC26A11 inhibitors is performed with the steps of contacting a candidate agent to a cell overexpressing SLC26A11 and expressing YFP; stimulating SLC26A11; and measuring YFP signal, thereby measuring Cl⁻ conductance. In certain embodiments, a decrease in YFP fluorescence signal indicates an increase of internal Cl⁻ levels.

Below are examples of specific embodiments for carrying out the present invention. The examples are offered for illustrative purposes only and are not intended to limit the scope of the present invention in any way. Efforts have been made to ensure accuracy with respect to numbers used (e.g. amounts, temperatures, etc.) but some experimental error and deviation should be allowed for.

EXAMPLES

Example 1

Experimental Procedures

Imaging: Live cell imaging (brain slice) was performed with a two-photon laser-scanning microscope (Zeiss LSM510-Axioskop-2; Zeiss, Oberkochen, Germany) with a 40X-W/1.0 numerical aperture objective lens directly coupled to a Chameleon ultra2 laser (Coherent, Santa Clara, Calif.). CoroNa, SR101 and DiI were excited at 770 nm, and MQAE was excited at 760 nm. The fluorescence from each fluorophore was split using a dichroic mirror at 560 nm, and the signals were each detected with a dedicated photo multiplier tube after passing through an appropriate emission filter (DiI, SR101: 605 nm, 55 nm band pass; CoroNa, MQAE: 525 nm, 50 nm band pass). Transmitted light was simultaneously collected using understage infrared differential interference contrast optics and an additional photo multiplier tube. FLIM methodology is described in detail in the extended experimental procedures.

Data Collection, Analysis and Statistics: Translational movement was removed using Image J software. Fluorescence signals were defined as delta F/F (dF/F)=[((F1−B1)−(F0−B0))/(F0−B0)], where F1 and F0 are fluorescence at a given time and the control period mean, respectively. B1 and B0 are the corresponding background fluorescence signals. Swelling of individual neurons in cortical slices was analyzed as (%) increase in cross sectional area relative to a mean baseline period. The cross sectional area of the neuron was calculated using the fluorescence boundary of the neuron soma stained with CoroNa. To estimate the tissue volume from the 2 dimensional images of hippocampal slices a line was drawn to measure the diameter and the volume was estimated based on the equation for volume of sphere: $(4/3)\pi r2$.

Experimental values are the mean±SEM; baseline equals 100%; n is the number of experiments conducted (Imaging data from ≥3 individual cells from each experiment were averaged for each n value so that equal weight was given to each experiment and not affected by the number of cells imaged per experiment). Statistical tests were either a two-tailed Student's t test or an ANOVA with a Neumann-Keuls post-hoc test for comparison between multiple groups. $P<0.05$ was accepted as statistically significant (*$P<0.05$, $1^3<0.01$, *$1^3<0.001$)

Slice Preparation: Sprague Dawley rats were anesthetized with halothane and decapitated according to protocols approved by the University of British Columbia Committee on Animal Care. Brains were rapidly extracted and placed into ice-cold slicing solution containing (in mM): NMDG, 120; KCl, 2.5; NaHCO3, 25; CaCl2, 1; MgCl2, 7; NaH2PO4, 1.25; glucose, 20; Na-pyruvate, 2.4; and Na-ascorbate, 1.3; saturated with 95% O2/5% CO2. Coronal hemisections or transverse hippocampal slices, 400 μm thick, were sliced using a vibrating tissue slicer (VT1200, Leica, Nussloch, Germany). Slices were incubated at 32° C. in artificial CSF containing (in mmol/l): NaCl, 126; KCl, 2.5; NaHCO3, 26; CaCl2, 2.0; MgCl2, 1.5; NaH2PO4, 1.25; and glucose, 10; saturated with 95% O2/5% CO2 for 30 minutes. For experiments, slices were at 22-24° C. and perfused at ~2 ml/minute, with the exception of a subset of specified imaging experiments done at 37° C. as measured in the bath and the LDH release experiments (28° C.). Postnatal day (p) 14-22 old rats were used for all experiments except for siRNA transfected rats which were injected at p21-23 and experiments conducted at p26-29.

Dye Loading Protocols: Slices were incubated in ACSF plus SR101 (1 μM) at room temperature for 30 minutes. For CoroNa and Calcein Red-AM loading, slices were preincubated in 3 mL aCSF and 8 μL Cremophor EL solution (0.5% in DMSO) at 32° C. for 5 min. AM dye (50 μg) mixed with 8 μL DMSO and 2 μL pluronic F-127 solution (10% in DMSO) was then added, and slices were allowed to incubate for an additional 45 min. For MQAE loading, slices were bulk loaded with the dye MQAE (6 mM) for 15 minutes at 34° C.

Pharmacology: Drugs were purchased from the following suppliers; Veratridine, d-APV, TTX, CNQX (abcam); DIDS, picrotoxin, niflumic acid, carbenoxelone, acetazolamide, bumetanide (sigma); NPPB (tocris); GlyH-101 (EMD Millipore). Targets are as follows (Extended Data Table 1); NPPB (200 μM), volume regulated anion channel (VRAC, VSOR) (Inoue et al., 2005; Inoue and Okada, 2007); niflumic acid (NFA) (200 μM), $Ca^{2+}$ activated $Cl^-$ conductance (CaCC, TMEM16B) (Huang et al., 2012; White and Aylwin, 1990); $Gd^{3+}$ (100 μM), Maxi-anion channel (Fields and Ni, 2010; Sabirov et al., 2001; Sabirov and Okada, 2009); pannexins/connexins (Bruzzone et al., 2005; Thompson et al., 2008); Zinc (300 μM), CLC-2 (Staley et al., 1996); carbenoxelone (CBX) (100 μM), pannexins/connexins (Bruzzone et al., 2005; Thompson et al., 2008); bumetanide (100 μM), cation chloride cotransporters (NKCC1 and KCC2) (Glykys et al., 2014; Payne et al., 2003); DIDS (250 μM), SLC4 and SLC26 family members (Grichtchenko et al., 2001; Parker et al., 2008; Romero et al., 2013; Svichar et al., 2009; Vincourt et al., 2003; Xu et al., 2011). Veratridine and NMDA application; a glass micropipette (tip diameter ~2 μm) was positioned 10 μm above the slice and 25 μm lateral to the center of the imaging frame. The pipette was filled with the perfusion solution plus either veratridine or NMDA. A monometer was used to standardize the rate of drug application.

Fluorescence Lifetime Imaging (FLIM): Fluorescence lifetime images were acquired using a Becker & Hickl SPC-150 module. Photon emission was detected using a high speed hybrid detector, HPM-100-40 (Hamamatsu). Images were acquired 128 by 128 pixels in fast xy raster scanning mode. Photons were collected over 20 seconds before calculating and extracting lifetimes at each pixel using SPCImage software (Becker & Hickl). Instrument response function (IRF) was calculated using a 10 nm gold nanoparticle suspension (Sigma-Aldrich) to generate a second-harmonic signal. The IRF had a full width at half the maximum amplitude of 121 ps. The lifetimes presented in the figures were the average of all lifetimes within the cytoplasm of the soma. The mean lifetime from all cells in a given experiment were combined and represented as an n=1. MQAE: The $Cl^-$ dependence of MQAE lifetime is described by the Stern-Volmer relation ($\tau 0/\tau = 1 + Ksv [Cl^-]i$), where $\tau 0$ is the fluorescence lifetime in 0 mM $Cl^-$, and Ksv (the Stern-Volmer constant) is a measure of the Cl2 sensitivity of MQAE. Ksv varies greatly between studies due to differences in cell types, preparation and calibration methods (Doyon et al., 2011; Hille et al., 2009; Kaneko et al., 2001; Kaneko et al., 2004), making it difficult to accurately estimate absolute $[Cl^-]i$ in situ. CoroNa: A biexponential decay was used to fit CoroNa lifetimes due to poor fit with a single exponential decay, suggesting fluorescence from multiple components. For calibration, neurons were continually voltage-clamped at −70 mV and dialyzed for >10 min before image acquisition. The intracellular solution contained (in mM) potassium gluconate, 108; KCl, 8; sodium gluconate, 8; MgCl2, 2; HEPES, 10; potassium EGTA, 1; potassium, ATP, 4; and sodium GTP, 0.3; pH 7.2 with KOH. Sodium concentration was altered by replacement of potassium gluconate with sodium gluconate. A linear fit of τfast vs $[Na^+]$ was used to then estimate experimental values of $[Na^+]i$.

Cell Selection for Neuronal Swelling Assay: In order to minimize variability multiple cells (≥3 cells) were chosen for analysis during each experiment and averaged to make 1 n value (1 experiment=1 n value). Cells for analysis were chosen based on the following criteria before the start of the experiment; 1) identified by DIC optics to have a smooth round and shinny membrane as is done when selecting healthy neurons for patch clamping, 2) possessed somas that were spatially separated from neighboring neurons to allow for analysis using the fluorescent boundary of the cell 3) 45-65 μm deep, 4) slices were used within 3.5 hours of slicing, 5) as a positive control, cells were only analyzed if they showed a peak Na+ signal of >25%. Finally to minimize any variability from the preparation, treatments and controls were interleaved.

LDH Assay: LDH assay kits (Biomedical Research Service Center, State University of New York at Buffalo) were used to investigate cell death using rat hippocampal slices. Hippocampal brain slices were prepared as described in brain slice preparation section above. Hippocampal slices were pretreated at 28° C. for 30 min. with a cocktail of ligand gated and voltage gated ion channel inhibitors (100 µM picrotoxin, 20 µM CNQX, 1 µM TTX) when 100 µM NMDA was applied or (100 µM picrotoxin, 20 µM CNQX, 30 µM Cadmium, 100 µM d-APV) when 50 µM veratridine was applied. NMDA experiments were done in 0 mM $Ca^{2+}$, 2 mM EGTA. NMDA or Veratridine was applied to slices for 15 min in a 6 well plate aerated with 95% O2/5% CO2 on an insert for organotypic culture (Millipore) for better aeration. Subsequently slices were transferred to incubation chamber and further incubated for 90 min. Supernatants were collected at 90 min and then slices were lysed using lysis buffer. The LDH level in the supernatant represents the cell death, whereas the LDH level in lysed cells represents the viable cells. In brief, supernatants and cell lysates were centrifuged for 3 min at maximal speed (16,000 g) at 4° C. Samples were added into a 96-well plate with LDH assay solution and incubated for 30 min at 37° C. Acetic acid (3%) was added to stop the reaction. LDH reduces tetrazolium salt INT to formazan, which is water-soluble and exhibits an absorption maximum at 492 nm. Absorbance was measured at 492 nm using a microplate reader. Cell death is presented as the percentage of LDH released (LDH in supernatant/cell lysate LDH)*100.

Western Blots: At 5 days post injection with LNP-siRNAs (Slc26a11 and luciferase) into the cortex, rat cortical brain slices were prepared as previously described (Rungta et al., 2013). Tissues were obtained from brain slices (400 µm thickness) within 1 mm from the site of injection. The injection site was not included in the sample preparation. Subsequently tissues were homogenized using lysis buffer containing (in mM): Tris pH 7.0, 100; EGTA, 2; EDTA, 5; NaF, 30; sodium pyrophosphate, 20; 0.5% NP40 with phosphatase and protease inhibitor cocktail (Roche, Basel, Switzerland). The homogenates were centrifuged at 13,000 g (20 min at 4° C.) and the supernatants were collected for the Western blotting. Equal amounts of protein samples were diluted with 2× Laemmli sample buffer and agitated on a shaker overnight at room temperature. Following sodium dodecyl sulfate/polyacrylamide gel electrophoresis (SDS/PAGE), proteins were transferred to polyvinylidene fluoride (PVDF) membranes using a semi-dry transfer system (Bio-rad). The membranes were blocked in 2% non fat milk for 1 h at room temperature, rinsed with Tris-buffered saline with 0.1% Tween 20 (TBST), and incubated with rabbit anti-slc26a11 polyclonal antibody raised against SLC26A11 specific sequence, CQQEPGTQPYSIRED (Genscript, 1:2000) or goat anti-actin polyclonal antibody (Santa Cruz, 1:500) overnight at 4° C. Following 5 washes with TBST, the membranes were incubated with the anti-rabbit (1:20000) or anti-goat secondary antibody (1:5000) conjugated to horseradish peroxidase (HRP) for 50 min at room temperature. The membranes were then washed 5 times with TBST, and bands were visualized using enhanced chemiluminescence (EMD Millipore Immobilon). Image) (NIH) was used to analyze slc26a11 band intensity relative to actin.

Electrophysiology: Whole-cell recordings were performed in the presence of antagonists of GABAA (10 µM picrotoxin), AMPA/kainite (10 µM 6-cyano-7-nitoquinoxaline-2,3-dione—CNQX), and NMDA (2R-amino-5-phosphonovaleric acid—APV) receptors. 60 µM cadmium, 50 µM nickel and 100 µM 4AP (4-aminopyridine) were used to block voltage-gated calcium channels and A-type potassium channels. Whole-cell voltage-clamp recordings from cortical neurons were carried out at room temperature while the recording chamber was perfused with ACSF at 1-1.5 ml min-1. Recordings were made using a MultiClamp 700B amplifier controlled by Clampex 10.2 via a Digidata 1440A data acquisition system with 3-5MΩ glass electrodes. The pipette solution containing (in mM): 108 CsCl, 8 TEA-Cl, 8 NaGluc, 1 CsEGTA, 4 K-ATP, 0.3 Na-GTP, 10 Hepes, 2MgCl2 (pH 7.2 with CsOH, 286 mosmol 1-1). Normal ACSF contained (in mM): 126 NaCl, 26 NaHCO3, 10 glucose, 2 MgCl2, 1.25 NaH2PO4, 2.5 KCl, 2.0 CaCl2 (pH 7.25, 310 mosmol 1-1). NaCl was replaced with 126 mM Na-isethionate in the low-chloride ACSF. Recordings where the series resistance varied more than 10% were rejected. Data were analyzed with Clampfit 10.0.

Intracranial Injections: All experimental protocols were approved by the Committee on Animal Care, University of British Columbia and conducted in compliance with guidelines provided by the Canadian Council of Animal Care. Sprague-Dawley rats (P22-P26) were anesthetized with isofluorane before and throughout the surgery. A small hole (diameter ~1 mm) was drilled in the skull to allow access to the brain (−2.0 mm anterior/posterior (AP) and ±3.0 mm medial/lateral (ML) from bregma and 0.8 mm dorsal/ventral (DV)). A glass micropipette (tip diameter ~40 µm) was connected to a Hamilton syringe and LNP-siRNAs in sterile PBS were injected using an infusion pump (Harvard Apparatus, Holliston, Mass.) at a rate=~50 nl/minute. The total volume injected was 500 nl of LNP-siRNA (5 mg siRNA/ml in sterile PBS).

Lipid Nanoparticle (LNP) Encapsulation of siRNA:

The ionizable cationic lipid 3-(dimethylamino)propyl (12Z,15Z)-3-[(9Z,12Z)-octadeca-9,12-dien-1-yl]henicosa-12,15-dienoate (DMAP-BLP) and PEG lipid PEG-DMG were provided by Alnylam Pharmaceuticals and have been previously described (Rungta et al., 2013). 1,2-distearoyl-sn-glycero-3-phosphocholine (DSPC) and cholesterol were obtained from Avanti (Alabaster, Ala.) and Sigma-Aldrich Co. (St. Louis, Mo.) respectively. The lipophilic carbocyanine dye to monitor LNP-siRNA uptake, 1,1'-dioctadecyl-3,3,3%3' tetramethylindocarbocyanine perchlorate (DiIC18), was purchased from Invitrogen (Carlsbad, Calif.). The lipid composition of all lipid nanoparticles containing siRNA (LNP-siRNA) was DMAP BLP/DSPC/cholesterol/PEG-DMG/DiIC18 (50/10/37.5/1.5/1; mol %) LNP-siRNA were prepared employing a microfluidic mixing apparatus as previously described (Rungta et al., 2013). Physical parameters characterizing the LNP siRNA systems and the siRNA: lipid ratio are listed in Extended Data Table 2. PDI, polydispersity index.

Quantitative PCR (qPCR): Total RNA was Purified using Life Technologies MagMax-96 Microarray Total RNA Isolation Kit (AM1839), and cDNA created using the Applied Biosystems High Capacity cDNA Reverse Transcription Kit (4368814). Gene specific qPCR reactions were set up using the KAPA Probe Fast Universal qPCR Kit (KK4702) using TaqMan™ probes from Life Technologies and Integrated DNA Technologies (IDT). Specific TaqMan™ probes used in this study:—rSLC4A1 (Rn00561909_m1), rSLC4A2 (Rn00566910_m1), rSLC4A3 (Rn00436642_m1), rSLC4A4 (Rn00584747_m1), rSLC4A5 (Rn01420902_m1), rSLC4A7 (Rn00589539_m1), rSLC4A8 (Rn01532883_m1), rSLC4A9

(Rn00596175_m1), rSLC4A10 (Rn00710136_m1), rSLC4A11 (Rn01515154_m1), rACTB (4352340E), rGAPD (4352338E) from Life Technologies, and rSLC26A1 (Rn.PT.53a.10186844), SLC26A2 (Rn.PT.53a.38316256), rSLC26A3 (Rn.PT.53a.13331783), rSLC26A4 (Rn.PT.53a.37046344), rSLC26A5 (Rn.PT.53a.14115266), rSLC26A6 (Rn.PT.53a.12307129gs), rSLC26A7 (Rn.PT.53a.10816391), rSLC26A9 (Rn.PT.53a.6784539), rSLC26A10 (Rn.PT.53a.5866317), rSLC26A11-1 (Rn.PT.53a.36735939), rSLC26A11-2 (Rn.PT.53a.13211186), rGAPDH (Rn.PT.56a.35727291) all from IDT. Quantitative PCR reactions were performed on a Life Technologies 7500 Real-Time PCR system or Bio-Rad CFX Real-Time Systems, using cycling conditions of 95° C. for 3 minutes then 95° C. for 15 seconds followed by 60° C. for 45 seconds for 40 cycles. The rGAPDH or rACTB probes were used for normalization of controls in relative quantification of other gene expression measurements.

Gene Knock-Down Dicer-substrate RNAs (DsiRNAs): Chemically synthesized siRNA 27mer duplexes were obtained from IDT and screened for knockdown potency by qPCR in culture using plasmid expression knockdown of the cloned rSLC targets expressed in HEK293 cells and of cultured rat cortical neurons. The most potent duplexes were then re-synthesised with 2'-O-methyl (m) patterning for in vivo stabilization, packaged into LNPs and re-tested for potency of gene expression knockdown in cultured rat cortical neurons by qPCR.

```
rSLC4A3
(Sense-rGrGrArUrUrArCrUrCrUrArUrCrArCrArGrAr

CrArCrCrUAC [SEQ ID NO: 7], Antisense-rGrUr

ArGrUrGrUrCrUmGrUmGrArUrArGrArGrUmArAmUr

CmCmAmC [SEQ ID NO: 8])

rSLC4A8
(Sense-rArCrArGrCrGrGrUrCrUrUrArArArGrUrUr

UrArUrCrCrCAA [SEQ ID NO: 9], Antisense-rUr

UrGrGrArUrArArAmCrUmUrUrArArGrArCrCmGrCm

UrGmUmCmA [SEQ ID NO: 10])

rSLC4A10
(Sense-rUrGrCrUrUrArUrArArArGrCrUrArArArG rArCrCrGrCrAAT [SEQ ID NO: 11], AntisenserArUrUrGrCrGrGrUrCrUmUrUmArGrCrUrUrUrArUmA rAmGrCmAmAmC [SEQ ID NO: 12])

rSLC26A11-1
(Sense-rGrCrArUrGrUrCrArGrCrArArUrArUrArGr

ArCrUrArCrACC [SEQ ID NO: 13], AntisenserGrGrUrGrUrArGrUrCrUmArUmArUrUrGrCrUrGrAmC rAmUrGmCmGmU [SEQ ID NO: 14])

rSLC26A11-2
(Sense-mGmGrAmGrAmUrCrCrArArUmArCmGrGmCrA mUrCrCrUrGrGmCA [SEQ ID NO: 15], AntisenserUrGmCrCrArGrGrAmUrGmCrCmGrUrArUrUrGrGrArU rCmUrCmCmCmA [SEQ ID NO: 16])
```

Example 2

Increased Intracellular Sodium Triggers Neuronal Swelling

Figure 1A:
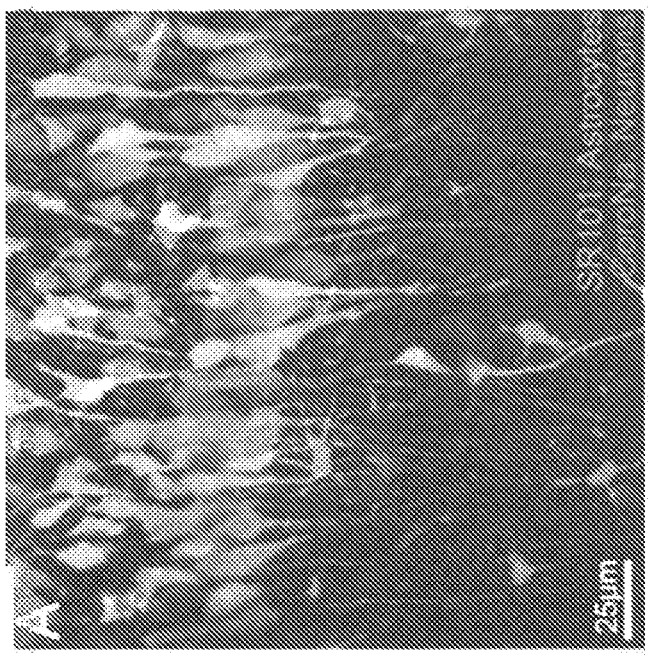
Figures 3A, 3B:
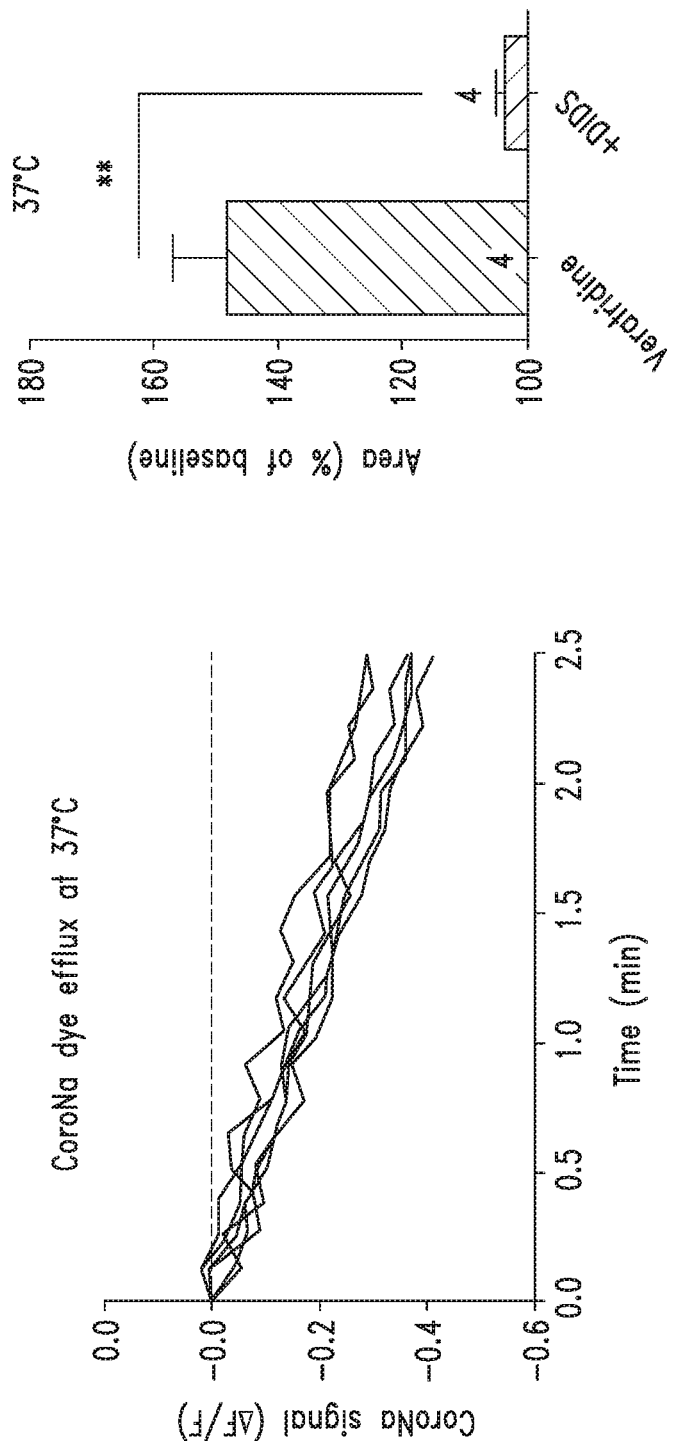
FIG. 3 shows validation that DIDS sensitive neuronal swelling occurs at physiological temperature. (A) The rapid decrease in the baseline fluorescence indicated that CoroNa-AM was rapidly pumped out of neurons at 37° C. making it unfeasible to measure intracellular $[Na^+]$ changes over even short periods of time during the swelling experiments at higher temperatures. (B-C) Increasing neuronal $[Na^+]i$ at 37° C. resulted in robust swelling similar in magnitude to the swelling observed at 23-24° C. Scale bar, 15 µm.
Figure 3C:
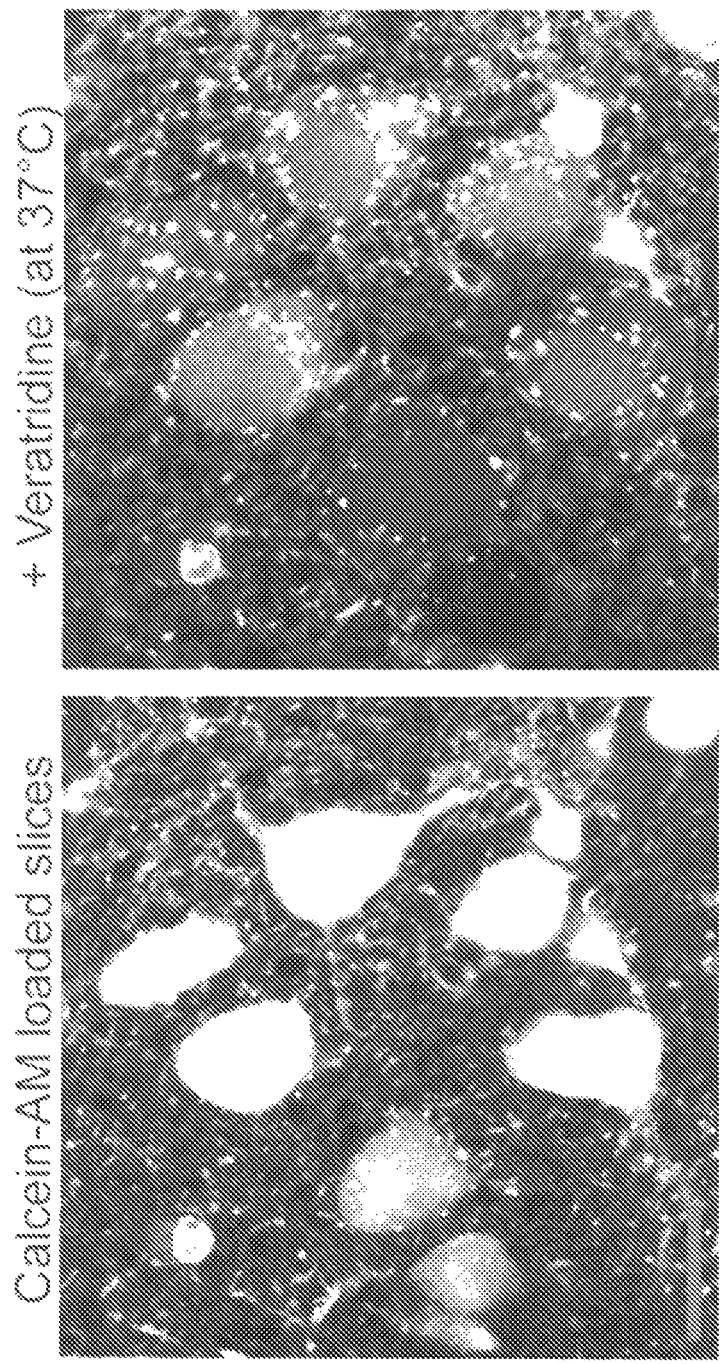

Two parallel and independent approaches were taken to increase [Na$^+$]i by either applying veratridine, which removes inactivation of voltage-gated sodium channels (VGSCs) (Strichartz et al., 1987) prolonging Na$^+$ entry or by applying NMDA to activate NMDA receptors (NMDARs), in order to determine if increasing [Na$^+$]i is capable of triggering a cascade leading to an increase in cell volume and whether this cascade leads to cell death. NMDA activates a non-selective cation conductance leading to entry of Na$^+$ and also Ca$^{2+}$. Neuronal Na$^+$ entry was induced under conditions in which other voltage-gated ion channels and ligand-gated transmitter receptors were blocked by a combination of Cd$^{2+}$ (30 μM), CNQX (20 μM) and picrotoxin (100 μM). Either veratridine or NMDA was rapidly applied by pressure ejection from a pipette positioned directly above the region of the brain slice that was imaged. To ensure the selectivity of either approach veratridine was applied with d-APV (100 μM) to block NMDARs and NMDA was applied with TTX (1 μM) to block VGSCs. Changes in [Na$^+$]i were monitored using the fluorescent Na$^+$ indicator CoroNa-Green (Meier et al., 2006) which preferentially stains hippocampal and cortical neurons in brain slices (FIG. 1A). Calibrated values for each [Na$^-$] were obtained from n≥3 voltage clamped neurons. Astrocytes, which did not show any obvious volume changes under these experimental manipulations, were visualized using Sulforhodamine 101 (SR101) (Nimmerjahn et al., 2004) to provide landmarks to track during swelling of the tissue (FIGS. 1 A and 1B). The activation of either VGSCs by veratridine or NMDARs by NMDA consistently led to a significant increase in [Na$^+$]i followed, after a delay of seconds, by an increase in neuronal cell volume (FIGS. 1B-1D, 1J, 1K, FIGS. 2A, 2B). Control confirms Na$^+$ signal and swelling caused by veratridine and NMDA was via VGSCs and NMDARs respectively, as they were blocked by antagonists, TTX (1 μM) and d-APV (100 μM). All experiments were done in the presence of 30 mM Cd$^{2+}$, 20 μM CNQX, 100 μM picrotoxin. Additionally, neurons were pretreated with 100 μM d-APV (NMDAR antagonist) for veratridine experiments and 1 μM TTX (VGSC antagonist) for MDA experiments to confirm pathways were independent. Control values in (J) and (K) are also re-plotted in FIG. 6 and FIG. 7. Error bars and shaded region above and below the mean represent SEM. The impact of Ca$^{2+}$ versus Na$^+$ entry through NMDARs on swelling was compared by repeating experiments in Ca$^{2+}$ or Na$^+$ free extracellular solutions. The increase in cell volume from NMDAR activation was still observed in extracellular Ca$^{2+}$ free solution (cross sectional area increased to 161.60±10.55% of baseline). However, in the presence of low concentration of extracellular Na$^+$ ([Na$^+$]ext) and normal Ca$^{2+}$, swelling was completely absent and NMDAR activation actually resulted in a decrease in neuronal volume (FIG. 1.1, FIGS. 2C and 2D). Control experiments showed that neuronal [Na$^+$]i increases and swelling induced by veratridine were blocked by the VGSC antagonist, TTX (FIGS. 1.1 and 1K; p<0.001, two-tailed Student's t test) and those induced by NMDA were blocked by the NMDAR antagonist, d-APV (FIGS. 1J and 1K; p<0.001, analysis of variance (ANOVA)). The experimental assay was performed at room temperature to facilitate the imaging of AM indicator dyes which are more rapidly extruded from neurons at 37° C. (Beierlein et al., 2004) (FIG. 3). Swelling was monitored with the dye, Calcein green-AM, and was quantified 2.5 minutes after a 5 minute application of veratridine. However, as the function of many transporters and metabolic proteins that govern ion transport are temperature-dependent, we confirmed that increases in [Na$^+$]i equally cause swelling of neurons at 37° C. (FIG. 3).

Figures 1G, 1H:
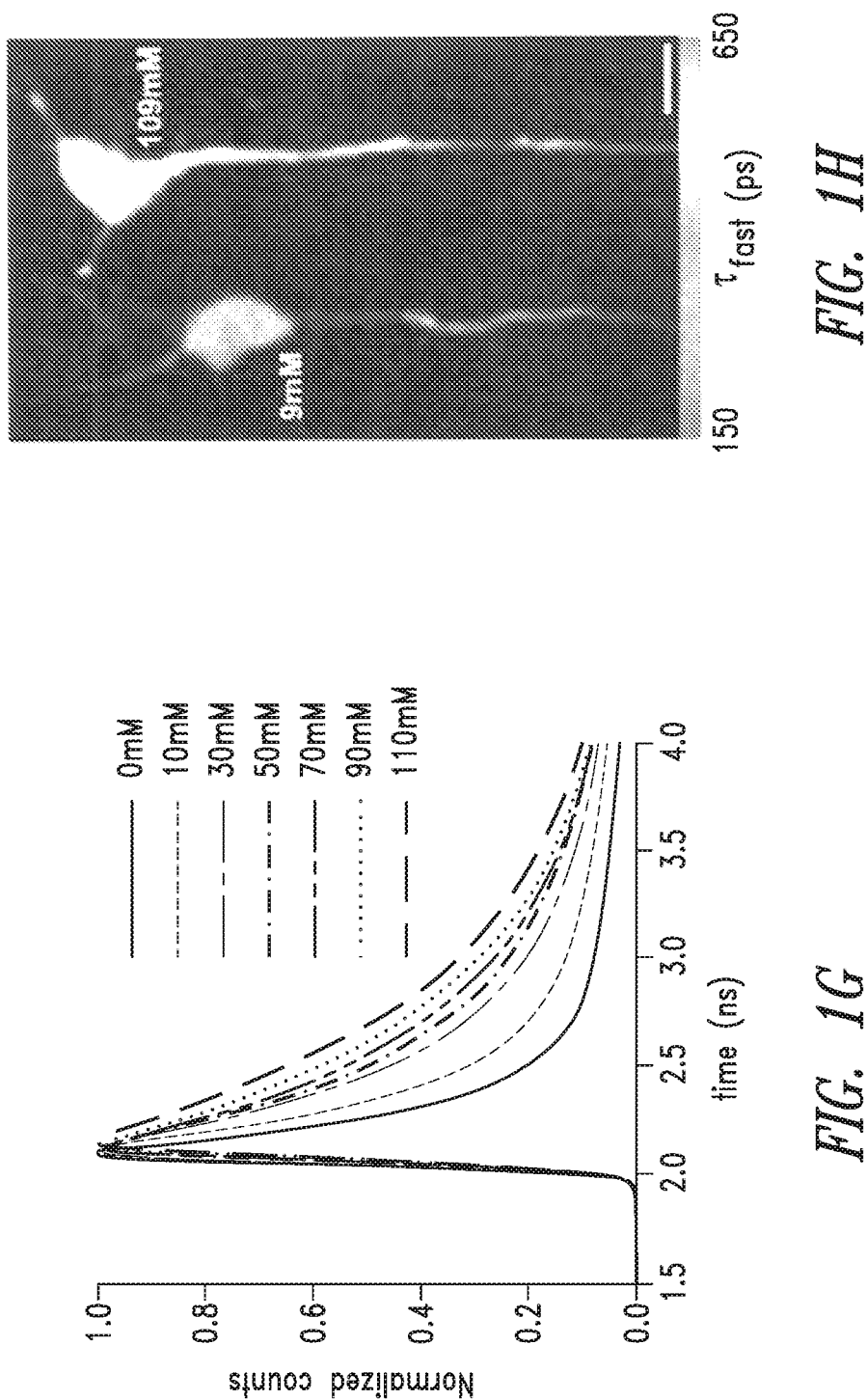
Figures 1I, 1J, 1K:
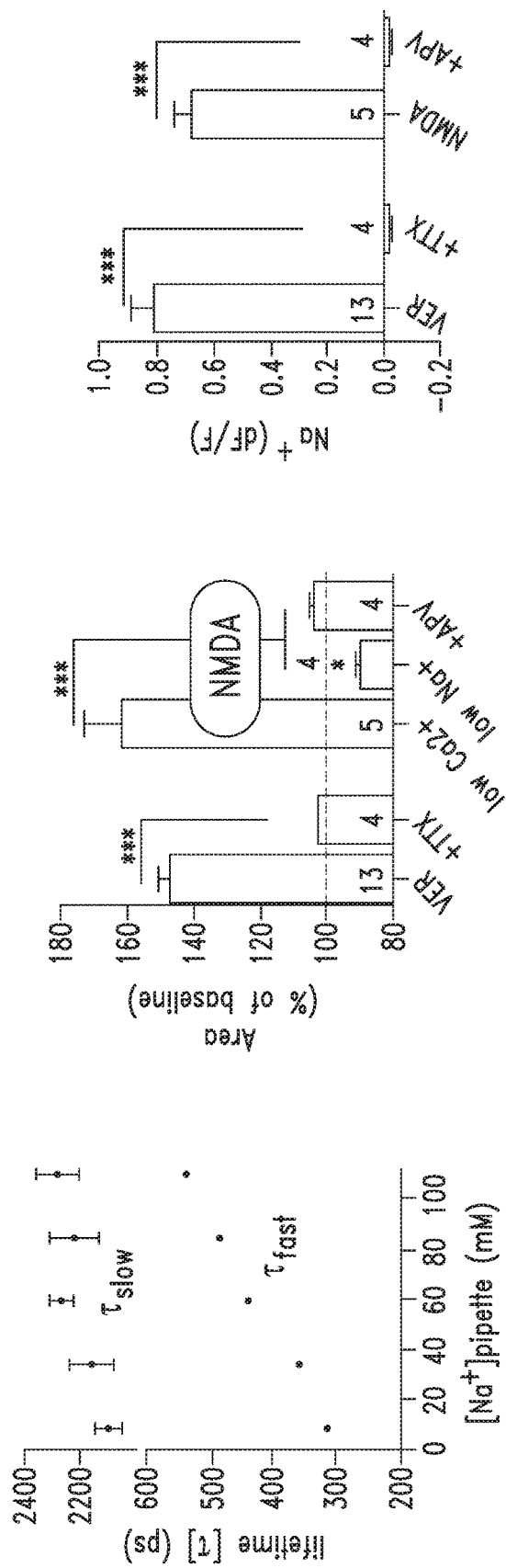
Figure 4:
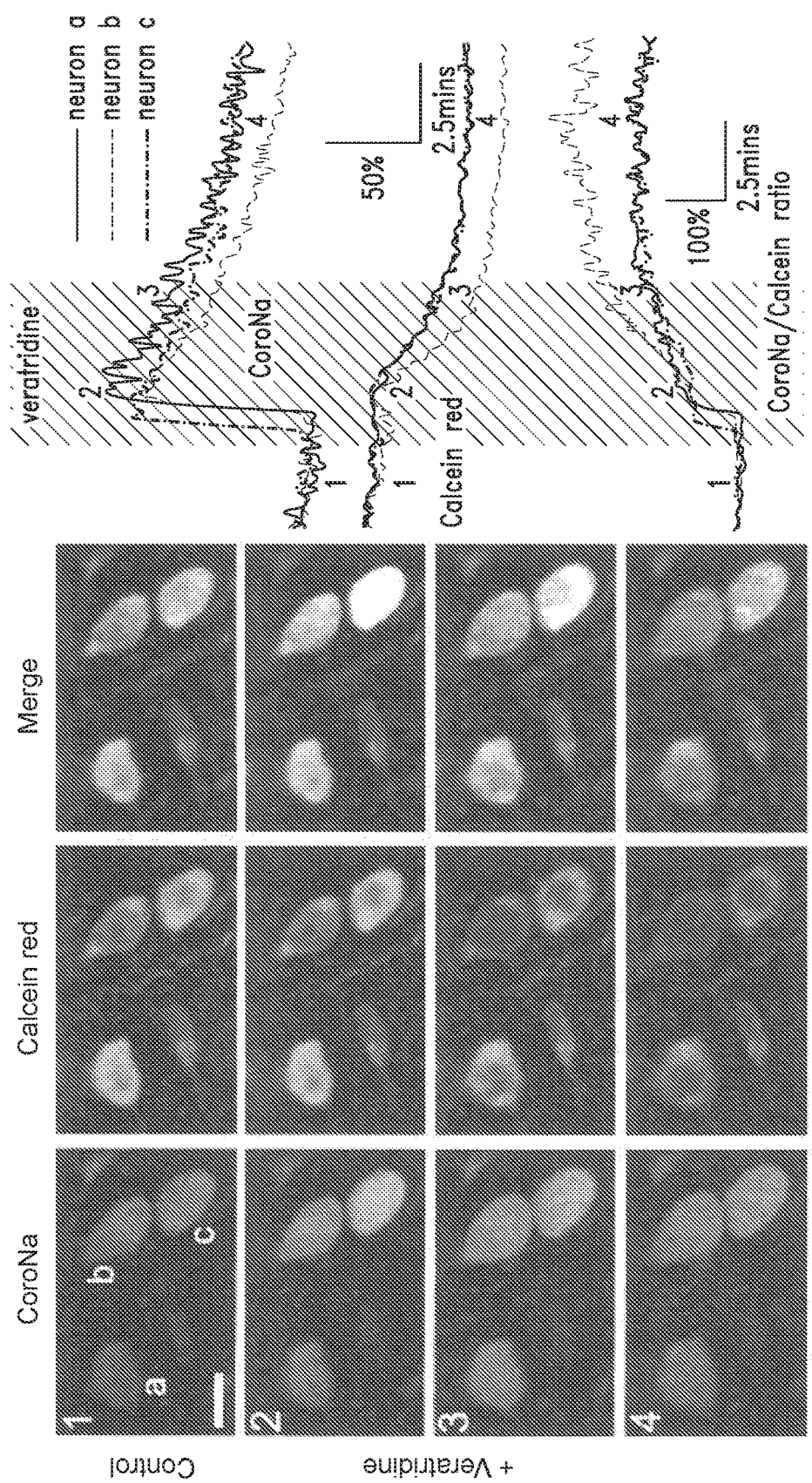
FIG. 4 shows dye dilution results in decreased fluorescence intensity as neurons swell. Left: example images of neurons loaded with CoroNa and Calcein red that were exposed to veratridine. Right: time course of CoroNa and Calcein Red signals in neurons exposed to veratridine. Scale bar, 10 µm.
Figure 5:
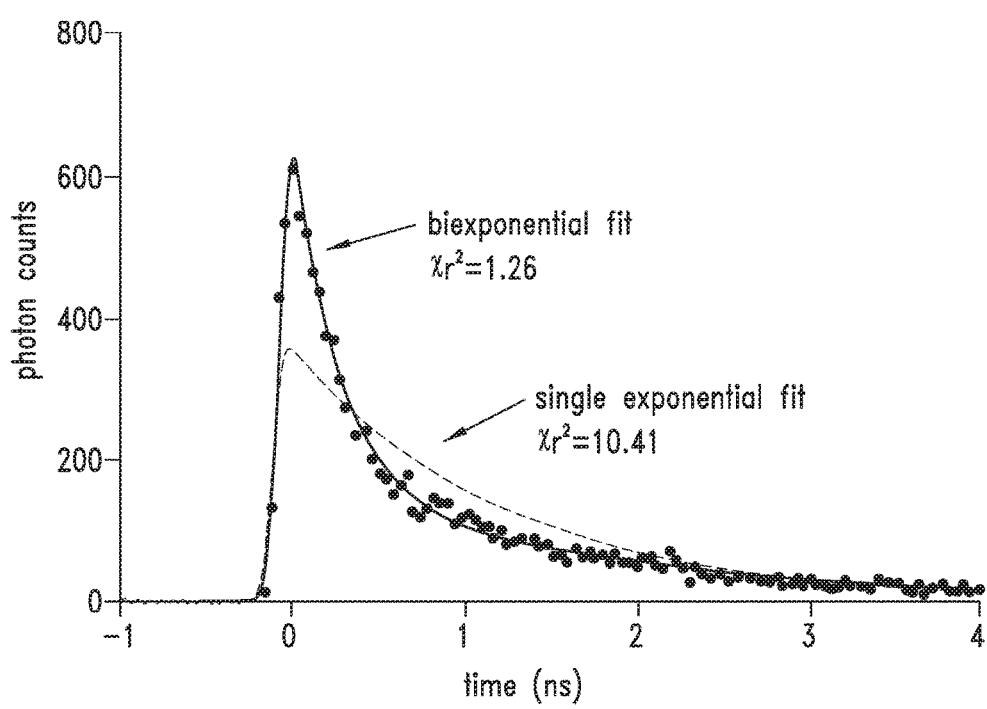
FIG. 5 shows fluorescent lifetimes were poorly fit with a single exponential, indicating decay from multiple fluorescence components and necessity for biexponential fit. Example of single and biexponential fits from a pixel within the cytosol of a cortical neuron loaded with CoroNa-AM.

Although an increase in Na$^+$ preceding swelling was consistently observed, the magnitude and duration of CoroNa fluorescence signals were distorted during cellular swelling due to dye dilution. This is consistent with our observations that swelling was associated with reduced fluorescence intensity of the inert dye, Calcein red-AM (FIG. 4). However, without the ability to dissociate changes in [Na$^+$]i from changes in dye concentration it is not possible to conclude that [Na$^+$]i itself is not also decreasing during swelling. In order to define the true magnitude and time course of the [Na$^+$]i increases, we developed a method to record real-time calibrated measurements of [Na$^+$]i using two photon fluorescence lifetime imaging (FLIM) which was independent of changes in dye concentrations. When lifetime measurements of CoroNa were first tested in iso-osmotic salt solutions the time constant of decay ($\tau$) increased with increasing [Na$^+$] (FIG. 1G). However, as the local environment can affect lifetime measurements of dyes (Berezin and Achilefu, 2010), calibrations of CoroNa lifetimes were obtained within the cytoplasm of neurons by whole cell voltage-clamping of neurons and dialysis with different [Na$^+$] concentrations. CoroNa lifetimes were best fit using a biexponential decay (FIG. 5) with a short lifetime ($\tau$fast) predictive of [Na$^+$]i (FIGS. 1H and 1I). Large deviations in $\chi^2$ from unity (i.e. $\chi^2>1.5$) typically indicate multiexponential decay resulting from multiple fluorescence components. FLIM of CoroNa loaded neurons revealed that [Na$^+$]i increased to approximately 94.46±2.14 mM (calibrated value) throughout veratridine application and gradually recovered after washout (FIGS. 1E, 1F). These results demonstrate that the decrease in CoroNa fluorescence as the neurons swell is primarily due to dye dilution and not a dilution of [Na$^+$]i itself.

Example 3

Cl$^-$ Influx is Required for Na$^+$ Induced Neuronal Swelling

Figure 6A:
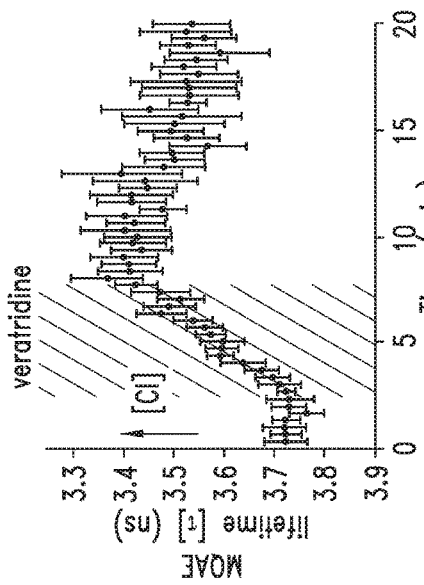
FIG. 6: $Na^+$ influx is correlated with a secondary $Cl^-$ influx that is required for neuronal swelling and causes cell death. (A and B) FLIM of $Cl^-$ sensitive dye, MQAE, shows that $Cl^-$ influx is correlated with increases in $[Na^+]i$ (n=5). (C and D) Neuronal $Na^+$ influx triggers an increase in brain tissue volume shown by changes in volume of a hippocampal brain slice. (D) Cocktail of fast glutamate receptor, GABA receptor and VGCC blockers slightly reduce tissue swelling (p<0.01) but significant $Cl^-$ dependent swelling still occurs (p<0.01) indicating that swelling is dominated by other mechanisms. (E-F) Veratridine triggered neuronal swelling is prevented by reducing extracellular $Cl^-$ (10.5 mM) and is only partially inhibited by blocking GABAARs. (G) NMDA triggered swelling is blocked by reducing extracellular $Cl^-$ (H) Positive control shows veratridine and NMDAR $Na^+$ signals were unaffected by low $Cl^-$ solution. (I) Neuronal $Na^+$ influx via VGSCs causes cell death that is $Cl^-$-dependent as measured by LDH release (J), Neuronal $Na^+$ influx via NMDARs causes cell death that is $Cl^-$-dependent and $Ca^{2+}$-independent. Scale bars, 10 µm (A), 1.0 mm (C), 15 µm (E).
Figure 6B:
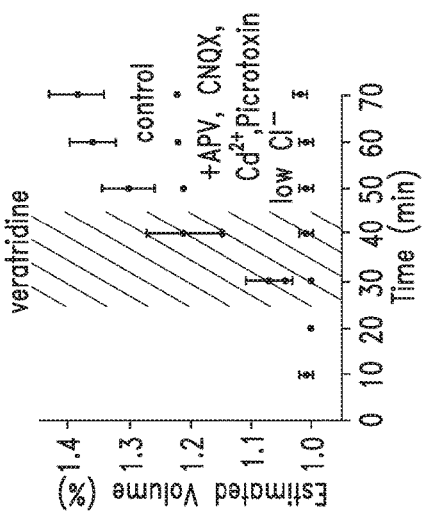

Since cytoplasmic impermeant anions make up the bulk of the intracellular anionic milieu, changes in [Cl$^-$]i must be met by an accompanying influx of water, possibly via transporters (Zeuthen, 2010), in an attempt to achieve Gibbs-Donnan equilibrium (Glykys et al., 2014). Therefore, experiments were performed to determine if prolonged [Na$^+$]i increases were associated with a secondary influx of Cl$^-$, and further whether Cl$^-$ entry was ultimately required for neuronal swelling. Using two-photon FLIM of the Cl$^-$ sensitive dye MQAE (Ferrini et al., 2013; Verkman et al., 1989) an increase in [Cl$^-$]i was observed in neurons (indicated by a decrease in the fluorescence lifetime) when Na$^+$ influx was triggered by veratridine application (FIGS. 6A and 6B). This Cl$^-$ influx was independent of entry via GABA$_A$Rs as all experiments were performed in the presence of the ligand-gated Cl$^-$ channel antagonist, picrotoxin (100 μM).

Figure 6C:
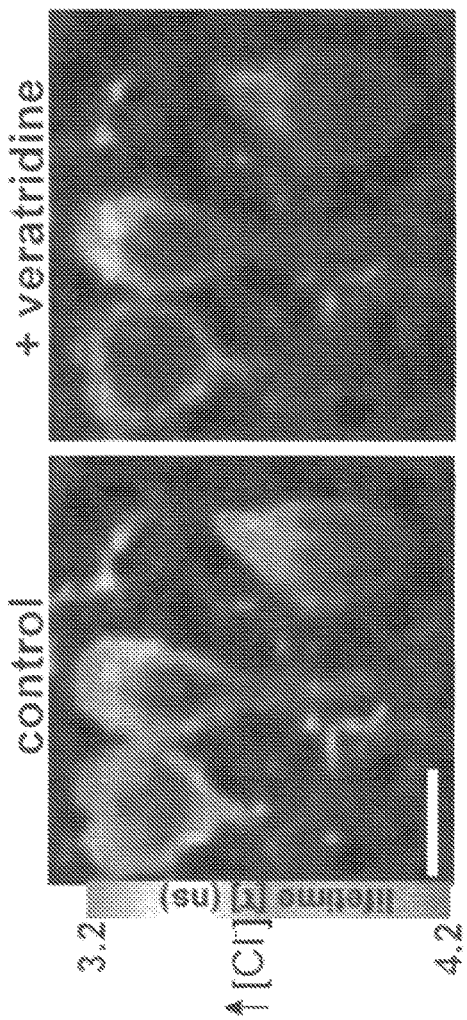
Figure 6D:
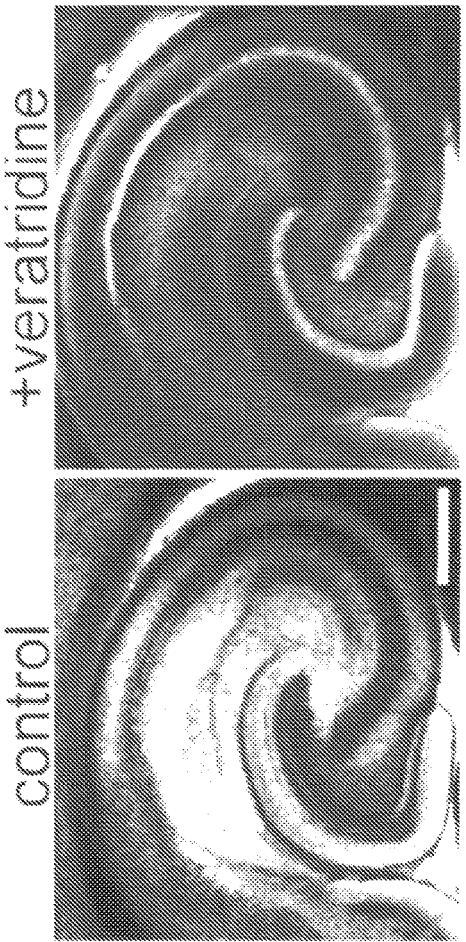

Whether neuronal Na$^+$ and subsequent Cl$^-$ influx was sufficient to increase tissue volume were next investigated by imaging hippocampal/cortical brain slices at low magnification. Application of veratridine triggered dramatic swelling of brain slices that was reduced but still substantial even when a number of Na$^+$, Ca$^{2+}$ and Cl$^-$ entry pathways were reduced by blockade of glutamate-gated AMPARs and NMDARs, voltage-gated Ca$^{2+}$ channels (VGCCs), and GABA activated Cl$^-$ channels with a cocktail of blockers (20 μM CNQX, 100 μM d-APV, 30 μM Cd$^{2+}$, and 100 μM picrotoxin) (FIGS. 6C, 6D). In contrast, blocking all Cl$^-$ influx pathways by reducing the concentration of extracellular Cl$^-$ ([Cl$^-$]ext) with iso-osmotic replacement of NaCl for Na– gluconate in the extracellular solution dramatically reduced the magnitude of the volume increase of brain slices (FIG. 6D; $p<0.001$, ANOVA). These results suggest that even when fast ionotropic glutamate and GABA activated receptors are blocked, increased neuronal [Na$^+$]i leads to cytotoxic edema of brain tissue that is dependent on Cl$^-$ influx. We next tested whether reducing [Cl$^-$]ext also prevented Na$^+$ induced swelling of individual neurons. Indeed, reducing [Cl$^-$]ext reduced the swelling of neurons visualized with CoroNa fluorescence (FIGS. 6E, 6F; $p<0.001$, ANOVA), without affecting the [Na$^+$]i signal (FIG. 6H; $p>0.05$, two-tailed student's t test). As it has been previously reported that GABAAR mediated Cl$^-$ influx can contribute to both neuronal swelling in cell culture (Hasbani et al., 1998) and to swelling following oxygen glucose deprivation in situ (Allen et al., 2004), the contribution of GABAAR Cl$^-$ influx to neuronal swelling in our experimental conditions was examined. Consistent with previous reports, pre-application of the GABAAR antagonist picrotoxin slightly but significantly reduced the magnitude of neuronal swelling (from 161.7% to 146.9%; FIG. 6F; $p<0.05$, ANOVA), however, the majority of the volume increase persisted in picrotoxin suggesting that the cause of swelling was dominated by Cl$^-$ influx via an as yet unidentified mechanism. NMDA-induced swelling was also blocked by low [Cl$^-$]ext (iso-osmotic replacement of NaCl for Na-isethionate) (FIG. 6G; $p<0.05$, two-tailed student's t test). Together, these data indicate that neuronal swelling requires Cl$^-$ influx through a mechanism that is triggered by an increase in [Na$^+$]i and that Na$^+$ entry alone is not sufficient to swell neurons. For the experiments displayed in FIG. 6, slices were incubated in low [Cl$^-$]o or control ACSF for the entire experiment starting 20 min. prior to either Veratridine or NMDA (15 min.). LDH was collected from supernatant 1.5 hours following end of Veratridine or NMDA treatment. For experiments in (A, B, E and G–J) solutions contained blockers: 30 μM Cd$^{2+}$, 20 μM CNQX, 100 μM picrotoxin, plus either 100 μM APV for veratridine experiments or 1 μM TTX for NMDA experiments. n values in (F), blockers (n=5), $^+$picrotoxin (n=13), low Cl$^-$ (n=5). VER, veratridine; VGCC, voltage gated calcium channel; VGSC, voltage gated sodium channel. Error bars and shaded region above and below the mean represent SEM.

Example 4

Cl$^-$ Influx is Required for Na$^+$ Induced Neuronal Swelling

Aberrant calcium influx via NMDARs can lead to mitochondrial depolarization and cell death, however, Cl$^-$ removal also reduces ischemia and glutamate evoked early neuronal death in cell culture (Choi, 1987; Goldberg and Choi, 1993; Rothman, 1985), suggesting the existence of two independent pathways ultimately leading to cell death. The impact of the [Na$^+$]i-triggered Cl$^-$ entry and neuronal swelling on cell viability was further investigated using LDH release as a measure of cell death (e.g. (Kajta et al., 2005)). Even in the combined presence of CNQX, picrotoxin and $Cd^{2+}$ to block fast AMPA/KA receptors, GABA-activated $Cl^-$ channels and VGCCs respectively, application (15 min) of either veratridine (50 µM) or NMDA (100 µM, in artificial cerebrospinal fluid (ACSF) containing 0 mM $Ca^{2+}$ and 2 mM EGTA) caused a rapid and significant increase in LDH release indicating neurons were dying after 90 min (FIGS. 6I and 6J; p<0.01, ANOVA). Both the NMDA-induced and veratridine-induced neuronal death, as indicated by LDH release, were abolished by reducing [$Cl^-$]ext throughout the experiment (FIGS. 6I and 6J; p<0.01, ANOVA). This suggests that $Na^+$-induced $Cl^-$ influx and subsequent swelling results in $Ca^{2+}$-independent cell death.

Example 5

Figure 7A:
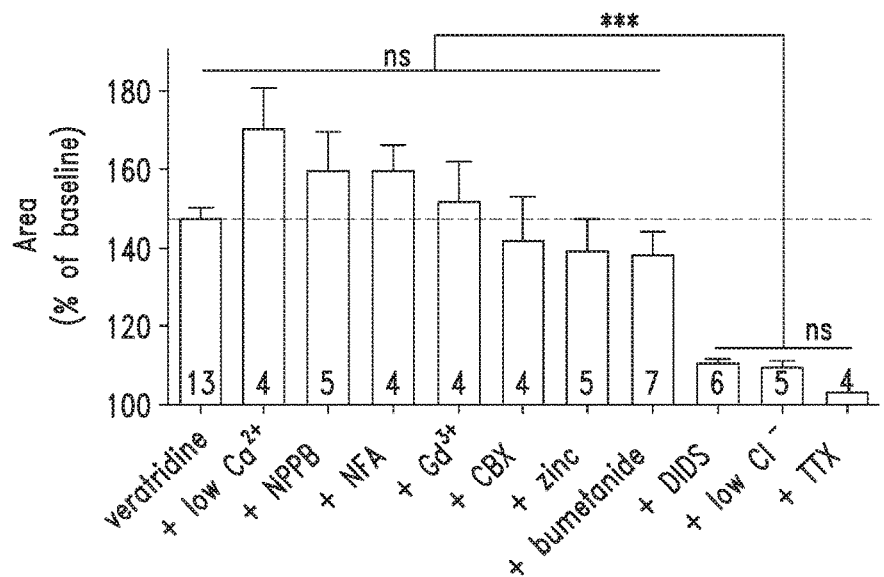
FIG. 7 shows that neuronal swelling shows the pharmacological profile of a SLC4 or SLC26 family member. (A) Veratridine induced neuronal swelling was blocked by DIDS. (B) Positive control shows veratridine and NMDA induced $Na^+$ signal in the presence of DIDS. (C) NMDA induced neuronal swelling was blocked by DIDS in a dose dependent manner; control (n=5), 250 µM (n=4), 500 µM (n=5), 1 mM (n=5). Error bars and shaded region above and below the mean represent SEM.
Figure 7B:
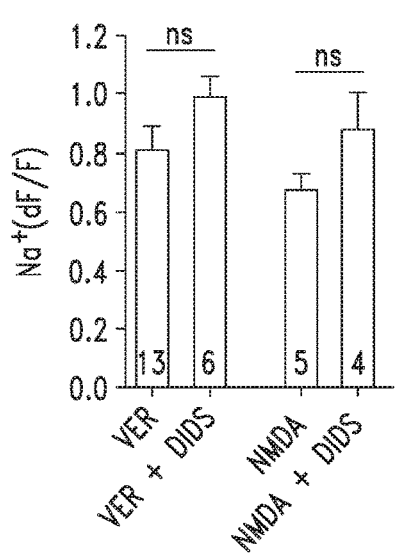
Figure 7C:
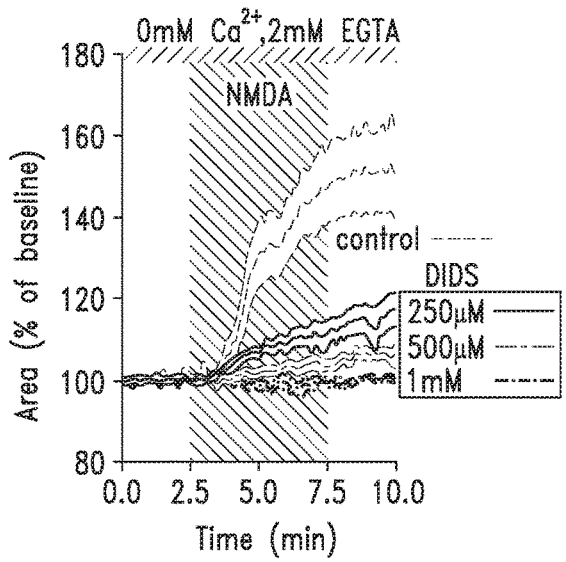

Pharmacological Analyses of the Predominant $Cl^-$ Influx Pathway Required for Neuronal Swelling and Death There are several candidates for the transmembrane influx of $Cl^-$ in neurons that can be distinguished based on their sensitivity to different antagonists (Alvarez-Leefmans and Delpire, 2009; Jentsch et al., 2002; Verkman and Galietta, 2009) (Table E1). Candidate neuronal $Cl^-$ transporters were evaluated to determine if the $Cl^-$ transporter could be identified, and further, if blocking the source of $Cl^-$ entry that was triggered by $Na^+$ entry could prevent both the $Na^+$ induced neuronal swelling and corresponding cell death. As a first step, pharmacological analyses using the imaging assay of neuron swelling in brain slices were undertaken in order to screen for the possible involvement of different $Cl^-$ channels and transporters. In separate experiments the following blockers were tested as described in Table E3; NPPB (200 µM) to block the volume-regulated anion channel (VRAC, VSOR), zinc (300 µM) to block CLC-2, $Gd^{3+}$ (100 µM) to block the Maxi-anion channel, niflumic acid (NFA) (200 µM) to block the $Ca^{2+}$ activated $Cl^-$ conductance (CaCC, bestrophin), carbenoxelone (CBX) (100 µM) to block pannexins/connexins, bumetanide (100 µM) to block cation chloride cotransporters (NKCC1 and KCC2), and DIDS (250 µM) to block SLC4 and SLC26 anion exchangers. All antagonists were both bath applied and present in the puffing pipette used to apply either NMDA or veratridine. Of note, of the various $Cl^-$ channel and transporter blockers examined only DIDS reduced the swelling induced by increased [$Na^+$]i (FIG. 7A; p<0.05 compared to all other antagonists, ANOVA). The small volume change in the presence of DIDS was not significantly different from those observed in low $Cl^-$ extracellular solution (FIG. 7A; p>0.05, ANOVA). A substantial [$Na^+$]i increase was still observed in DIDS indicating that $Na^+$ entry was not affected (FIG. 7B). This pattern of block by DIDS but no effect of the numerous other blockers suggested that a member of the SLC4 or SLC26 families of anion exchangers was the most likely source of $Cl^-$ entry. Although DIDS also blocks VRAC, which has been implicated in excitotoxic cell death in neuronal cell culture (Inoue and Okada, 2007), under our conditions we observed no protection of either cell volume or cell death in the presence of the potent VRAC blocker, NPPB. DIDS also blocked NMDA-evoked neuronal swelling in a dose-dependent manner (FIG. 7C), and was confirmed to block the veratridine-stimulated swelling at 37° C. (FIG. 3), suggesting a common mechanism. For all experiments displayed in FIG. 7, all solutions contained blockers: 30 mM $Cd^{2+}$, 20 µM CNQX, 100 µM picrotoxin, plus either 100 µM d-APV for veratridine experiments or 1 µM TTX for NMDA experiments. VER, veratridine; AZM, acetazolamide.

Figures 8A, 8B, 8C:
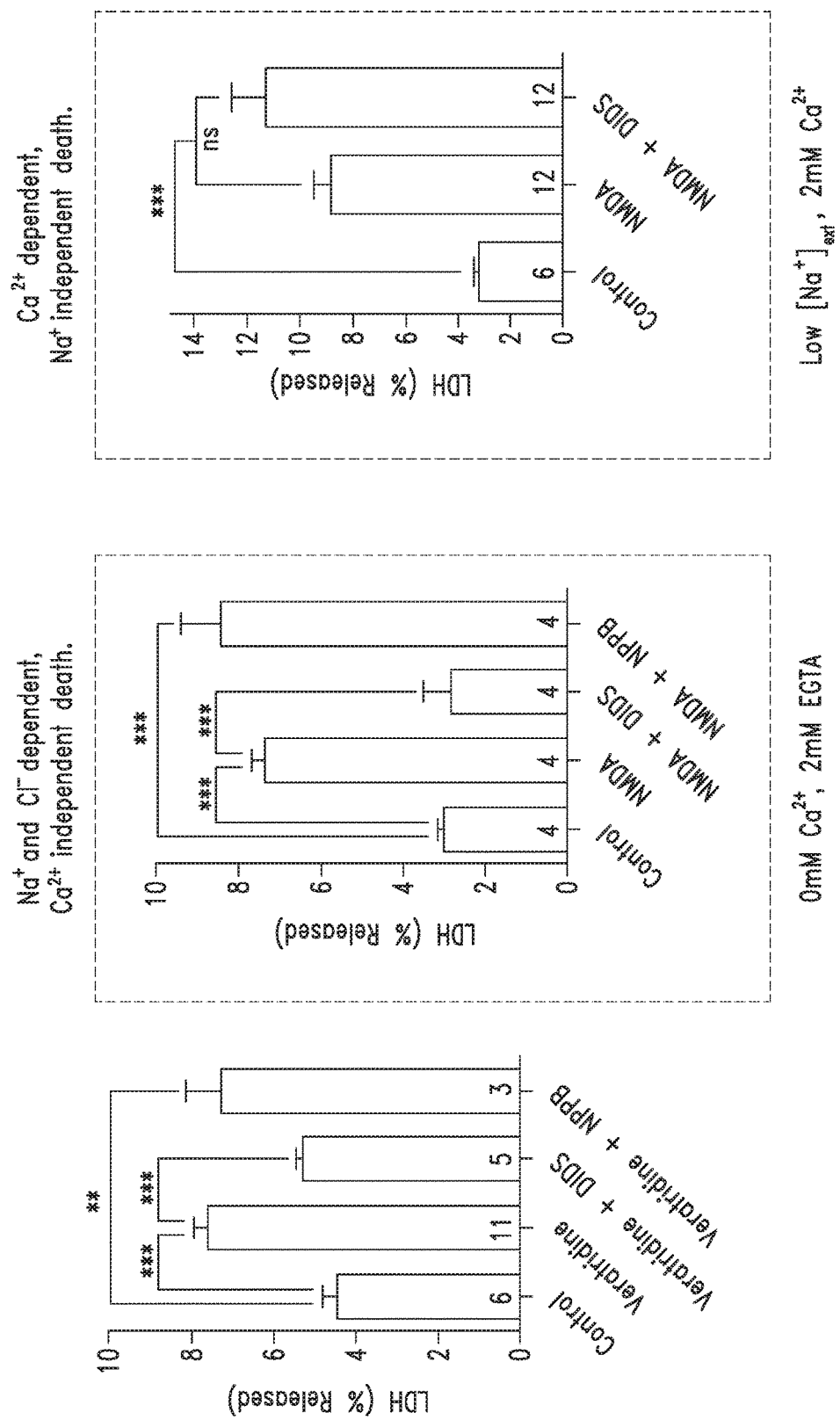
FIG. 8 shows that DIDS blocks $Na^+$ and $Cl^-$ dependent, $Ca^{2+}$ independent cell death. (A) LDH release measurements show $Na^+$- and $Cl^-$-dependent cell death triggered by veratridine was blocked by DIDS but not by NPPB. (B) NMDAR $Na^+$ influx triggers cell death in the absence of extracellular $Ca^{2+}$ that is blocked by DIDS but not NPPB. (C) NMDAR $Ca^{2+}$ influx also triggers cell death that is not blocked by DIDS, indicating separate pathways.

As it was observed that extracellular $Cl^-$ was required for both neuronal swelling and the subsequent cell death and that DIDS prevented neuronal swelling, we predicted that DIDS would block the $Cl^-$ dependent cell death pathway without affecting the classic $Ca^{2+}$-dependent death. DIDS was initially tested for its effectiveness in preventing the swelling-induced, $Cl^-$-dependent cell death as measured by LDH efflux in brain slices exposed to veratridine. Indeed, DIDS prevented cell death from veratridine induced $Na^+$ influx and swelling (FIG. 8A; p<0.005, ANOVA), whereas the VRAC blocker NPPB had no effect. DIDS was further examined on both the NMDA $Cl^-$-dependent, $Ca^{2+}$-independent cell death pathway and on the NMDA $Ca^{2+}$-dependent cell death pathway. As predicted, DIDS blocked the cell death caused by NMDA in $Ca^{2+}$ free extracellular solution (FIG. 8B; p<0.005, ANOVA). If however, NMDA was applied in the presence of extracellular $Ca^{2+}$ but reduced extracellular $Na^+$, cell death still occurred (FIG. 8C; p<0.005, ANOVA) but was not blocked by DIDS (FIG. 8C; p>0.05, ANOVA). These results suggest that two independent cell death pathways co-exist that can be distinguished based on their ionic basis; one that involves swelling, requires $Na^+$ and $Cl^-$ influx, is $Ca^{2+}$-independent and is blocked by DIDS, and one that is triggered by $Ca^{2+}$ influx, but that is not DIDS sensitive.

TABLE E1

| Channel/Transporter | Agonist and concentration | | | | | | |
|---|---|---|---|---|---|---|---|
| | NPPB (200 µM) | NFA (200 µM) | $Gd^{3+}$ (100 µM) | CBX (100 µM) | Zinc (300 µM) | Bumetanide (100 µM) | DIDS (250 µM) |
| VRAC | 40-100 µM | | | | | | 100-400 µM |
| CaCC | 100 µM | 50-100 µM | | | | | |
| Maxi-Anion Channel | 100 µM | | 30-50 µM | | | | 100 µM |
| Pannexins, Connexins | | | | 100 µM | | | |
| CLC-2 | | | | | 100 µM | | |
| NKCC1 | | | | | | Ki ~0.1 µM | |
| KCC2 | | | | | | Ki ~25-50 µM | |
| SLC4-A3, A8, A10 | | | | | | | 0.1-0.5 mM |
| SLC26A11 | | | | | | | 0.5-1 mM |

Example 6

Identification of Slc26A11 as the Predominant Cl⁻ Influx Pathway Underlying Na⁺ Dependent Cytotoxic Neuronal Swelling Data presented herein indicates that $Na^+$ entry into neurons is linked to a DIDS-sensitive $Cl^-$ influx pathway that is required for neuronal swelling and mediates cell death. Several $DIDS^-$ sensitive candidates are expressed in central nervous system (CNS) neurons of which several act as $Cl^-/HCO^{3-}$ exchangers and include the SLC4 family of exchangers (Alvarez-Leefmans and Delpire, 2009; Boron et al., 2009; Romero et al., 2013). The DIDS-sensitive $Cl^-/HCO^{3-}$ exchangers that are known to be expressed in the cortex and hippocampus are SLC4A3, SLC4A8 and SLC4A10. In addition, SLC26A11 was recently shown to be highly expressed in CNS cortical neurons (Rahmati et al., 2013). SLC26A11 is a member of the sulfate transporter family that in different expression systems has been reported to act variously as a DIDS-sensitive sulfate transporter, a DIDS-sensitive exchanger for $Cl^-$, $SO_4^{2-}$, $HCO^{3-}$ or $H^+$—$Cl^-$ or as a $Cl^-$ channel (Lee et al., 2012; Rahmati et al., 2013; Vincourt et al., 2003; Xu et al., 2011).

Figure 9B:
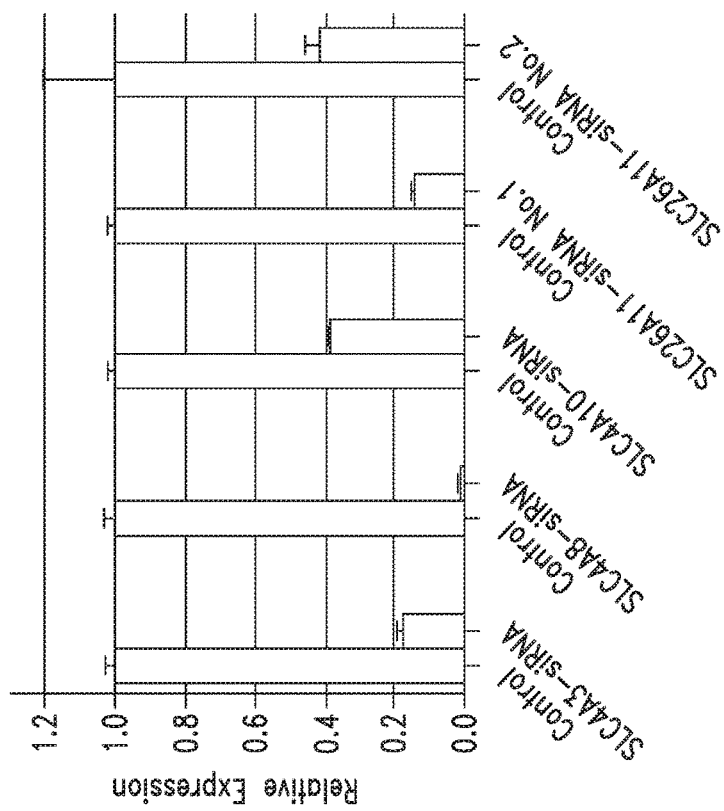
FIG. 9 shows SLC26A and SLC4A gene families, siRNA-mediated knockdown and expression profiles. (A) Protein sequence similarity tree of the SLC26A and SLC4A family members from mouse, rat and humans. (CaV=voltage-gated calcium channels CaV1.2, CaV2.1 and CaV3.1 from human). (B) Testing of LNP-packaged modified Dicer siRNA knockdown duplexes (for SLC4A3, SLC4A8, SLC4A10 and SLC26A11) in vitro. (C) Expression profiles of the SLC4A and SLC26A family members in rat cortex and hippocampus as determined using qPCR.
Figure 9A:
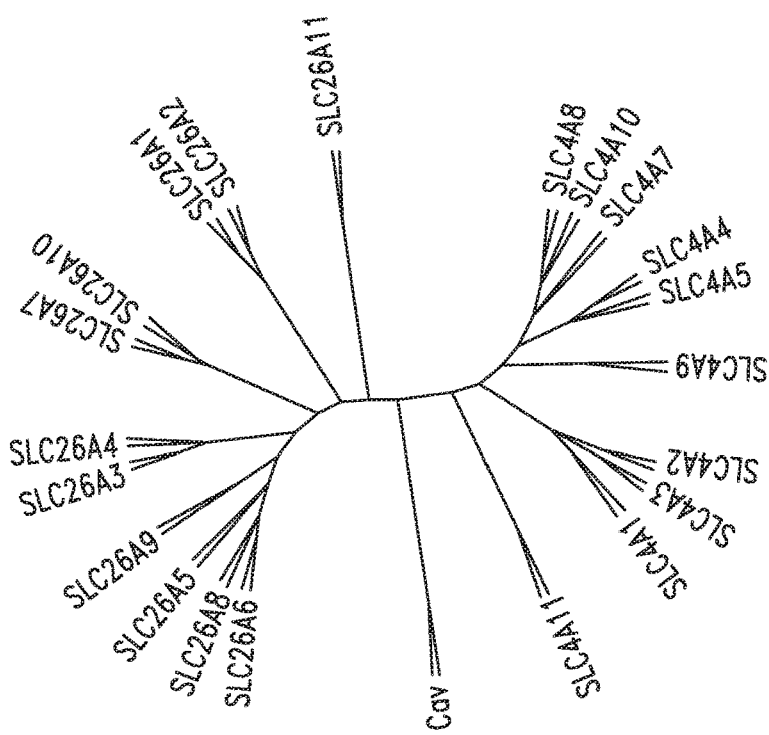
Figure 9C:
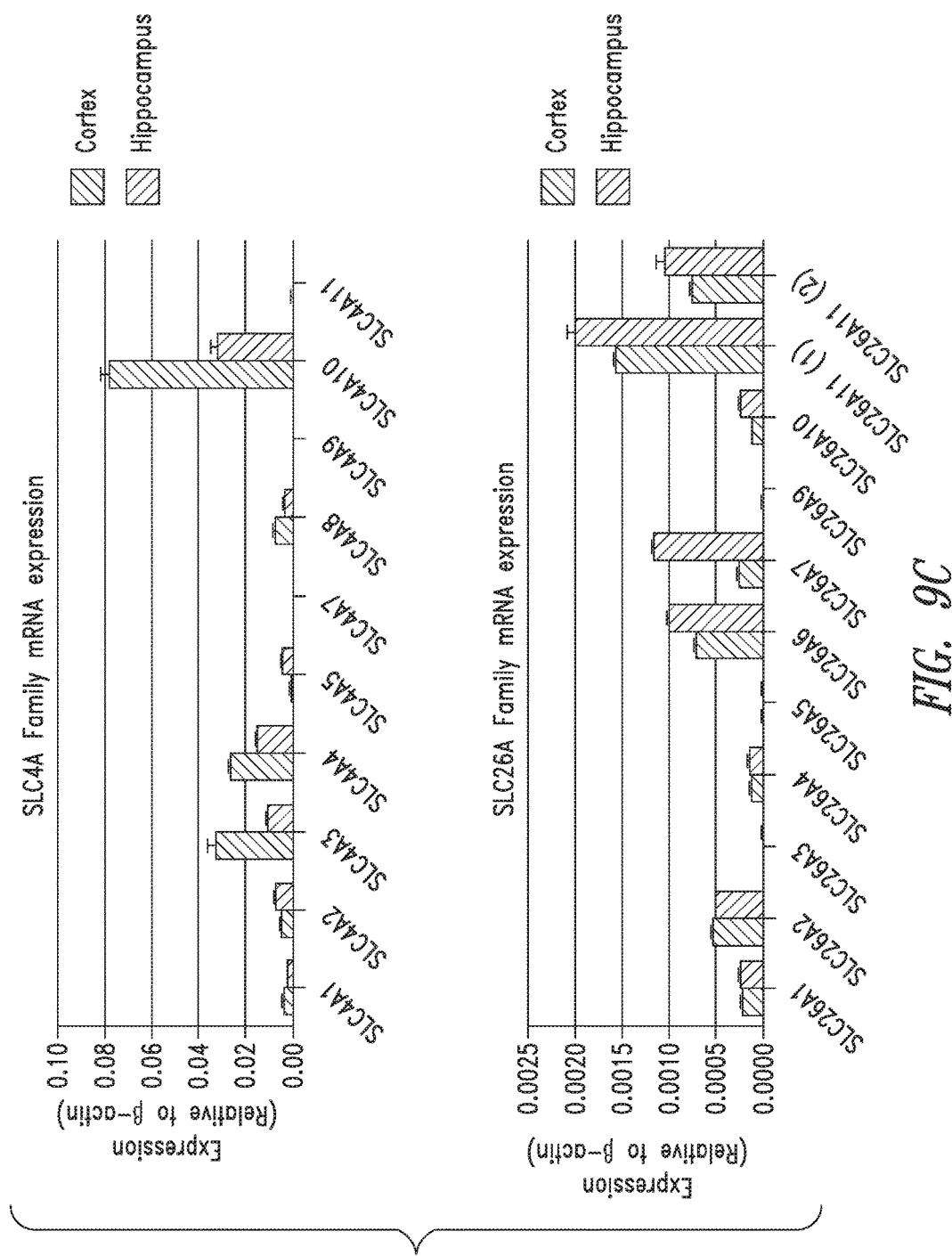
Figure 10A:
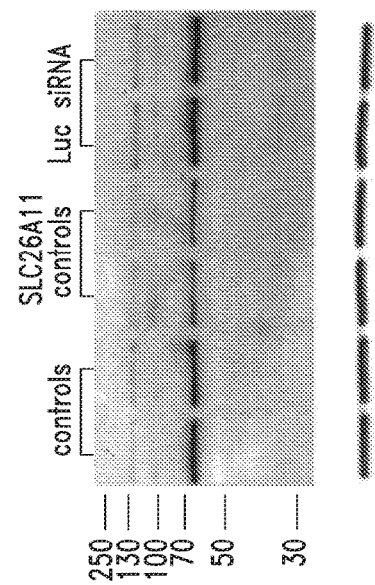
FIG. 10 shows $Cl^-$ influx via SLC26A11 causes cytotoxic neuronal edema following increased $[Na^+]i$. (A and B) shows SLC26A11 No. 1 siRNA selectively reduced SLC26A11 protein expression compared to β-actin. Controls show luciferase siRNA had no effect on SLC26A11 expression. Columns in (A) represent samples from different rats. (C) In vivo knockdown of SLC4A3, A8, A10 with LNP-siRNAs results in no significant difference in the magnitude of neuronal swelling compared to a control (luciferase siRNA) in cortical brain slices following the injection (p>0.05, ANOVA). (D) Two different siRNA constructs against SLC26A11 result in a significant reduction in the magnitude of veratridine induced neuronal swelling compared to luciferase siRNA (p<0.05, ANOVA). (G and H) Images of cortical neurons transfected with siRNA using lipid nanoparticle delivery shows SLC26A11 knock down results in protection from veratridine triggered swelling compared to neurons transfected with SLC4A8 siRNA. (E) SLC26A11 blocker $GlyH^-101$ significantly reduces the magnitude of neuronal swelling induced by increases in $[Na^+]i$, p<0.001, two$^-$ tailed student's t test (F) and the resulting cell death measured by LDH released, p<0.001, ANOVA.
Figure 10B:
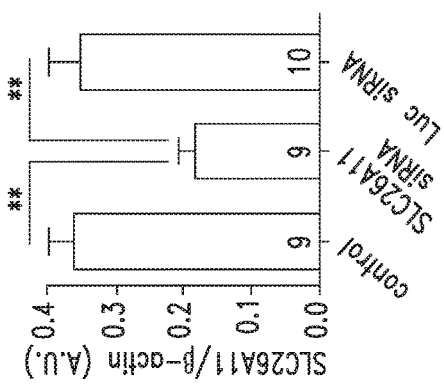
Figure 10C:
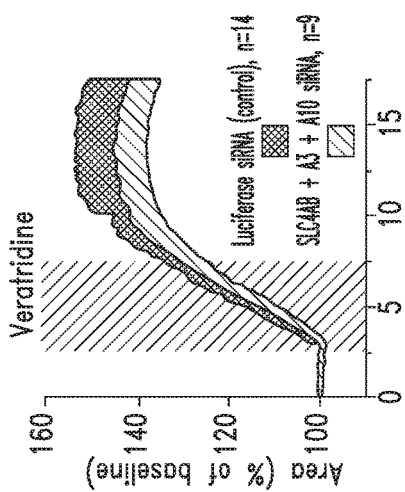
Figure 10D:
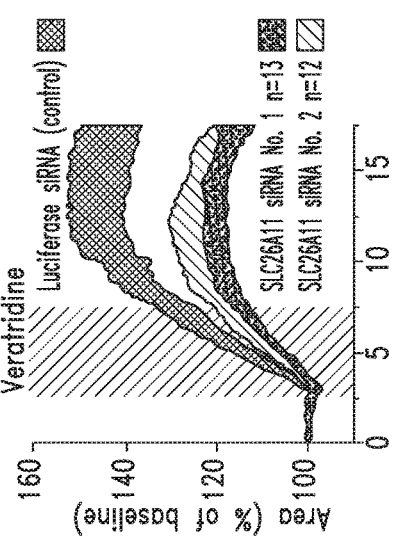
Figure 10E:
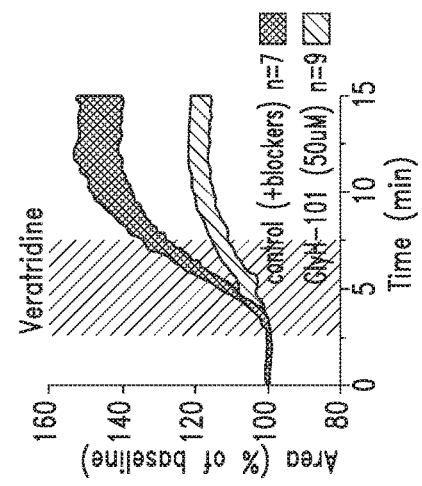
Figure 10F:
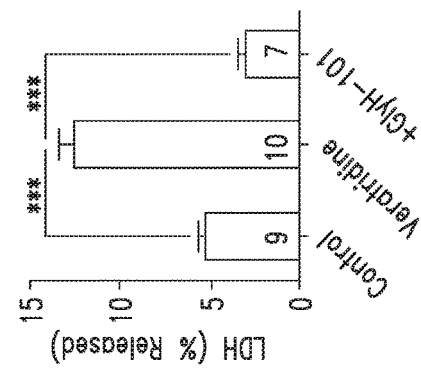
Figures 10G, 10H:
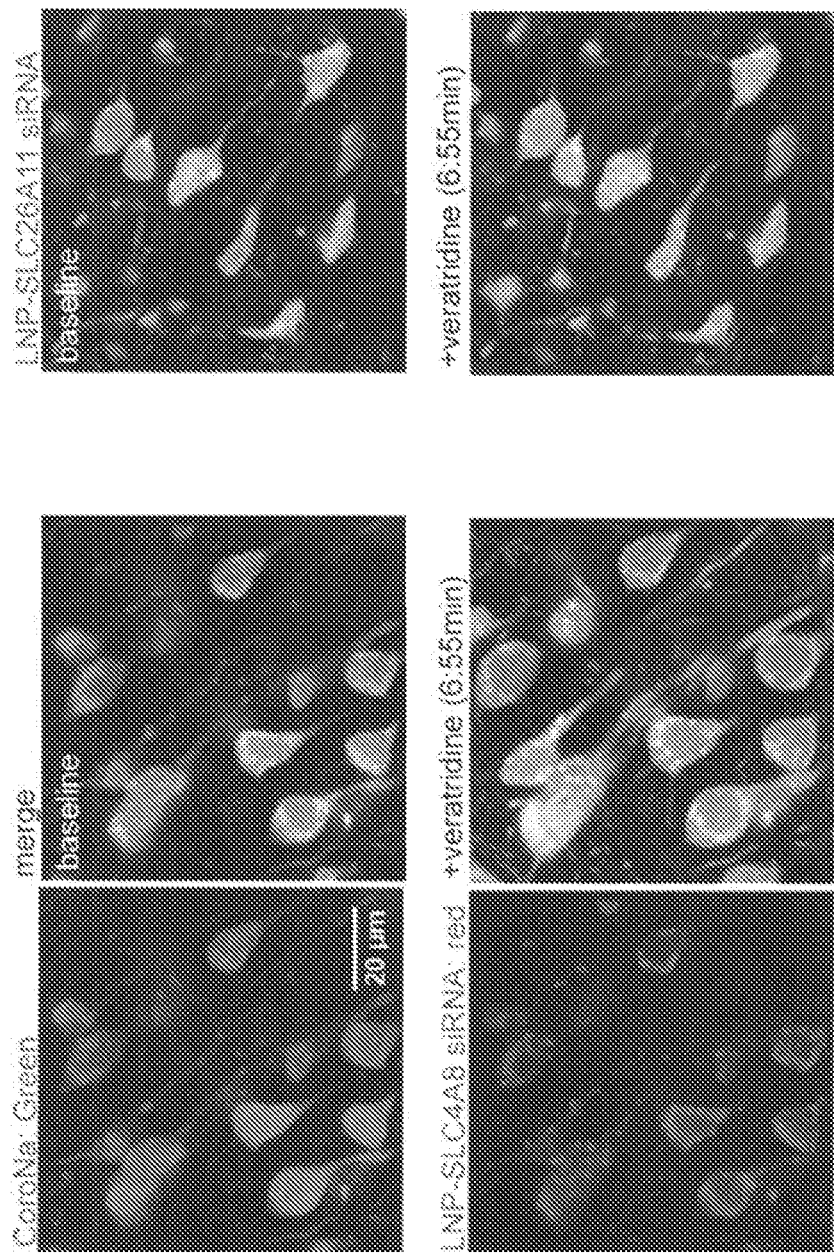
Figure 12:
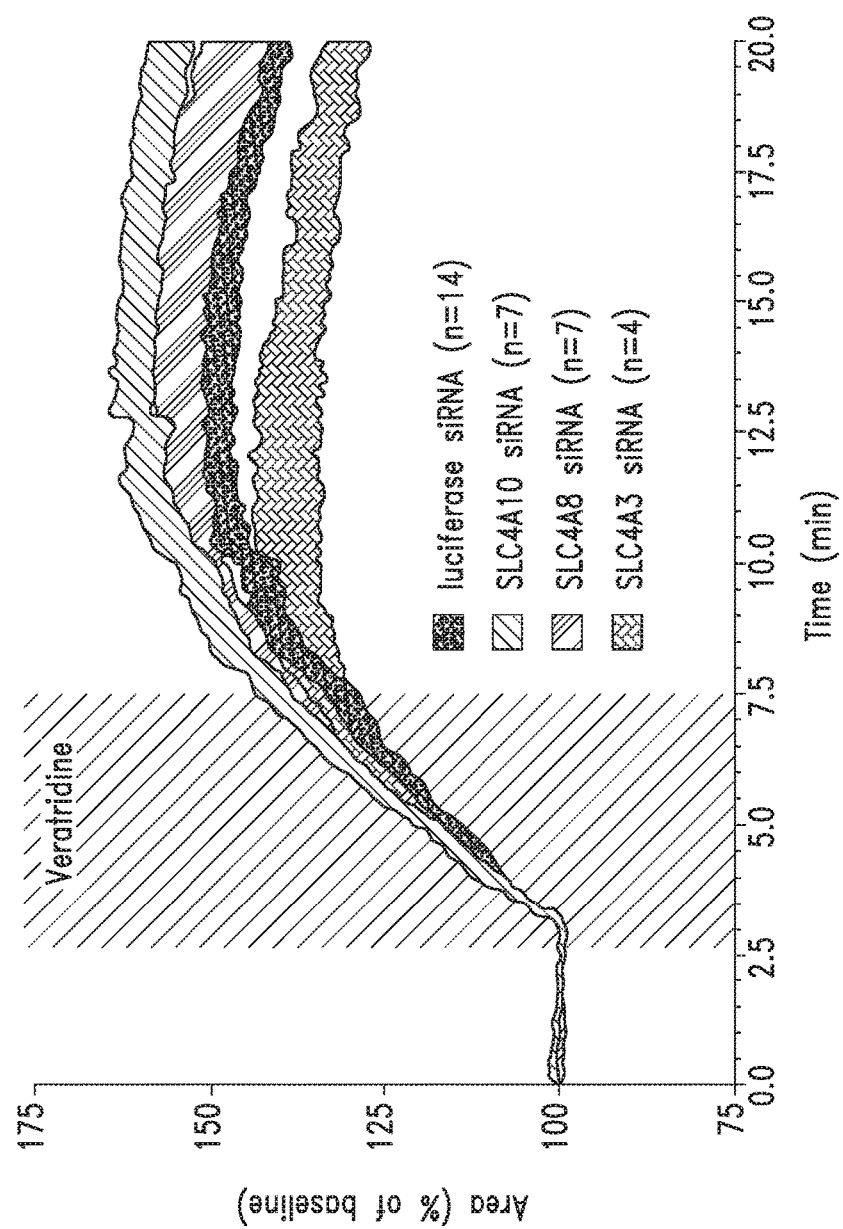
FIG. 12 shows siRNA-mediated knockdown of individual SLC4A family members does not alter the magnitude of neuronal swelling.

Utilizing qRT-PCR, the expression of SLC4 and SLC26 family members was confirmed in both cortical and hippocampal brain tissue (FIG. 9). The data in FIG. 9 represent quantification using qPCR 72 hrs post-treatment of cultured rat cortical neurons except for unmodified SLC4A10 Dicer siRNA which was tested in HEK293 cells expressing the cloned rSLC4A10 target. Data are normalized to internal rGAPDH mRNA levels. Based on their combined pharmacological profile and expression profiles, SLC4-A3, -A8, -A10 and SLC26A11 appeared to be the most promising candidates for the $Cl^-$ entry pathway that causes neuronal swelling. The development of an efficient lipid nanoparticle (LNP)-mediated delivery system to introduce siRNAs against specific molecular targets into CNS neurons both in vivo and in vitro has recently been reported (Rungta et al., 2013). Individual siRNAs targeted against the different SLC candidate genes were encapsulated in DiI labeled LNPs and initially tested for their ability to attenuate expression in both primary neuron cultures and a HEK cell expression system (FIG. 9.) These in vitro-validated siRNA LNPs against the 4 different SLC candidates or a control (luciferase) siRNA were subsequently injected intracranially into the rat somatosensory cortex. After allowing 5-6 days for uptake of LNPs and knockdown of candidate proteins to occur, neurons that had taken up DiI labeled LNPs were examined for $Na^+$ induced $Cl^-$-dependent swelling in cortical slices. Knockdown of SLC4A-3, -8 or -10 either separately or together had no significant effect on the magnitude of veratridine-induced neuronal swelling compared to the control luciferase siRNA injected animals (FIGS. 10C, 10G and 12; p>0.05, ANOVA). In striking contrast, knockdown of SLC26A11 with two siRNAs targeted towards different sequences of SLC26A11 mRNA, significantly reduced the magnitude of the swelling in neurons (FIGS. 10D and 10H; p<0.05, ANOVA was performed comparing results from all siRNA groups (luciferase, A3, A8, A10, A3+A8+A10, A11 No. 1 and A11 No. 2)). Luciferase controls were combined and plotted in FIGS. 10C, 10D and FIG. 12. Only SLC26A11 No. 1 and No. 2 were significantly different from luciferase (control) siRNA. The occurrence of SLC26A11 knockdown was further validated by Western Blot analysis of SLC26A11 protein in tissue 5 days following injection of SLC26A11 siRNA-LNPs (FIGS. 10A and B). These results indicate that the $Cl^-$ influx that is required for neuronal swelling is mediated by a SLC26A11-dependent process.

Studies of the properties of recombinant SLC26A11 have shown that, depending upon the cell type it is expressed, this protein can act either as a $Cl^-$ channel or a $SO_4^{2-}$ or oxalate transporter that is inhibited by DIDS or the CFTR antagonist GlyH-101 (Alper and Sharma, 2013; Rahmati et al., 2013; Stewart et al., 2011). We therefore investigated whether GlyH-101 has similar actions on preventing neuronal swelling and the associated cell death and whether there exists a neuronal $Cl^-$ current that is sensitive to both DIDS and GlyH-101. Similar to the actions of DIDS, GlyH-101 profoundly inhibited both veratridine-stimulated swelling (FIG. 10E; p<0.001, two-tailed Student's t test) and cell death (FIG. 10F; p<0.001, ANOVA).

Figure 11B:
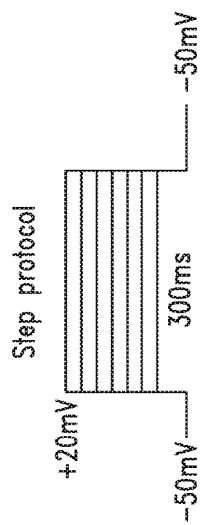
FIG. 11 shows that the SLC26A11 gene product is required for activation of an outwardly rectifying $Cl^-$ channel that is activated by depolarization. (A) Image of a whole cell voltage-clamped layer 4 neuron in a coronal brain slice. (B) Voltage clamp protocol used to depolarize neuron in presence of a cocktail to inhibit known voltage-dependent ion channels. (C) Left: Top, Example trace of outward current activated by depolarization. Middle, magnitude of current is reduced in DIDS. Bottom, subtraction showing DIDS-sensitive component. Right: SLC26A11 siRNA transfection attenuates DIDS sensitive outward current. (D,E) Summarized I/V curves demonstrate that SLC26A11 is required for activation of an outward $Cl^-$ conductance that is activated in depolarized neurons.
Figure 11A:
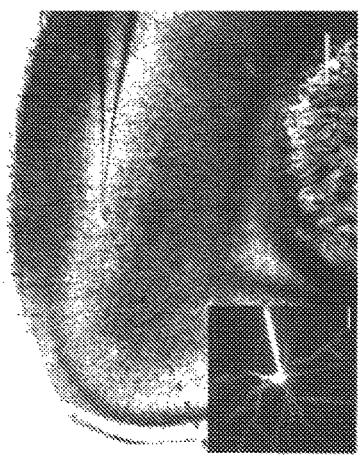
Figure 11C:
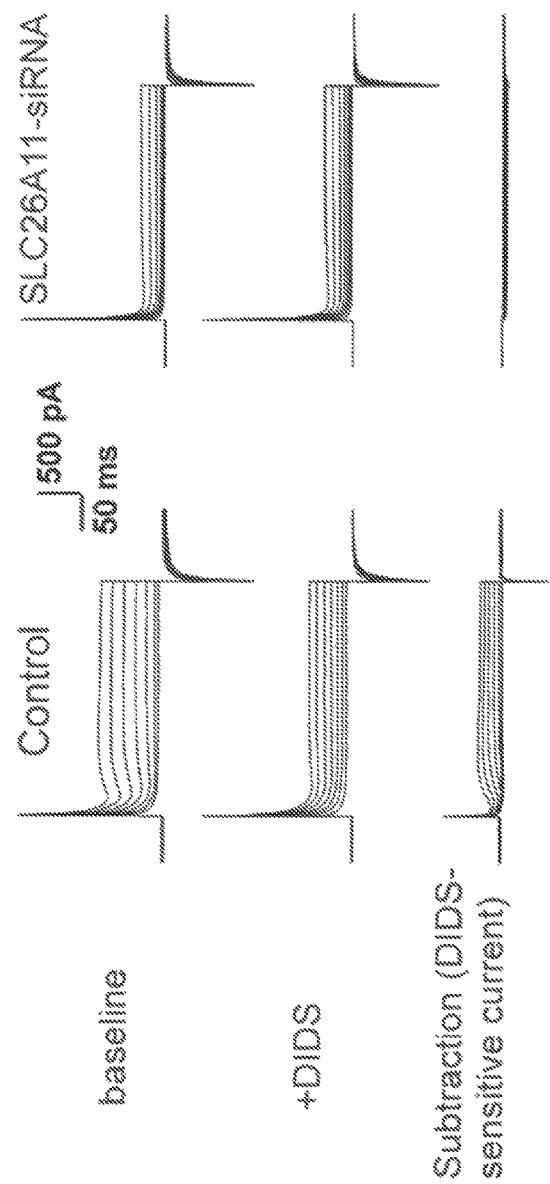
Figures 11D, 11E:
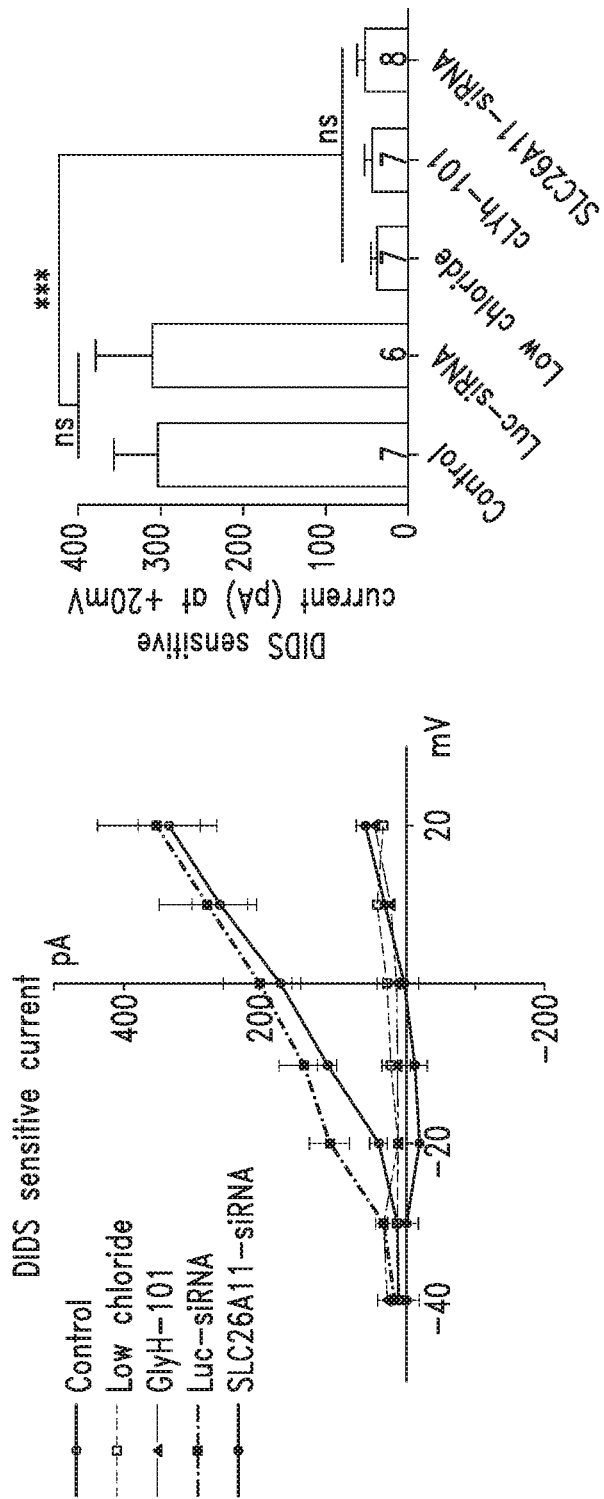

The opening of $Na^+$ permeable channels causes both $[Na^+]i$ accumulation and neuronal depolarization. The large (~80 mM) increases in $[Na^+]i$ occurred prior to the increases in cell volume (FIG. 1) suggesting that there are compensatory mechanisms such as $K^+$ efflux that are initially sufficient to maintain osmotic equilibrium. However progressive accumulation of extracellular $K^+$ could lead to further depolarization of the membrane. Therefore the possibility that SLC26A11 in cortical neurons is required for a DIDS and GlyH-101 sensitive $Cl^-$ channel that is opened by depolarization was tested. Such outwardly rectifying, non-inactivating DIDS-sensitive conductances have previously been described in neurons (Smith et al., 1995), although their molecular identity remains unknown. Whole cell voltage clamp recordings were obtained under conditions to reveal voltage-dependent $Cl^-$ currents by blocking other known voltage-gated channels with a cocktail of blockers. We targeted layer 4 neurons in cortical slices (FIG. 11A), the same cell types that were also imaged in the swelling studies described above. Depolarization to −20 mV or greater elicited a non-inactivating $Cl^-$ current that was blocked by DIDS and was not present when external $[Cl^-]$ was reduced (FIG. 11C-E; p<0.001, ANOVA). In addition, dialysis of neurons with GlyH-101 at concentrations that prevented neuronal swelling were found to also inhibit the voltage-dependent $Cl^-$ current and occluded the effect of DIDS (FIGS. 11D and 11E; p<0.001, ANOVA). Finally, recordings were made from neurons transfected with siRNA against either SLC26A11 or luciferase (control) using LNPs visualized with DiI. We found that knockdown of SLC26A11 attenuated the DIDS and GlyH-101 sensitive $Cl^-$ current (FIGS. 11C-11E; p<0.001, ANOVA), demonstrating that SLC26A11 protein is a requirement for an outwardly rectifying $Cl^-$ current activated in substantially depolarized neurons.

TABLE E2

Characterization of LNP-siRNA systems

| siRNA | Size | PDI | siRNA/Lipid Ratio mg/μmol |
|---|---|---|---|
| Luc | 48.9 | 0.039 | 0.050 |
| SLC4A3 | 50.6 | 0.134 | 0.064 |
| SLC4A8 | 61.5 | 0.075 | 0.067 |
| SLC4A10 | 59.3 | 0.080 | 0.062 |
| SLC26A11-1 | 51.4 | 0.200 | 0.052 |
| SLC26A11-2 | 49.3 | 0.048 | 0.051 |

The invention claimed is:

1. A method for reducing swelling of a brain cell, comprising specifically inhibiting SLC26A11-mediated Cl- import in the cell, wherein the SLC26A11-mediated Cl- import in the brain cell is inhibited by reducing the level of SLC26A11 expression in the cell via delivery of one or more siRNA targeting SLC26A11.

2. The method of claim 1, wherein the brain cell is a neuron.

3. The method of claim 1, wherein the brain cell expresses an NMDA receptor; an ionotropic Glutamate receptor; and/or a voltage-gated sodium channel.

4. The method of claim 1, wherein the brain cell has experienced an increase in internal Na+ concentration, an increase in internal Cl- concentration; and/or a depolarization.

5. The method of claim 1, wherein the SLC26A11-mediated Cl- import in the brain cell is inhibited by reducing SLC26A11 activity.

6. A method for reducing internal Cl- concentration in a brain cell, comprising specifically inhibiting SLC26A11-mediated Cl- import in the cell, wherein the SLC26A11-mediated Cl- import in the brain cell by reducing the level of SLC26A11 expression in the cell via delivery of one or more siRNA targeting SLC26A11.

7. The method of claim 6, wherein the brain cell is a neuron.

8. The method of claim 6, wherein the brain cell expresses an NMDA receptor; an ionotropic Glutamate receptor; and/or a voltage-gated sodium channel.

9. The method of claim 6, wherein the brain cell has experienced an increase in internal Na+ concentration and/or a depolarization.

10. The method of claim 6, wherein the brain cell is swollen.

11. The method of claim 6, wherein the SLC26A11-mediated Cl- import in the brain cell is inhibited by reducing SLC26A11 activity.

12. A method of treating brain edema in a subject comprising specifically inhibiting SLC26A11-mediated Cl- import in a brain cell of the subject, wherein the SLC26A11-mediated Cl- import in the brain cell is inhibited by reducing the level of SLC26A11 expression in the cell via delivery of one or more siRNA targeting SLC26A11.

13. The method of claim 12, wherein the brain edema is cytotoxic brain edema, focal brain edema, or global brain edema.

14. The method of claim 12, wherein the subject has traumatic brain injury, brain surgery, ischemic stroke, brain hemorrhage, brain inflammation, meningitis, encephalitis, Reye's Syndrome, infection, migraine, a tumor, a brain tumor, poisoning, severe acute mountain sickness, high altitude cerebral edema, or brain hypoxia resulting in edema.

* * * * *

SEQUENCE LISTING

<160> NUMBER OF SEQ ID NOS: 16

<210> SEQ ID NO 1
<211> LENGTH: 606
<212> TYPE: PRT
<213> ORGANISM: Homo sapiens

<400> SEQUENCE: 1

```
Met Pro Ser Ser Val Thr Ala Leu Gly Gln Ala Arg Ser Ser Gly Pro
1               5                   10                  15

Gly Met Ala Pro Ser Ala Cys Cys Ser Pro Ala Ala Leu Gln Arg
            20                  25                  30

Arg Leu Pro Ile Leu Ala Trp Leu Pro Ser Tyr Ser Leu Gln Trp Leu
            35                  40                  45

Lys Met Asp Phe Val Ala Gly Leu Ser Val Gly Leu Thr Ala Ile Pro
        50                  55                  60

Gln Ala Leu Ala Tyr Ala Glu Val Ala Gly Leu Pro Pro Gln Tyr Gly
65                  70                  75                  80

Leu Tyr Ser Ala Phe Met Gly Cys Phe Val Tyr Phe Leu Gly Thr
                85                  90                  95

Ser Arg Asp Val Thr Leu Gly Pro Thr Ala Ile Met Ser Leu Leu Val
                100                 105                 110

Ser Phe Tyr Thr Phe His Glu Pro Ala Tyr Ala Val Leu Leu Ala Phe
                115                 120                 125

Leu Ser Gly Cys Ile Gln Leu Ala Met Gly Val Leu Arg Leu Gly Phe
            130                 135                 140

Leu Leu Asp Phe Ile Ser Tyr Pro Val Ile Lys Gly Phe Thr Ser Ala
145                 150                 155                 160

Ala Ala Val Thr Ile Gly Phe Gly Gln Ile Lys Asn Leu Leu Gly Leu
                165                 170                 175

Gln Asn Ile Pro Arg Pro Phe Phe Leu Gln Val Tyr His Thr Phe Leu
            180                 185                 190

Arg Ile Ala Glu Thr Arg Val Gly Asp Ala Val Leu Gly Leu Val Cys
            195                 200                 205

Met Leu Leu Leu Val Leu Lys Leu Met Arg Asp His Val Pro Pro
    210                 215                 220

Val His Pro Glu Met Pro Pro Gly Val Arg Leu Ser Arg Gly Leu Val
225                 230                 235                 240

Trp Ala Ala Thr Thr Ala Arg Asn Ala Leu Val Val Ser Phe Ala Ala
                245                 250                 255

Leu Val Ala Tyr Ser Phe Glu Val Thr Gly Tyr Gln Pro Phe Ile Leu
                260                 265                 270

Thr Gly Glu Thr Ala Glu Gly Leu Pro Pro Val Arg Ile Pro Pro Phe
            275                 280                 285

Ser Val Thr Thr Ala Asn Gly Thr Ile Ser Phe Thr Glu Met Val Gln
            290                 295                 300

Asp Met Gly Ala Gly Leu Ala Val Val Pro Leu Met Gly Leu Leu Glu
305                 310                 315                 320

Ser Ile Ala Val Ala Lys Ala Phe Ala Ser Gln Asn Asn Tyr Arg Ile
                325                 330                 335

Asp Ala Asn Gln Glu Leu Leu Ala Ile Gly Leu Thr Asn Met Leu Gly
            340                 345                 350

Ser Leu Val Ser Ser Tyr Pro Val Thr Gly Ser Phe Gly Arg Thr Ala
                355                 360                 365
```

```
Val Asn Ala Gln Ser Gly Val Cys Thr Pro Ala Gly Gly Leu Val Thr
    370                 375                 380

Gly Val Leu Val Leu Leu Ser Leu Asp Tyr Leu Thr Ser Leu Phe Tyr
385                 390                 395                 400

Tyr Ile Pro Lys Ser Ala Leu Ala Ala Val Ile Met Ala Val Ala
                405                 410                 415

Pro Leu Phe Asp Thr Lys Ile Phe Arg Thr Leu Trp Arg Val Lys Arg
                420                 425                 430

Leu Asp Leu Leu Pro Leu Cys Val Thr Phe Leu Leu Cys Phe Trp Glu
                435                 440                 445

Val Gln Tyr Gly Ile Leu Ala Gly Ala Leu Val Ser Leu Leu Met Leu
    450                 455                 460

Leu His Ser Ala Ala Arg Pro Glu Thr Lys Val Ser Glu Gly Pro Val
465                 470                 475                 480

Leu Val Leu Gln Pro Ala Ser Gly Leu Ser Phe Pro Ala Met Glu Ala
                485                 490                 495

Leu Arg Glu Glu Ile Leu Ser Arg Ala Leu Glu Val Ser Pro Pro Arg
                500                 505                 510

Cys Leu Val Leu Glu Cys Thr His Val Cys Ser Ile Asp Tyr Thr Val
                515                 520                 525

Val Leu Gly Leu Gly Glu Leu Gln Asp Phe Gln Lys Gln Gly Val
    530                 535                 540

Ala Leu Ala Phe Val Gly Leu Gln Val Pro Val Arg Val Leu Leu
545                 550                 555                 560

Ser Ala Asp Leu Lys Gly Phe Gln Tyr Phe Ser Thr Leu Glu Glu Ala
                565                 570                 575

Glu Lys His Leu Arg Gln Glu Pro Gly Thr Gln Pro Tyr Asn Ile Arg
                580                 585                 590

Glu Asp Ser Ile Leu Asp Gln Lys Val Ala Leu Leu Lys Ala
                595                 600                 605

<210> SEQ ID NO 2
<211> LENGTH: 590
<212> TYPE: PRT
<213> ORGANISM: Ratus norvegicus

<400> SEQUENCE: 2

Met Ala Pro Asp Thr His Cys Cys Ser Arg Ala Asp Leu Arg Arg Arg
1               5                   10                  15

Leu Pro Val Leu Ala Trp Leu Pro Asn Tyr Ser Leu Arg Trp Leu Arg
                20                  25                  30

Met Asp Val Ile Ala Gly Leu Ser Val Gly Leu Thr Val Ile Pro Gln
                35                  40                  45

Ala Leu Ala Tyr Ala Glu Val Ala Gly Leu Pro Pro Gln Tyr Gly Leu
    50                  55                  60

Tyr Ser Ala Phe Met Gly Cys Phe Val Tyr Phe Val Leu Gly Thr Ser
65                  70                  75                  80

Arg Asp Val Thr Leu Gly Pro Thr Ala Ile Met Ser Leu Leu Val Ser
                85                  90                  95

Tyr Tyr Thr Phe Arg Glu Pro Ala Tyr Ala Val Leu Leu Ala Phe Leu
                100                 105                 110

Ser Gly Cys Ile Gln Leu Ala Met Gly Leu Leu His Leu Gly Phe Leu
                115                 120                 125

Leu Asp Phe Ile Ser Cys Pro Val Ile Lys Gly Phe Thr Ser Ala Ala
                130                 135                 140
```

-continued

```
Ser Ile Thr Ile Gly Phe Gly Gln Val Lys Asn Leu Leu Gly Leu Gln
145                 150                 155                 160

Asn Ile Pro Arg Gln Phe Phe Leu Gln Val Tyr His Thr Phe Leu His
                165                 170                 175

Ile Gly Glu Thr Arg Val Gly Asp Ala Ile Leu Gly Leu Val Cys Met
            180                 185                 190

Val Leu Leu Leu Val Leu Lys Leu Met Arg Glu His Ile Pro Pro Pro
        195                 200                 205

His Pro Glu Met Pro Leu Gly Val Lys Phe Ser Arg Gly Leu Val Trp
    210                 215                 220

Thr Val Thr Thr Ala Arg Asn Ala Leu Val Val Ser Phe Ala Ala Leu
225                 230                 235                 240

Ile Ala Tyr Ala Phe Glu Val Thr Gly Ser His Pro Phe Ile Leu Thr
                245                 250                 255

Gly Lys Ile Ala Gln Gly Leu Pro Pro Val Arg Met Pro Pro Phe Ser
            260                 265                 270

Val Thr Thr Asp Asn Lys Thr Ile Ser Phe Ser Glu Met Val Gln Val
        275                 280                 285

Ser Gly Cys Arg Ala Ser Ser Met Ala Glu Ala Glu Arg Leu His Cys
    290                 295                 300

Pro Phe Ser Leu Ala Ser Gln Asn Asn Tyr Arg Ile Asp Ala Asn Gln
305                 310                 315                 320

Glu Leu Leu Ala Ile Gly Leu Thr Asn Val Leu Gly Ser Leu Val Ser
                325                 330                 335

Ser Tyr Pro Val Thr Gly Ser Phe Gly Arg Thr Ala Val Asn Ala Gln
            340                 345                 350

Thr Gly Val Cys Thr Pro Ala Gly Leu Val Thr Gly Val Leu Val
        355                 360                 365

Leu Leu Ser Leu Asp Tyr Leu Thr Leu Leu Phe Tyr Tyr Ile Pro Lys
    370                 375                 380

Ser Ala Leu Ala Ala Val Ile Ile Met Ala Val Ala Pro Leu Phe Asp
385                 390                 395                 400

Val Lys Ile Phe Arg Arg Leu Trp Leu Val Gln Arg Leu Asp Leu Leu
                405                 410                 415

Pro Leu Cys Val Thr Phe Leu Leu Ser Phe Trp Glu Ile Gln Tyr Gly
            420                 425                 430

Ile Leu Ala Gly Thr Leu Val Ser Leu Ile Leu Leu His Ser Val
        435                 440                 445

Ala Arg Pro Lys Thr Gln Val Ser Glu Gly Gln Ile Leu Val Leu Gln
    450                 455                 460

Pro Ala Ser Gly Leu His Phe Pro Ala Val Asp Ala Leu Arg Glu Ala
465                 470                 475                 480

Met Thr Lys Arg Ala Leu Glu Ala Ser Pro Pro Arg Ser Ala Val Leu
                485                 490                 495

Glu Cys Thr His Val Ser Asn Ile Asp Tyr Thr Val Ile Leu Gly Leu
            500                 505                 510

Gly Glu Leu Leu Glu Asp Phe Gln Lys Lys Gly Val Thr Leu Ala Phe
        515                 520                 525

Val Gly Leu Gln Val Pro Val Leu Arg Thr Leu Leu Ala Ala Asp Leu
    530                 535                 540

Lys Gly Phe Gln Tyr Phe Thr Thr Leu Glu Glu Ala Glu Lys Ser Leu
545                 550                 555                 560
```

Gln Gln Glu Pro Gly Thr Gln Pro Tyr Ser Ile Arg Glu Asp Thr Ala
                565                 570                 575

Pro Glu His Arg Ser Ser Leu Leu Lys Ser Pro Ser Gly Pro
            580                 585                 590

<210> SEQ ID NO 3
<211> LENGTH: 593
<212> TYPE: PRT
<213> ORGANISM: Mus musculus

<400> SEQUENCE: 3

Met Ala Pro Asp Thr Cys Cys Cys Ser Ala Thr Ala Leu Arg Arg Arg
1               5                   10                  15

Leu Pro Val Leu Ala Trp Val Pro Asp Tyr Ser Leu Gln Trp Leu Arg
            20                  25                  30

Leu Asp Phe Ile Ala Gly Leu Ser Val Gly Leu Thr Val Ile Pro Gln
        35                  40                  45

Ala Leu Ala Tyr Ala Glu Val Ala Gly Leu Pro Pro Gln Tyr Gly Leu
    50                  55                  60

Tyr Ser Ala Phe Met Gly Cys Phe Val Tyr Phe Leu Gly Thr Ser
65              70                  75                  80

Arg Asp Val Thr Leu Gly Pro Thr Ala Ile Met Ser Leu Leu Val Ser
                85                  90                  95

Phe Tyr Thr Phe Arg Glu Pro Ala Tyr Ala Val Leu Leu Ala Phe Leu
            100                 105                 110

Ser Gly Cys Ile Gln Leu Ala Met Gly Leu Leu His Leu Gly Phe Leu
        115                 120                 125

Leu Asp Phe Ile Ser Cys Pro Val Ile Lys Gly Phe Thr Ser Ala Ala
    130                 135                 140

Ser Ile Thr Ile Gly Phe Gly Gln Ile Lys Asn Leu Leu Gly Leu Gln
145                 150                 155                 160

Lys Ile Pro Arg Gln Phe Phe Leu Gln Val Tyr His Thr Phe Leu His
                165                 170                 175

Ile Gly Glu Thr Arg Val Gly Asp Ala Val Leu Gly Leu Ala Ser Met
            180                 185                 190

Leu Leu Leu Leu Val Leu Lys Cys Met Arg Glu His Met Pro Pro Pro
        195                 200                 205

His Pro Glu Met Pro Leu Ala Val Lys Phe Ser Arg Gly Leu Val Trp
    210                 215                 220

Thr Val Thr Thr Ala Arg Asn Ala Leu Val Val Ser Ser Ala Ala Leu
225                 230                 235                 240

Ile Ala Tyr Ala Phe Glu Val Thr Gly Ser His Pro Phe Val Leu Thr
                245                 250                 255

Gly Lys Ile Ala Glu Gly Leu Pro Pro Val Arg Ile Pro Pro Phe Ser
            260                 265                 270

Val Thr Arg Asp Asn Lys Thr Ile Ser Phe Ser Glu Met Val Gln Asp
        275                 280                 285

Met Gly Ala Gly Leu Ala Val Val Pro Leu Met Gly Leu Leu Glu Ser
    290                 295                 300

Ile Ala Val Ala Lys Ser Phe Ala Ser Gln Asn Asn Tyr Arg Ile Asp
305                 310                 315                 320

Ala Asn Gln Glu Leu Leu Ala Ile Gly Leu Thr Asn Val Leu Gly Ser
                325                 330                 335

Leu Val Ser Ser Tyr Pro Val Thr Gly Ser Phe Gly Arg Thr Ala Val
            340                 345                 350

Asn Ala Gln Thr Gly Val Cys Thr Pro Ala Gly Gly Leu Val Thr Gly
            355                 360                 365
Ala Leu Val Leu Leu Ser Leu Asn Tyr Leu Thr Ser Leu Phe Ser Tyr
    370                 375                 380
Ile Pro Lys Ser Ala Leu Ala Ala Val Ile Ile Thr Ala Val Thr Pro
385                 390                 395                 400
Leu Phe Asp Val Lys Ile Phe Arg Ser Leu Trp Arg Val Gln Arg Leu
                405                 410                 415
Asp Leu Leu Pro Leu Cys Val Thr Phe Leu Leu Ser Phe Trp Glu Ile
            420                 425                 430
Gln Tyr Gly Ile Leu Ala Gly Ser Leu Val Ser Leu Ile Leu Leu
        435                 440                 445
His Ser Val Ala Arg Pro Lys Thr Gln Val Ser Glu Gly Gln Ile Phe
    450                 455                 460
Val Leu Gln Pro Ala Ser Gly Leu Tyr Phe Pro Ala Ile Asp Ala Leu
465                 470                 475                 480
Arg Glu Ala Ile Thr Asn Arg Ala Leu Glu Ala Ser Pro Pro Arg Ser
                485                 490                 495
Ala Val Leu Glu Cys Thr His Ile Ser Ser Val Asp Tyr Thr Val Ile
            500                 505                 510
Val Gly Leu Gly Glu Leu Leu Glu Asp Phe Gln Lys Lys Gly Val Ala
        515                 520                 525
Leu Ala Phe Val Gly Leu Gln Val Pro Val Leu Arg Thr Leu Leu Ala
    530                 535                 540
Ala Asp Leu Lys Gly Phe Arg Tyr Phe Thr Thr Leu Glu Glu Ala Glu
545                 550                 555                 560
Lys Phe Leu Gln Gln Glu Pro Gly Thr Glu Pro Asn Ser Ile His Glu
                565                 570                 575
Asp Ala Val Pro Glu Gln Arg Ser Ser Leu Leu Lys Ser Pro Ser Gly
            580                 585                 590
Pro

<210> SEQ ID NO 4
<211> LENGTH: 2930
<212> TYPE: DNA
<213> ORGANISM: Homo sapiens

<400> SEQUENCE: 4

| | | | | |
|---|---|---|---|---|
| acgtgcgcgc cagaccccgc cccggcctgt ccccggcgat tcctgcggac ccagctgcgg | 60 |
| cgacgccagg agaccccaag ctgcatcgcc gagtggaagc aactagaact ccagggctgt | 120 |
| gaaagccaca ggtgggggct gagcgaggcg tggcctcagg agcggaggac cccccactc | 180 |
| tccctcgagc gccgcagtcc accgtagcgg gtggagcccg ccttggtgcg cagttggaaa | 240 |
| acctcggagc cccgctggat ctcctggctg ccacccgcac ccccgccag cctacgcccc | 300 |
| accgtagaga tgccttcttc ggtgacggcg ctgggtcagg ccaggtcctc tggccccggg | 360 |
| atggccccga gcgcctgctg ctgctcccct gcggccctgc agaggaggct gcccatcctg | 420 |
| gcgtggctgc ccagctactc cctgcagtgg ctgaagatgg atttcgtcgc cggcctctca | 480 |
| gttggcctca ctgccattcc ccaggcgctg gcctatgctg aagtggctgg actcccgccc | 540 |
| cagtatggcc tctactctgc cttcatgggc tgcttcgtgt atttcttcct gggcacctcc | 600 |
| cgggatgtga ctctgggccc caccgccatt atgtccctcc tggtctcctt ctacaccttc | 660 |
| catgagcccg cctacgctgt gctgctggcc ttcctgtccg gctgcatcca gctggccatg | 720 |

```
ggggtcctgc gtttggggtt cctgctggac ttcatttcct accccgtcat taaaggcttc    780
acctctgctg ctgccgtcac catcggcttt ggacagatca agaacctgct gggactacag    840
aacatcccca ggccgttctt cctgcaggtg taccacacct tcctcaggat tgcagagacc    900
agggtaggtg acgccgtcct ggggctggtc tgcatgctgc tgctgctggt gctgaagctg    960
atgcgggacc acgtgcctcc cgtccacccc gagatgcccc ctggtgtgcg gctcagccgt   1020
gggctggtct gggctgccac gacagctcgc aacgccctgg tggtctcctt cgcagccctg   1080
gttgcgtact ccttcgaggt gactggatac cagccttcca tcctaacagg ggagacagct   1140
gaggggctcc ctccagtccg gatcccgccc ttctcagtga ccacagccaa cgggacgatc   1200
tccttcaccg agatggtgca ggacatggga gccgggctgg ccgtggtgcc cctgatgggc   1260
ctcctggaga gcattgcggt ggccaaagcc ttcgcatctc agaataatta ccgcatcgat   1320
gccaaccagg agctgctggc catcggtctc accaacatgt gggctccct cgtctcctcc    1380 tacccggtca caggcagctt tggacggaca gccgtgaacg ctcagtcggg ggtgtgcacc   1440
ccggcggggg gcctggtgac gggagtgctg gtgctgctgt ctctggacta cctgacctca   1500
ctgttctact acatccccaa gtctgccctg gctgccgtca tcatcatggc cgtggccccg   1560
ctgttcgaca ccaagatctt caggacgctc tggcgtgtta agaggctgga cctgctgccc   1620
ctgtgcgtga ccttcctgct gtgcttctgg gaggtgcagt acggcatcct ggccggggcc   1680
ctggtgtctc tgctcatgct cctgcactct gcagccaggc ctgagaccaa ggtgtcagag   1740
gggccggttc tggtcctgca gccggccagc ggcctgtcct ccctgccat ggaggctctg     1800 cgggaggaga tcctaagccg ggccctggaa gtgtccccgc cacgctgcct ggtcctggag   1860
tgcacccatg tctgcagcat cgactacact gtggtgctgg gactcggcga gctcctccag   1920
gacttccaga agcagggcgt cgccctggcc tttgtgggcc tgcaggtccc cgttctccgt   1980
gtcctgctgt ccgctgacct gaaggggttc cagtacttct ctaccctgga agaagcagag   2040
aagcacctga ggcaggagcc agggacccag ccctacaaca tcagagaaga ctccattctg   2100
gaccaaaagg ttgccctgct caaggcataa tggggccacc cgtgggcatc cacagttttgc   2160 agggtgttcc ggaaggttct tgtcactgtg attggatgct ggatgccgcc tgatagacat   2220
gctggcctgg ctgagaaacc cctgagcagg taacccaggg aagagaagga agccaggcct   2280
ggaggtccac ggcagtggga gtggggctca ctggcttcct gtgggatgac tggaaaatga   2340
cctcgctgct gttccctggc atgaccctct ttggaagagt ggtttggaga gagccttcta   2400
gaatgacaga ctgtgcgagg aagcaggggc aggggtttcc agcccgggct gtgcgaggca   2460
tcctggggct ggcagcacct tcccggctca ccagtgccac ctgcggggga gggacggggc   2520
aggcaggagt ctgggaggcg ggtccgctcc tcttgtctgc ggcatctgtg ctctccgaga   2580
gaaaaccaag gtgtgtcaaa tgacgtcaag tctctatta aaaataattt tgtgttttct     2640
aaatggaaaa agtgatagct ttggtgattt tgtaaaagtc ataatgcttt attgtaaaaa   2700
atacaggaaa ccaccccctca ccctgtccac ttgggtgatc attccagacc cctccccaaa   2760
catgcatatg tacctgtccg tcagtgtgtg gatgtatgtt acagttcta cataaatggg     2820 atcattttat acatggtgct ctggaaccca cattttcat gcagtcattt gcagtgaatt     2880
atttattgtg ataataaata gcattagaat acaagatttt taaaaaaaaa               2930
```

<210> SEQ ID NO 5
<211> LENGTH: 1999
<212> TYPE: DNA

<213> ORGANISM: Rattus norvegicus

<400> SEQUENCE: 5

```
atgtactgcc cactctgttc ctgagattcc tgaggactca gctacggcca cttcggagga      60
ccccgagcct cggcgttcgg tggctttgta aaaggtctgg gtcaggccag atcccccag      120
cctgatcatg gcaccagaca cacactgctg ctccagggca gacctgagga ggaggctacc     180
cgtcctggcc tggctgccca actactctct gcggtggctg agaatggacg tcatcgctgg     240
actctccgtg gtctcaccg tcatccccca ggccctggcc tatgcagaag tggctggact      300
cccgccccag tacggtctct actctgcctt catggggtgc ttcgtgtact tcgtcctggg     360
cacctcccgg gatgtgactc tgggccccac ggctatcatg tctctcctgg tatcctacta    420
caccttccgt gagcctgcct atgccgtgct gcttgccttc ctgtctgggt gtatccagtt    480
ggccatgggg ctcctgcatt tggggttcct gctggacttc atctcctgcc ctgtcattaa    540
aggcttcaca tccgctgcca gcatcacaat tggctttgga caggtcaaga acctgctggg    600
attacagaac atccccggc agttcttcct ccaggtgtac cacaccttcc tccacatcgg     660
agagaccagg gtgggcgatg ccatcctggg actggtctgc atggtgctgc tgcttgtgct    720
gaagcttatg cgtgaacaca ttcctcctcc ccatcctgag atgccccttg gcgtgaagtt    780
cagccgtggg ctagtgtgga ccgtcacaac agctcgcaac gccttggtgg tctccttcgc    840
ggccctgatt gcttacgcct tcgaggtgac aggatcccat ccgttcattc tgactggaaa    900
gatcgcccag gggctccctc ctgtgaggat gccgcccttc tcagtgacca cagacaataa    960
gaccatctct ttctctgaga tggtgcagga catgggggtc ggactggctg tggtgcctct   1020
gatgggcctc ctggagacca ttgctgtggc caaatccttc gcctcccaga ataattaccg   1080
cattgatgcc aaccaggagc tgctggccat cggcctcacc aatgtgctgg gctccctagt   1140
ctcgtcttac ccggtcactg gcagctttgg gcggacagca gtgaatgccc agacggggt    1200
gtgtaccccg gcaggaggcc tggtgactgg tgtcctggtg ctgctgtctc tggactacct   1260
gaccttactg ttctactata tccccaagtc tgcactggct gccgtcatca tcatggctgt   1320
ggccccgctc tttgacgtca agatcttcag gaggctctgg cttgttcaga gtacgtaccg   1380
caaagcaggc agctctgggg tgacatctgg gaatgcctag gcctttgtta tccctcctgg   1440
cctgtgggct ggagctgtgg cactctggta aacttaggag aagatacact ggaggtggct   1500
gcttagcgag cgaagctgga cttcggtcca cacagagctg gacagagctc tgtagctttg   1560
gagtggagag cagagttttcc ccactcggtg tcctcatcct ctcctccccc catctttctc   1620
ttcctgaggg ggtggtgaca gaaaggcctc acacaatagt ctctcagtct ccccatctc   1680
ccgcccctgag agcccctcat ccactggtttt cttttaacaaa tcagaggtta acttttcctc   1740
cttcctcgtt gtccagttgt cgggtgtgtg tcccagcttt ctgtgtacca ggtttcatct    1800
ttaggacagc cttgagatat atcagtgtag atgtgtggaa ctgatgttct ccaaggaaac   1860
taggactcca gaaagggcat ggcctgtcta ggttgccaca tcagaggtac aatctcgac    1920
tgagtccaag tactttgtgc ccagggcaat aaatcctcct ggtctcctgg agtcacaaga   1980
cacaccacac acgcaccat                                                1999
```

<210> SEQ ID NO 6
<211> LENGTH: 2692
<212> TYPE: DNA
<213> ORGANISM: Mus musculus

<400> SEQUENCE: 6

| | |
|---|---|
| atgtcctgcc cactctgttt ctgagattcc tgcggactca gctaccgcca cttcggaaga | 60 |
| ccctgagtct cagcgtccgc tctgtgaaag gtctgggtca gaccagatcc cccagcctgc | 120 |
| acatggcacc agacacatgc tgctgctctg ctacggccct gaggaggagg ctacccgtcc | 180 |
| tggcctgggt gcctgactac tctctgcagt ggctgaggct ggacttcatc gctggacttt | 240 |
| ccgtgggact caccgtcatt ccccaggccc tggcctatgc agaagtggct ggactcccac | 300 |
| cccagtacgg cctctactct gccttcatgg gatgcttcgt gtatttcttc ctgggcacct | 360 |
| cccgggatgt gactctgggc ccacggcta tcatgtctct cctggtgtcc ttctacacct | 420 |
| tccgtgagcc tgcctatgct gtgctgcttg ccttcctgtc tgggtgtatc cagctggcca | 480 |
| tggggctcct gcatttgggg ttcctgctgg acttcatctc ctgccctgtc attaaaggct | 540 |
| tcacctccgc tgccagcatc acaattggct ttggacagat caagaacctg ctgggattgc | 600 |
| agaaaatccc ccggcagttc ttcctccagg tgtaccacac cttcctccac atcggagaga | 660 |
| ccagggtagg cgacgctgtc ctcggactgg cctccatgtt gctgctgctt gtgctgaagt | 720 |
| gtatgcggga acacatgcct cctccccatc ctgagatgcc ccttgccgtg aagttcagcc | 780 |
| gtgggctggt gtggactgtc acaacagctc gcaatgccct ggtggtctcc tccgcggctc | 840 |
| tgattgctta cgccttcgag gtgacaggat cccatccctt tgttctgact ggaaagatcg | 900 |
| ccgaggggct ccctccggtg cggatcccac ccttctcagt gaccagggac aataagacca | 960 |
| tctcgttctc tgagatggtg caggacatgg gggccggact ggctgtggta cctctgatgg | 1020 |
| ggctcctgga gagcattgcc gtggccaaat ccttcgcgtc tcagaataac taccgcattg | 1080 |
| atgctaacca ggaactactg gccattggcc tcaccaatgt gctgggctcc ctcgtctcct | 1140 |
| cttacccagt cactggcagc tttgggcgga cagctgtgaa tgcccagaca ggggtgtgta | 1200 |
| ccccggcagg aggcctggtg actggtgccc tggtgctgct gtccctgaac tacttgacct | 1260 |
| cactcttctc ctatatcccc aagtctgccc tggctgccgt gatcatcacg gctgtgaccc | 1320 |
| cactctttga tgtcaagatc ttcaggagtc tctggcgcgt tcagaggctg gatctgctac | 1380 |
| cactgtgtgt gacgttcctg ctgtccttct gggagatcca gtacggtatc ctggccggta | 1440 |
| gcctggtgtc tttgctcatt ctcctgcact cggtagctag gcccaagact caggtgtcag | 1500 |
| aaggacaaat ttttgttctt cagccggcca gcggcctgta cttccctgca attgatgccc | 1560 |
| tccgagaggc aataacgaac cgggcactgg aagcatcccc accacgttcc gcggttctgg | 1620 |
| agtgcacgca tatcagcagt gtagactaca ccgtgatcgt gggactcggt gagctcctgg | 1680 |
| aggacttcca gaagaaagga gtcgccctgg cctttgttgg cctacaggtg cccgtgctcc | 1740 |
| gcacactgtt ggccgctgac ctcaaggggt tccgttactt caccactctg gaggaggctg | 1800 |
| agaaattcct gcagcaggaa ccaggaactg agcccaacag catccatgaa gatgctgttc | 1860 |
| cagagcaaag gagctccctg ctcaagtctc cctccggccc ctgaagagca gatggtatag | 1920 |
| gaagggtttc tggaaggttc tgtcaccatg acttggagtc acctgataga ctcaccaacc | 1980 |
| tggtgggact taaaaggcac tgcataggtg gctctgggga acagcaggga gccatgtatg | 2040 |
| atttccaggg tgtcactttc ctgctgtccc ctaggtgtga gtatttgagg gctgggctga | 2100 |
| ctgaaaagtc tttcagagag agagagagag agacagagac ccagagacac acacatggct | 2160 |
| tctggcctgg tctggcaggg taaggtgaca ctctccagat cccagattct tctttggaat | 2220 |
| caggtcctac tggagaaaaa tcaaagagat tgggcatctc ggagatgtgt ctgaccatgt | 2280 |
| catgaagtct aatctgagct gaagaggtgg ccacagcatg ccacacaagg tcaattctgt | 2340 |

|  |  |  |
|---|---|---|
| ttaaaatcat gtgtttttta aatggaagtc actctggtgt ttttgtaaag caaaacaaaa | 2400 |
| acatttatgc ttactttaaa aaaaaaatcc aagaactcat gcatcctgtt cactattctc | 2460 |
| ttaactgagg tccctgccc ggacaggtgt gtatccgtca gtgtgtgcac acggtgccgt | 2520 |
| ctgatgtgaa gacccgaatc actgtattaa ggtgctttgt aaactgtctt catgcagtca | 2580 |
| ttaattgtga attatttatt gtgatgatca atgcattaa atgcaagatt tatttacctt | 2640 |
| attaaaatac aagatttatt tattgtatta aaatacaata ttctgtgggt cc | 2692 |

```
<210> SEQ ID NO 7
<211> LENGTH: 25
<212> TYPE: RNA
<213> ORGANISM: Artificial Sequence
<220> FEATURE:
<223> OTHER INFORMATION: siRNA synthesized in lab

<400> SEQUENCE: 7
ggauuacucu aucacagaca ccuac                                      25

<210> SEQ ID NO 8
<211> LENGTH: 27
<212> TYPE: RNA
<213> ORGANISM: Artificial Sequence
<220> FEATURE:
<223> OTHER INFORMATION: siRNA synthesized in lab

<400> SEQUENCE: 8
guaggugucu gugauagagu aauccac                                    27

<210> SEQ ID NO 9
<211> LENGTH: 25
<212> TYPE: RNA
<213> ORGANISM: Artificial Sequence
<220> FEATURE:
<223> OTHER INFORMATION: siRNA synthesized in lab

<400> SEQUENCE: 9
acagcggucu uaaaguuuau cccaa                                      25

<210> SEQ ID NO 10
<211> LENGTH: 27
<212> TYPE: RNA
<213> ORGANISM: Artificial Sequence
<220> FEATURE:
<223> OTHER INFORMATION: siRNA synthesized in lab

<400> SEQUENCE: 10
uugggauaaa cuuuaagacc gcuguca                                    27

<210> SEQ ID NO 11
<211> LENGTH: 25
<212> TYPE: DNA
<213> ORGANISM: Artificial Sequence
<220> FEATURE:
<223> OTHER INFORMATION: siRNA synthesized in lab

<400> SEQUENCE: 11
ugcuuauaaa gcuaaagacc gcaat                                      25

<210> SEQ ID NO 12
<211> LENGTH: 27
<212> TYPE: RNA
<213> ORGANISM: Artificial Sequence
<220> FEATURE:
<223> OTHER INFORMATION: siRNA synthesized in lab
```

```
<400> SEQUENCE: 12
auugcggucu uuagcuuuau aagcaac                                    27

<210> SEQ ID NO 13
<211> LENGTH: 25
<212> TYPE: RNA
<213> ORGANISM: Artificial Sequence
<220> FEATURE:
<223> OTHER INFORMATION: siRNA synthesized in lab

<400> SEQUENCE: 13
gcaugucagc aauauagacu acacc                                      25

<210> SEQ ID NO 14
<211> LENGTH: 27
<212> TYPE: RNA
<213> ORGANISM: Artificial Sequence
<220> FEATURE:
<223> OTHER INFORMATION: siRNA synthesized in lab

<400> SEQUENCE: 14
gguguagucu auauugcuga caugcgu                                    27

<210> SEQ ID NO 15
<211> LENGTH: 25
<212> TYPE: RNA
<213> ORGANISM: Artificial Sequence
<220> FEATURE:
<223> OTHER INFORMATION: siRNA synthesized in lab

<400> SEQUENCE: 15
ggagauccaa uacggcaucc uggca                                      25

<210> SEQ ID NO 16
<211> LENGTH: 27
<212> TYPE: RNA
<213> ORGANISM: Artificial Sequence
<220> FEATURE:
<223> OTHER INFORMATION: siRNA synthesized in lab

<400> SEQUENCE: 16
ugccaggaug ccguauugga ucuccca                                    27
```